(12) United States Patent
Young et al.

(10) Patent No.: US 11,969,499 B2
(45) Date of Patent: Apr. 30, 2024

(54) HYDROGEL DELIVERY OF STING IMMUNOTHERAPY FOR TREATMENT CANCER

(71) Applicants: WILLIAM MARSH RICE UNIVERSITY, Houston, TX (US); THE BOARD OF REGENTS OF THE UNIVERSITY OF TEXAS SYSTEM, Austin, TX (US)

(72) Inventors: Simon Young, Houston, TX (US); David Leach, Houston, TX (US); Jeffrey D. Hartgerink, Pearland, TX (US)

(73) Assignees: William Marsh Rice University, Houston, TX (US); The Board of Regents of The University of Texas System, Austin, TX (US)

( * ) Notice: Subject to any disclaimer, the term of this patent is extended or adjusted under 35 U.S.C. 154(b) by 786 days.

(21) Appl. No.: 16/618,043

(22) PCT Filed: Jun. 15, 2018

(86) PCT No.: PCT/US2018/037716
§ 371 (c)(1),
(2) Date: Nov. 27, 2019

(87) PCT Pub. No.: WO2018/232217
PCT Pub. Date: Dec. 20, 2018

(65) Prior Publication Data
US 2020/0146975 A1 May 14, 2020

Related U.S. Application Data

(60) Provisional application No. 62/520,834, filed on Jun. 16, 2017.

(51) Int. Cl.
*A61K 9/00* (2006.01)
*A61K 9/06* (2006.01)
*A61K 31/7084* (2006.01)
*A61K 39/00* (2006.01)
*A61K 39/39* (2006.01)
*A61K 45/06* (2006.01)
*A61K 47/42* (2017.01)
*A61K 47/64* (2017.01)
*A61K 47/69* (2017.01)

(52) U.S. Cl.
CPC ............ *A61K 9/0024* (2013.01); *A61K 9/06* (2013.01); *A61K 31/7084* (2013.01); *A61K 39/0011* (2013.01); *A61K 39/39* (2013.01); *A61K 47/42* (2013.01); *A61K 47/64* (2017.08); *A61K 47/6903* (2017.08); *A61K 2039/55561* (2013.01); *A61K 2039/6093* (2013.01); *A61K 2039/80* (2018.08); *A61K 45/06* (2013.01)

(58) Field of Classification Search
CPC .... A61K 9/0024; A61K 9/06; A61K 31/7084; A61K 39/0011; A61K 39/39; A61K 47/42; A61K 47/64; A61K 47/6903; A61K 45/06; A61K 2039/55561; A61K 2039/6093; A61K 2039/80
See application file for complete search history.

(56) References Cited

U.S. PATENT DOCUMENTS

| | | | |
|---|---|---|---|
| 7,569,555 B2 | 8/2009 | Karaolis | |
| 7,592,326 B2 | 9/2009 | Karaolis | |
| 7,709,458 B2 | 5/2010 | Karaolis et al. | |
| 9,226,959 B2 | 1/2016 | Kramps et al. | |
| 9,526,762 B1 | 12/2016 | Hartgerink et al. | |
| 11,203,611 B2 * | 12/2021 | Sakamuri | A61K 39/39 |
| 2005/0272662 A1 | 12/2005 | Stupp et al. | |
| 2008/0286296 A1 | 11/2008 | Ebensen et al. | |
| 2014/0205653 A1 | 7/2014 | Dubensky, Jr. et al. | |
| 2016/0287623 A1 | 10/2016 | Gejerski et al. | |
| 2017/0044206 A1 * | 2/2017 | Altman | C07H 19/23 |
| 2018/0015174 A1 | 1/2018 | Irvine et al. | |

FOREIGN PATENT DOCUMENTS

| | | |
|---|---|---|
| WO | WO 2013/185052 | 12/2013 |
| WO | WO 2014/093936 | 6/2014 |
| WO | WO 2015/185565 | 12/2015 |
| WO | WO 2016/096577 | 6/2016 |
| WO | WO 2018/045058 | 3/2018 |

OTHER PUBLICATIONS

Moore et al., Accounts of Chemical Research, 2017, 50, 714-722.*
Ablasser et al., "cGAS produces a 2'-5'-linked cyclic dinucleotide second messenger that activates STING," *Nature*, 498(7454):380-384, 2013.
Aduro Biotech, NCT02675439: Feb. 5, 2016 ed.; National Institutes of Health: ClinicalTrails.gov, 2017.
Aulisa et al., "Self-assembly of multidomain peptides: sequence variation allows control over cross-linking and viscoelasticity," *Biomacromolecules*, 10(9):2694-2698, 2009.
Bakota et al., "Injectable multidomain peptide nanofiber hydrogel as a delivery agent for stem cell secretome," *Biomacromolecules. American Chemical Society*, 12(5):1651-1657, 2011.
Barber, "STING: infection, inflammation and cancer," *Nat Rev Immunol*, 15 (12):760-770, 2015.
Corrales et al., "Direct Activation of STING in the Tumor Microenvironment Leads to Potent and Systemic Tumor Regression and Immunity," *Cell Rep.*, 11(7):1018-1030, 2015.

(Continued)

*Primary Examiner* — Marcela M Cordero Garcia
(74) *Attorney, Agent, or Firm* — Parker Highlander PLLC

(57) ABSTRACT

In one aspect, the present disclosure provides for novel compositions of matter comprising multi domain peptide (MDP) hydrogels and cyclic dinucleotides (CDNs). Also disclosed are method of using such compositions in the treatment of cancer, including in particular the treatment of head and neck cancers, such as those resistant to CDN therapy.

11 Claims, 26 Drawing Sheets
Specification includes a Sequence Listing.

(56) References Cited

OTHER PUBLICATIONS

Downey et al., "DMXAA Causes Tumor Site-Specific Vascular Disruption in Murine Non-Small Cell Lung Cancer, and like the Endogenous Non-Canonical Cyclic Dinucleotide STING Agonist, 2'3'-cGAMP, Induces M2 Macrophage Repolarization," *PLOS One*, 9(6):e99988, 2014.
Gadkaree et al., "Induction of tumor regression by intratumoral STING agonists combined with anti-programmed death-L1 blocking antibody in a preclinical squamous cell carcinoma model," *Head and Neck*, 39(6): 1086-1094, 2017.
Galler et al., "A customized self-assembling peptide hydrogel for dental pulp tissue engineering," *Tissue engineering Part A*, 18(1-2):176-184, 2012.
Galler et al., "Self-assembling multidomain peptide hydrogels: designed susceptibility to enzymatic cleavage allows enhanced cell migration and spreading," *J Am Chem Soc.*, 132(9):3217-3223, 2010.
Galler, "Self-Assembling Peptide Hydrogels Targeted for Dental Tissue Regeneration," PhD Dissertation, Rice University, UMI No. 342141, 2010.
Hanson et al., "Nanoparticle STING agonists are potent lymph node-targeted vaccine adjuvants," *Clin Invest.*, 125(6):2532-2546, 2015.
Ishikawa et al., "STING regulates intracellular DNA-mediated, type I interferon-dependent innate immunity," *Nature*, 461:788-792, 2009.
Karaolis et al., "3',5'-Cyclic diguanylic acid (c-di-GMP) inhibits basal and growth factor-stimulated human colon cancer cell proliferation," *Biochem Biophys Res Commun.*, 329(1):40-45, 2005.
Koshy et al., "Biomaterials for Enhancing Anti-Cancer Immunity," *Current Opinions Biotechnology*, 40:1-8, 2016.
Kumar et al., "Drug-triggered and cross-linked self-assembling nanofibrous hydrogels," *Journal of the American Chemical Society*, 137(14):4823-4830, 2015.
Kumar et al., "Highly angiogenic peptide nanofibers," *ACS Nano*, 9(1):860-868, 2015.
Kumar et al., "Treatment of hind limb ischemia using angiogenic peptide nanofibers," *Biomaterials*, 98:113-119, 2016.
Leach et al., "STINGel: Controlled Release of a Cyclic Dinucleotide for Enhanced Cancer Immunotherapy," *Biomaterials*, 163:67-75, 2018.
Lei et al., "MAVS-mediated apoptosis and its inhibition by viral proteins," *PLoS One*, 4(5):e5466, 2009.
Li et al., ""Missing Tooth" Multidomain Peptide Nanofibers for Delivery of Small Molecule Drugs," *Biomacromolecules*, 17:2087-2095, 2016.
Li et al., "Covalent Capture of Aligned Self-Assembling Nanofibers," *Journal of the American Chemical Society*, 139(23):8044-8050, 2017.
Miyabe et al., "A new adjuvant delivery system 'cyclic di-GMP/YSK05 liposome' for cancer immunotherapy," *Journal of Controlled Release*, 184:20-27, 2014.
Moore et al., "Enhanced Tumor Control with Combination mTOR and PD-L1 Inhibition in Syngeneic Oral Cavity Cancers," *Cancer Immunol Res.*, 4(7):611-620, 2016.
Moore et al., "Established Cell-Inflamed Tumors Rejected after Adaptive Resistance Was Reversed by Combination STING Activation and PD-1 Pathway Blockade," *Cancer Immunol Res.*; 4(12):1061-1071, 2016.
Moore et al., "Self-Assembling Multidomain Peptide Nanofibers for Delivery of Bioactive Molecules and Tissue Regeneration," *Accounts of Chemical Research*, 50(4):714-722, 2017.
Park et al., "Extended Release of Perioperative Immunotherapy Prevents Tumor Recurrence and Eliminates Metastases," *Sci Transl Med.*, 10(433), 2018.
PCT International Preliminary Report on Patentability issued in International Application No. PCT/US2018/037716, dated Dec. 17, 2019.
PCT International Search Report and Written Opinion issued in International Application No. PCT/US2018/037716, dated Sep. 7, 2018.
Romling et al., "Cyclic di-GMP as a second messenger," *Curr Opin Microbiol.*, 9(2):218-228, 2006.
Tamura et al., "The IRF Family Transcription Factors in Immunity and Oncogenesis," *Annu Rev Immunol*, 26 (1):535-584, 2008.
Wickremasinghe et al., "Controlled Angiogenesis in Peptide Nanofiber Composite Hydrogels," *ACS Biomater. Sci. Eng. American Chemical Society*, 1(9):845-854, 2015.
Yildiz et al., "Enhanced immunostimulatory activity of cyclic dinucleotides on mouse cells when complexed with a cell-penetrating peptide or combined with CpG," *Eur J Immunol.*, 45(4):1170-1179, 2015.

* cited by examiner

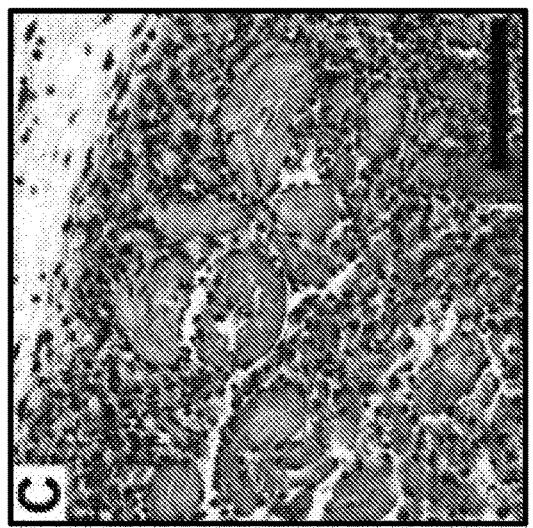
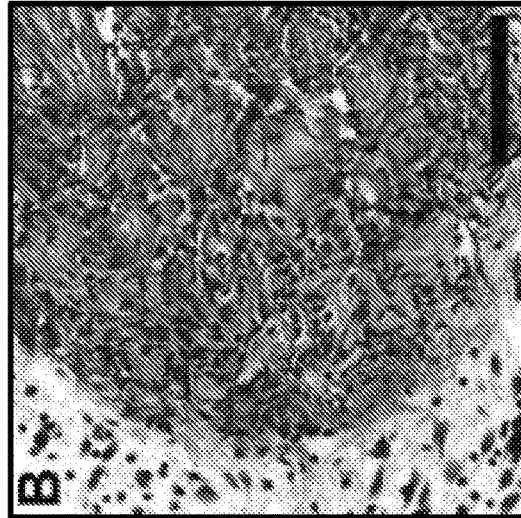
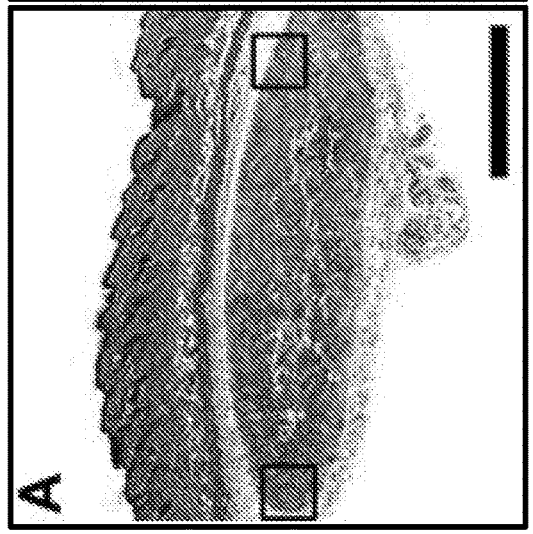
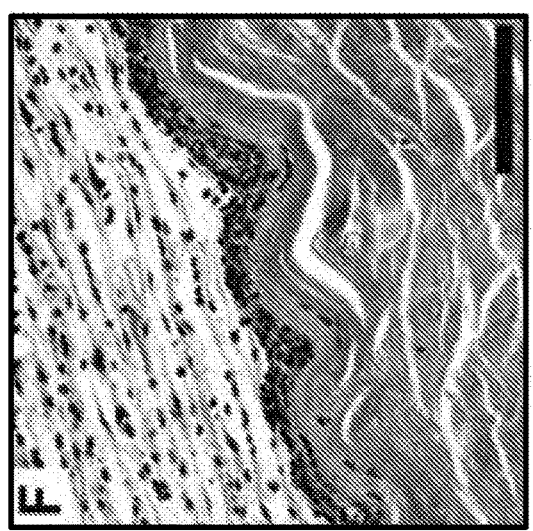
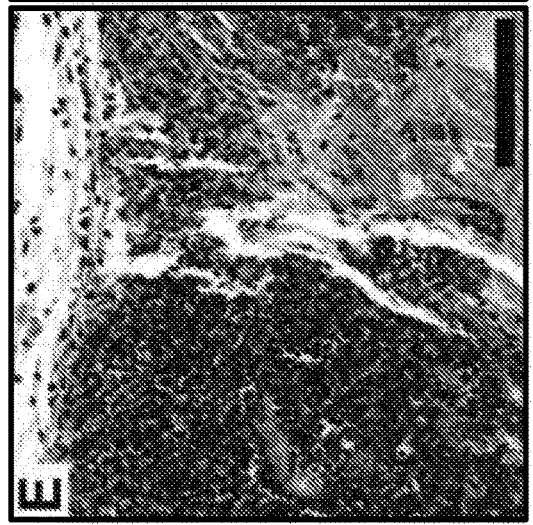
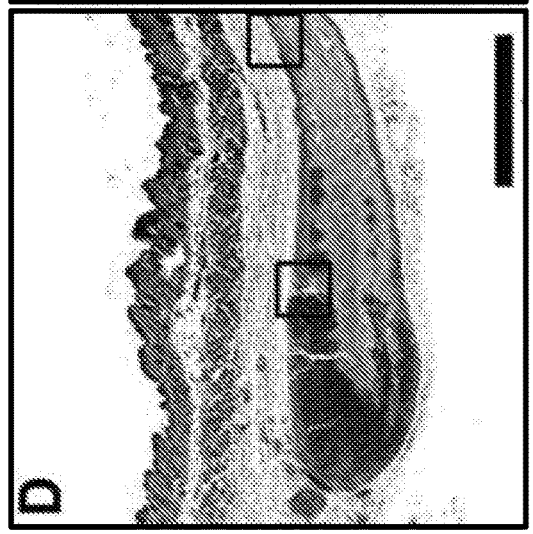

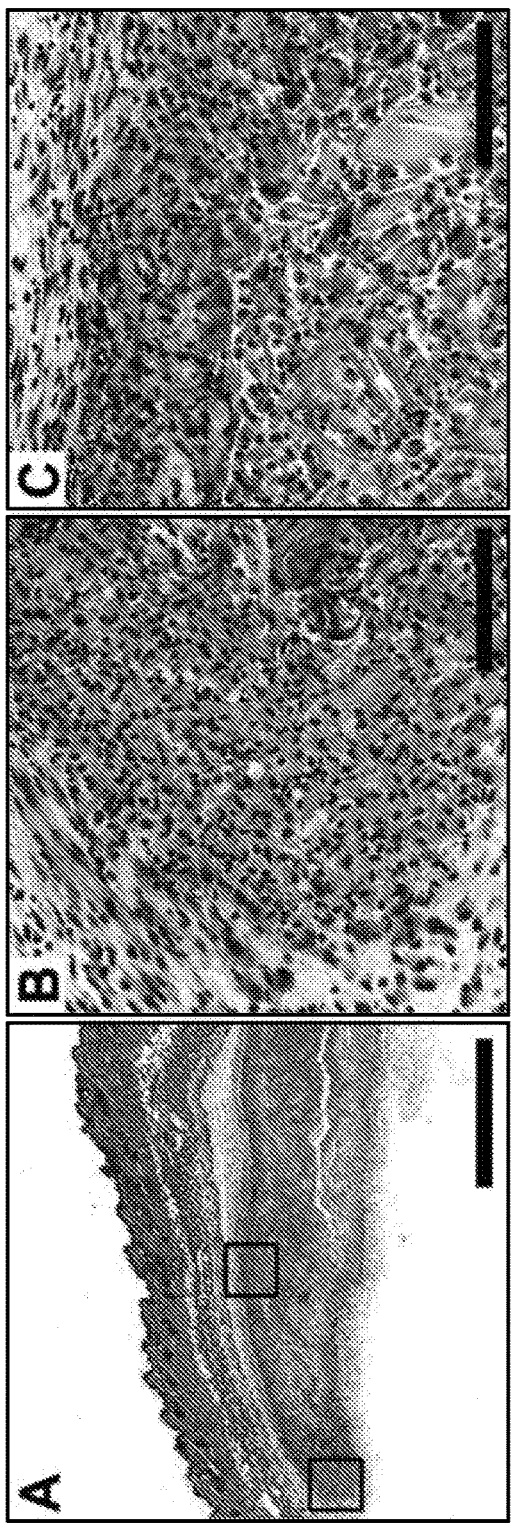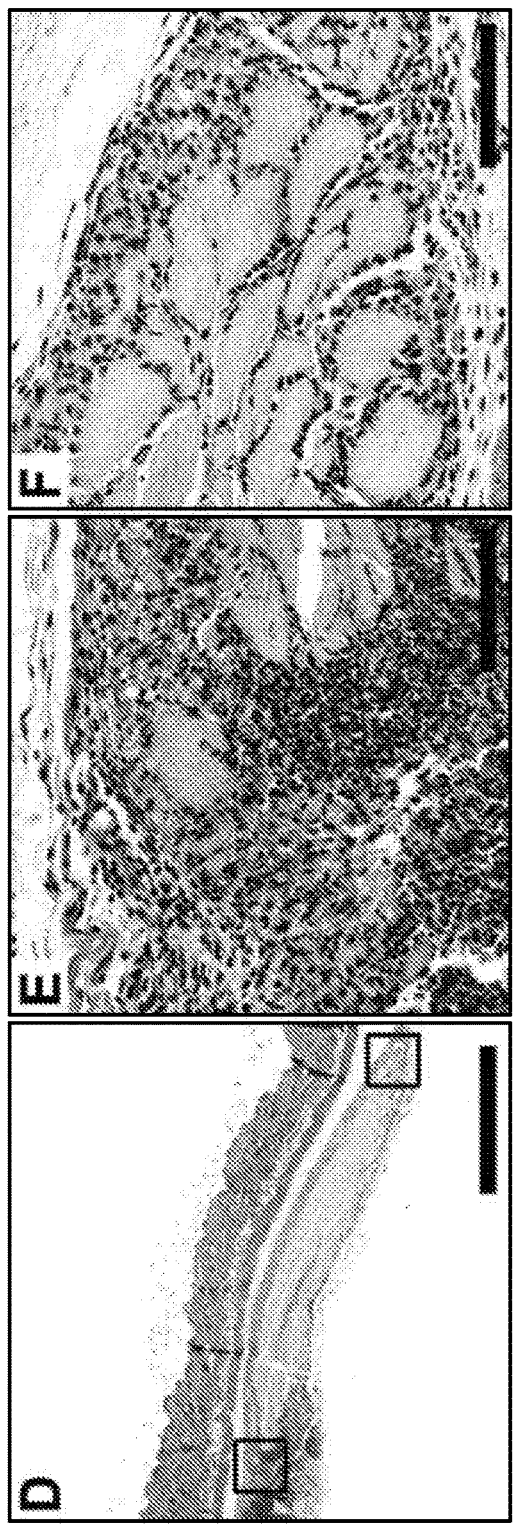
FIG. 15A FIG. 15B FIG. 15C
FIG. 15D FIG. 15E FIG. 15F

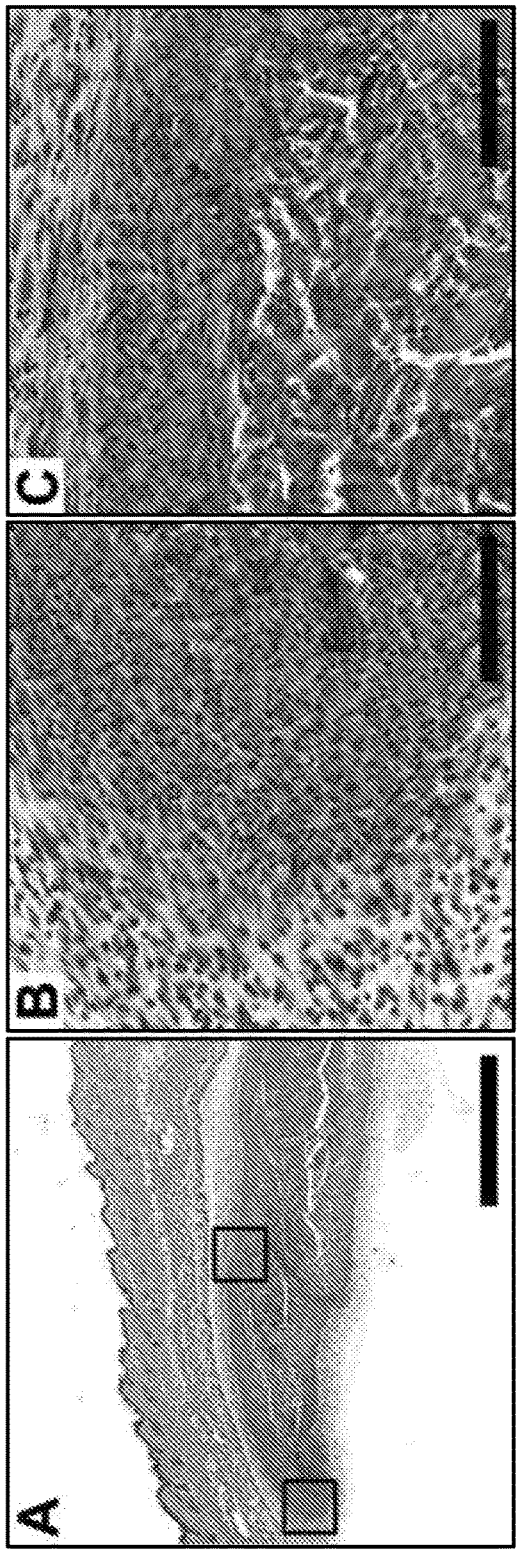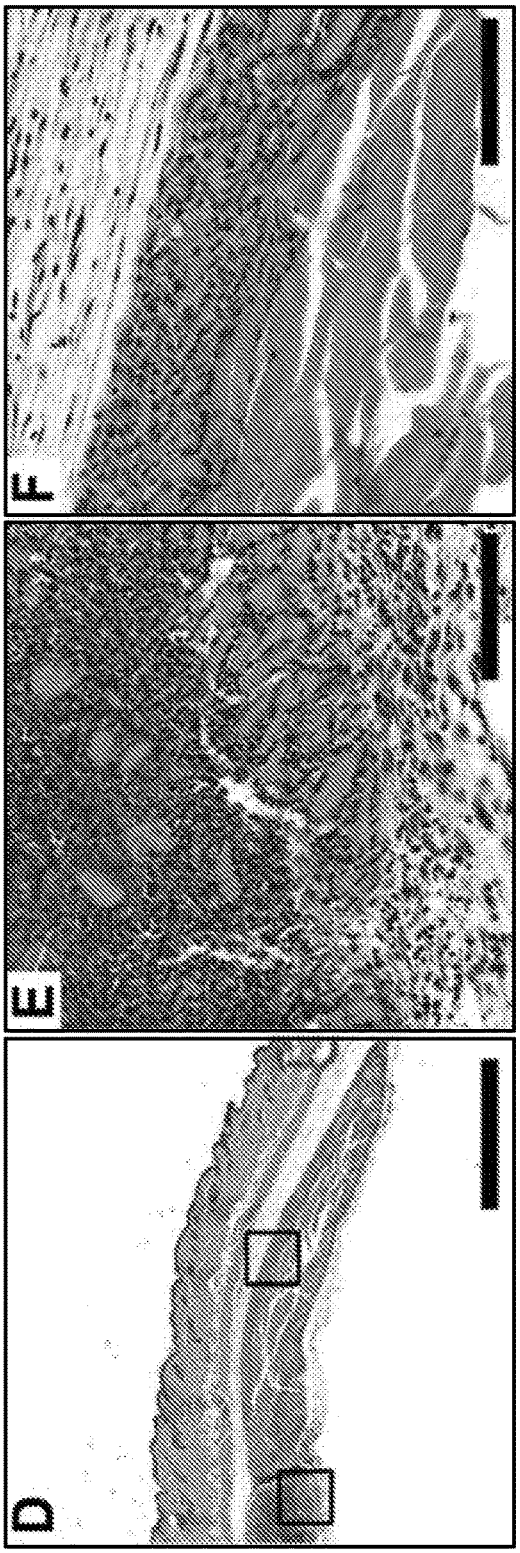

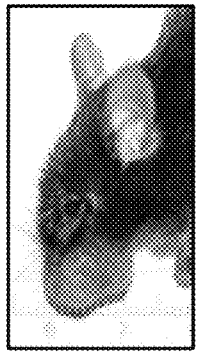
MOC2-E6E7 HBSS 2.jpg
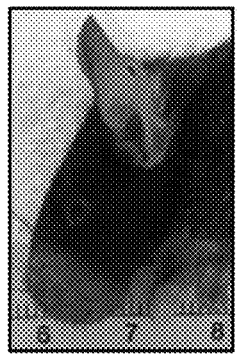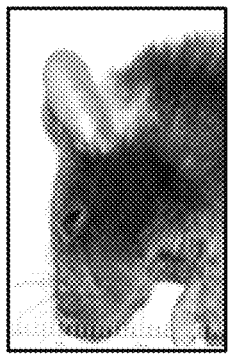
MOC2-E6E7 CDN 10.jpg
MOC2-E6E7 CDN 2.jpg
MOC2-E6E7 CDN 3.jpg
MOC2-E6E7 CDN 7.jpg
MOC2-E6E7 CDN 9.jpg
FIG. 17A

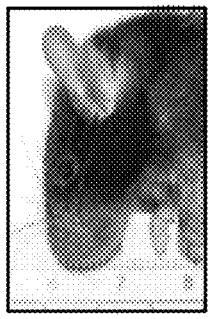 MOC2-E6E7 Collagen Gel 2.jpg
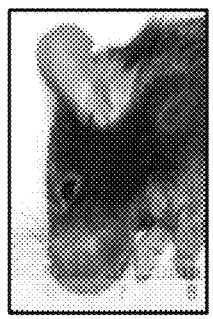 MOC2-E6E7 Collagen Gel...
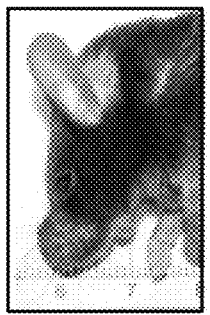 MOC2-E6E7 Collagen Gel...
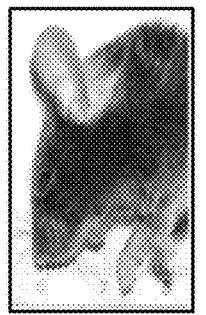 MOC2-E6E7 Collagen Gel...
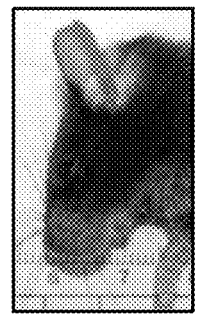 MOC2-E6E7 Collagen Gel...
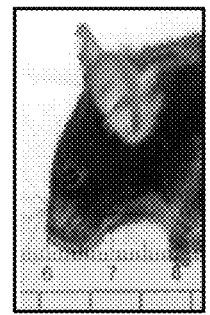 MOC2-E6E7 Collagen Gel...
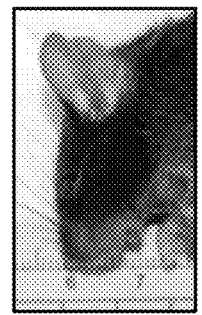 MOC2-E6E7 Collagen Gel...
FIG. 17B

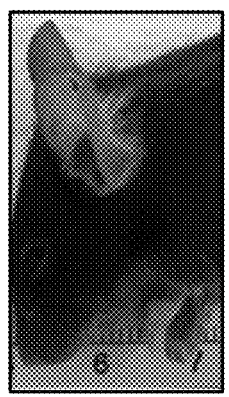
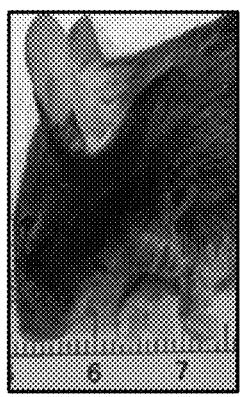
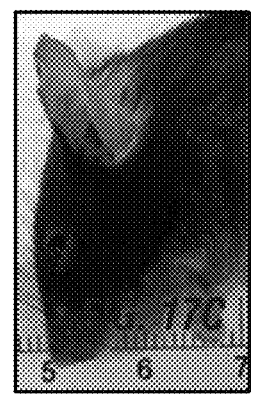
MOC2-E6E7 K2 Gel+CDN...  MOC2-E6E7 K2 Gel+CDN...  MOC2-E6E7 K2 Gel+CDN...
*FIG. 17C (Cont'd)*

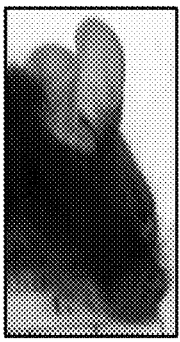
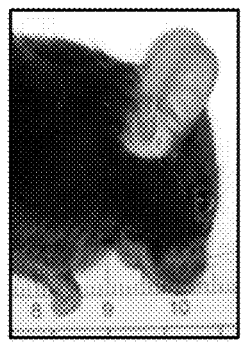
*MOC2-E6E7 CDN 2.jpg*    *MOC2-E6E7 K2 Gel + CDN...*    *MOC2-E6E7 Collagen Gel*
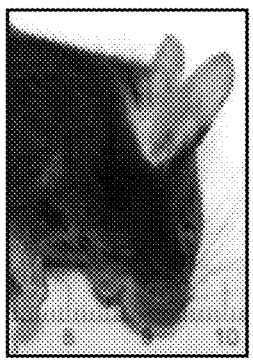
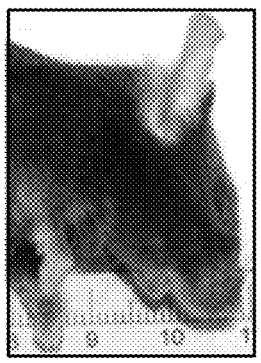
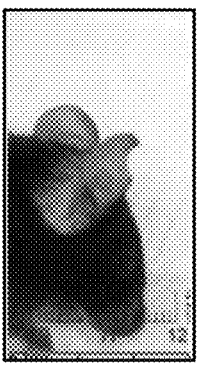
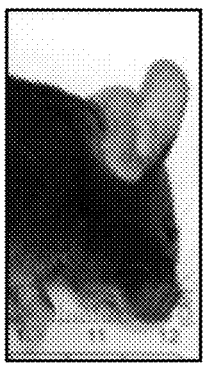
*MOC2-E6E7 K2Gel + CDN...*    *MOC2-E6E7 K2Gel + CDN...*    *MOC2-E6E7 K2Gel + CDN...*    *MOC2-E6E7 K2Gel + CDN...*    *MOC2-E6E7 K2Gel + CDN...*
*FIG. 18*

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Lys Lys Ser Leu Ser Leu Ser Leu Ser Leu Ser Leu Ser Leu Lys Lys
1               5                   10                  15

<210> SEQ ID NO 2
<211> LENGTH: 9
<212> TYPE: PRT
<213> ORGANISM: Homo sapiens

<400> SEQUENCE: 2

Arg Ala His Tyr Asn Ile Val Thr Phe
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Glu Glu Ser Leu Ser Leu Ser Leu Ser Leu Ser Leu Ser Leu Glu Glu
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Arg Arg Ser Leu Ser Leu Ser Leu Ser Leu Ser Leu Ser Leu Arg Arg
1               5                   10                  15
```

HYDROGEL DELIVERY OF STING IMMUNOTHERAPY FOR TREATMENT CANCER

PRIORITY CLAIM

This application is a national phase application under 35 U.S.C. § 371 of International Application No. PCT/US2018/037716 filed on Jun. 15, 2018, and claims benefit of priority to U.S. Provisional Application Ser. No. 62/520,834 filed on Jun. 16, 2017, the entire contents of which are hereby incorporated by reference.

FEDERAL FUNDING DISCLOSURE

This invention was made with government support under grant no. NIH-DE021798 and NIH DE023577 awarded by the National Institutes of Health. The government has certain rights in the invention.

The invention was also funded, in part, by a grant from The Welch Foundation under grant no. C-1557.

REFERENCE TO A SEQUENCE LISTING

Pursuant to 37 C.F.R. 1.821(c), a sequence listing is submitted herewith as an ASCII compliant text file named "RICE.P0027US_ST25", created on Nov. 20, 2023, and having a size of 1,236 bytes. The content of the aforementioned file is hereby incorporated by reference in its entirety.

BACKGROUND

1. Field

This disclosure relates to the fields of chemistry, pharmaceuticals, medicine, and oncology. In particular, compositions multi domain peptide hydrogels and cyclic dinucleotides are disclosed, as well as methods of treating cancer therewith.

2. Related Art

Almost 50,000 men and women in the USA will develop head and neck squamous cell carcinoma (HNSCC) this year. Despite advances in multi-modality therapy including ablative/reconstructive surgery, radiation therapy, and chemotherapy, less than two-thirds of these patients will survive more than five years (SEER Fast Fact Sheets, 2012), and the annual death rate from this disease approximates that of melanoma and endometrial cancer (NCI Surveillance Epidemiology and End Results, 2012). These figures become even more disheartening when one realizes that multimodality therapy can have significant side-effects. Given the well-known limitations and morbidity associated with conventional treatments, new advances are needed for the effective treatment of HNSCC.

Immunotherapy has arisen recently as an exciting treatment for many cancers including melanoma, lung, head and neck, and other types (Margolin, 2016; Modena et al., 2016; Economopolou et al., 2016; Atkins et al., 2016; Ferris et al., 2016; Carolina & Chervin, 2016). In some cases, it has shown the potential to generate specific and durable anti-tumor responses that are associated with lower morbidity and long-term remission, overcoming a major limitation of traditional cancer treatments such as chemo- and radiation therapy. Nonetheless, while "breakthrough immunotherapies" such as immune checkpoint inhibition have recently gained FDA approval as first-line treatment for several kinds of advanced stage cancers (including HNSCC), it is still only effective in 15-20% of patients, with the majority of tumors showing resistance to this approach.

Initial investigations into the mechanisms underlying clinical response versus resistance to immunotherapies in patients has revealed two major subsets of tumor microenvironment (TME) via transcriptional profiling: 1) a "T cell-inflamed" subset with a gene expression signature indicating the presence of T cell transcripts, chemokines involved in T cell recruitment, and a Type 1 interferon transcriptional profile and 2) "non-T cell inflamed" tumors showing a microenvironment lacking in these markers (Harlin et al., 2009). Patients with tumors showing the "T cell-inflamed" phenotype were shown to benefit from immunotherapy, and these findings were confirmed with more recent clinical data (Galon et al., 2012) indicating that the immunophenotype of the TME can affect response to several immunotherapy strategies. Thus, the ability of cells within the TME to produce chemokines and recruit activated T cells is critical for immunotherapy efficacy to be realized, underscoring the importance of developing new strategies to effectively promote an immune-responsive TME.

Studies of the underlying mechanisms which promote spontaneous T cell infiltration of tumors have found that innate immune detection of tumor DNA released into the TME is critical to both spontaneous T cell priming and subsequent infiltration with tumor-infiltrating lymphocytes (TILs) (Fuertes et al., 2011; Corrales et al., 2015). Furthermore, transcriptional profiling of tumors in patients (Harlin et al., 2009) and studies in mice (Diamond et al., 2011) demonstrate that Type 1 interferon (IFN) signaling within the antigen presenting cell (APC) compartment of the TME (particularly CD8$\alpha^+$ dendritic cells) is necessary for tumor-initiated T cell priming. A recently characterized mechanism linking the detection of tumor DNA in APCs with subsequent Type 1 IFN production has been named the stimulator of IFN genes (STING) pathway. The STING receptor is a transmembrane protein localized to the endoplasmic reticulum which can directly bind cyclic dinucleotides, resulting in a downstream signaling cascade involving the production of several Type 1 IFN cytokines, especially IFN-$\beta$ (Burdette and Vance, 2013). STING can be activated by exogenous cyclic dinucleotides produced by bacterial infection or structurally distinct endogenous cyclic dinucleotides produced by host cyclic GMP-AMP synthetase (cGAS) in response to sensing cytosolic double-stranded DNA (dsDNA) (Diner et al., 2013). However, much interest has been focused on the design of synthetic cyclic dinucleotides with improved stability in vivo and the ability to strongly bind and activate both mouse and human STING.

The rationally-designed synthetic Cyclic DiNucleotide dithio-($R_P,R_P$)-[cyclic[A(2',5')pA(3',5')p]] (herein referred to as CDN) is one such promising candidate molecule that is currently in Phase I clinical trials (NCT02675439) and has shown efficacy when injected into murine models of melanoma, colon, and mammary carcinomas However, CDN has shown only limited efficacy in T cell-inflamed preclinical models of certain cancers (e.g., head and neck cancer), requiring concomitant PD-1 immune checkpoint blockade, and it is completely ineffective in non-T cell-inflamed head and neck tumors (Moore et al., 2016a). While STING agonists such as CDN are promising candidates to stimulate innate immunity against some tumors, their effectiveness in HNSCC is limited, indicating that novel approaches to improve the efficacy of CDN in challenging, treatment-refractory HNSCC tumors is warranted. For example, nanoparticulate (PEGylated lipid nanoparticles) and liposomal delivery are being employed in an effort to increase the immune inductive properties of CDNs (Hanson et al., 2014; Miyabe et al., 2014). Further improvements are, however, needed.

SUMMARY

Thus, in accordance with the present disclosure, there is provided a composition comprising (a) a multi domain peptide (MDP) hydrogel and (b) a cyclic dinucleotide (CDN). The CDN may be a natural endogenous CDN, such as produced by cGAS, or a synthetic CDN, such as CDN analog. CDN analogs may comprise a modified base or non-natural internucleoside linkage. CDNs may be selected from dithio-($R_P,R_P$)-[cyclic[A(2',5')pA(3',5')p]], 2'2'-cGAMP, 2'3'-cGAMP, 3'3'-cGAMP, c-di-AMP, 2'3'-c-di-AMP, 2'3'-c-di-AM(PS)2, c-di-GMP, c-di-UMP, c-di-IMP. The peptides of the MDP hydrogel maybe 18-30 residues in length, may have about a 3:1 ratio of hydrophilic to hydrophobic charged residues, may contain a bio-mimetic sequence, and/or may comprise a degradable sequence containing a tumor specific peptide. The MDP hydrogel and the CDN may be covalently or non-covalently bound to each other.

The compositions may be formulated for administration orally, intraadiposally, intraarticularly, intracranially, intradermally, intramuscularly, intranasally, intraocularly, intrapericardially, intraperitoneally, intrapleurally, intraprostatically, intrarectally, intrathecally, intratracheally, intratumorally, intraumbilically, intravaginally, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via local delivery, or via localized perfusion. In some embodiments, the pharmaceutical compositions are formulated for oral administration or topical administration. In some embodiments, the pharmaceutical compositions are formulated as a unit dose.

A method of treating cancer in a patient comprising administering to the patient a therapeutically effective amount of a composition as defined above. The cancer may be a carcinoma, sarcoma, lymphoma, leukemia, melanoma, mesothelioma, multiple myeloma, or seminoma. The cancer may be one of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In particular, the cancer may be head and neck cancer, such as a squamous cell carcinoma The cancer maybe a treatment resistant cancer, a primary cancer, a recurrent cancer, a metastatic cancer and/or a non-T cell inflamed cancer.

The method may further comprise administering a second cancer therapy, such as a chemotherapeutic agent, gene therapy, surgery, a radiotherapy, or an immunotherapy. The patient may be a mammal, such as a human, or a non-human mammal The method may comprises administering the composition once, or two or more times. Administering may comprise intratumoral administration, administration to the tumor bed, or administration regional to the tumor. The second cancer therapy may be surgery, and administering comprises treating a resected tumor bed with said composition. An effective amount of the CDN may be about 20-200 µg, which may be dosed in about 5-200 µl of MDP hydrogel.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

(FIG. 1A) Scheme showing the bi-layered beta-sheet structure of the nanofiber created upon peptide self-assembly. (FIG. 1B) SEM image of nanofibrous hydrogel. Inset shows the clear, shape persistent gel formed upon addition of buffer.

(FIG. 2A) Tumor growth curves showing delayed growth of MOC-2-E6E7 tumors (bottom line) vs. MOC2 (and pBABE-PURO empty vector control). (FIG. 2B) Differences in tumor growth rate between MOC2 and MOC-2-E6E7 are eliminated in B- and T-cell deficient Rag1 knockout mice. (FIG. 2C) Multiplex immunohistochemistry micrograph of MOC-2-E6E7 tumor at Day 29 showing robust CD8+ cell infiltrate (green) throughout the tumor (yellow). (FIG. 2D) MOC-2-E6E7 is resistant to multiple modalities of immunotherapy. Treatment schedule-MSR given on day 3 post-tumor inoculation. CPI is given on days 3, 6, and 9 post-tumor inoculation. Kaplan-Meier survival curves show enhanced survival time (p<0.05 by log rank test) when MSR was combined with CPI, although no animals survived long-term. Best survival seen with MSR+αPD1+αCTLA4 (FIG. 2E) Kaplan-Meier curves showing intratumoral injection of STINGel significantly increases survival in a durable manner Animals were re-challenged with tumor at Day 105 and remained tumor-free at Day 140. Best survival seen with Gel+CDN. Abbreviations: CDN=cyclic dinucleotide STING agonist, Gel=MDP hydrogel, HBSS=Hanks Balanced Salt Solution, CPI=checkpoint inhibitor, MSR=mesoporous silica rod vaccine.

(FIG. 3A) Release profiles of MDP gels. Collagen shows the most rapid, uncontrolled release while Arg-MDP shows the slowest, most prolonged release. Glu- and Lys-MDP show intermediate release rates (panel inset lists conditions top to bottom same as shown in graph). (FIG. 3B) Flow cytometry shows a substantial population of CD45$^+$/CD11b$^+$/CD11c$^+$ dendritic cells recruited to the Lys- MDP in vivo. (FIG. 3C-E) substantial MOC-2-E6E7 proliferation (green cells) & minimal cell death (red cells) in vitro in Lys-MDP.

(FIG. 4C) Model of anti-parallel β-sheet nanofiber formed by the MDP in solution. The red arrow indicates the axis of the nanofiber and orientation of hydrogen bonding. (FIG. 4D) Scanning Electron Microscopy image of the MDP gel showing a wide field image of the self-assembled nanofibers.

(FIG. 5A) CDN drug release kinetics profiles of MDP hydrogels (closed circles) compared to collagen control hydrogels (open circles). Samples are 30 μL gels in 96 well plates, loaded with 910 μM CDN and placed under 200 μL HBSS. Absorbance was measured at 259 nm and converted to total percent released for 24 h to monitor release rate and time until equilibrium. Values represent the mean and standard deviation in all plots (n=3). (FIG. 5B) Same as FIG. 5A, but including two additional MDPs: $E_2(SL)_6E_2$ (SEQ ID NO: 3) and $R_2(SL)_6R_2$ (SEQ ID NO: 4). Both show better (slower) release compared to collagen, while $R_2(SL)_6R_2$ (SEQ ID NO: 4) is the best of the group.

(FIG. 6A) Unloaded hydrogel control showing cell viability over time from small clumps into large spreading masses throughout the peptide hydrogel. (FIG. 6B) CDN dose response assays with images shown from day 3 time point, at which time cells had either died or survived past the initial stage of exposure to CDN. All scale bars are 50 μm, and z-stacks are 100 μm in thickness.

FIGS. 8A-F. Masson's trichrome stained MDP hydrogel implants unloaded and loaded with CDN, injected subcutaneously in the dorsal flank of mice. Time point shown is 3 days post injection, at which time hydrogel implant was removed and processed for histology. Scale bars in FIGS. 8A and 8D=1 mm; scale bars in FIGS. 8B, 8C, 8E, and 8F=0.1 mm (FIGS. 8A-C) MDP unloaded control implant at 4× magnification showing even infiltration of cells, with boxes drawn around chosen areas whose 40× counterparts are shown in FIGS. 8B and 8C, respectively. (FIGS. 8D-F) MDP implant loaded with 910 μM CDN (STINGel) at 4× magnification showing uneven infiltration of cells across the implant. Boxes drawn around chosen areas in FIG. 8D again have 40× counterparts shown in FIGS. 8E and 8F, respectively.

(FIG. 9A) Median primary tumor growth for each group, showing significantly smaller median tumor size in CDN treated groups and a complete delayed growth in STINGel (MDP+CDN) C57BL/6 mice. (FIGS. 9B-G) Individual tumor size growth data for tumor bearing mice in each group (number of tumor bearing mice above each plot), showing a clear improvement in progressive tumor free survival for the STINGel treated mice relative to controls and collagen+CDN. (FIG. 9B) HBSS, (FIG. 9C) CDN-alone, (FIG. 9D) MDP gel, (FIG. 9E) collagen gel, (FIG. 9F) collagen+CDN, (FIG. 9G) STINGel.

(FIG. 10A) Survival of the different experimental groups based on euthanasia timepoints resulting from excessive tumor burden. The total experimental period was 140 days post-tumor cell inoculation. The 3(IJ) on the x-axis refers to timepoint for intratumoral injection, and 105(RC) refers to timepoint for survivor rechallenge. Whereas 60% of the STINGel-treated C57BL/6 mice survived until the endpoint of the study, nearly all control group (HBSS, MDP gel, and collagen gel) mice were euthanized prior to reaching the endpoint due to excessive tumor burden. Only 10% of CDN alone and collagen+CDN treated mice survived (lines overlaid on plot). *p<0.0282 vs. CDN, **p<0.0064 vs. MDP gel, #p<0.0498 vs. Collagen+CDN. (FIG. 10B) Representative image of STINGel treated mouse that maintained tumor clearance at day 37. (FIG. 10C) Representative image of CDN-only treated mouse growing tumor at day 37.

(FIG. 13A) Percent cell viability per mm3 of hydrogel over days 1-7 with increasing concentrations of CDN. No CDN, 5 μM, 57 μM and 114 μM equivalent at Day 7; 228 μM shows reduced cell viability at Day 7; 455 μm and 910 μM show no cell viability at Day 7. (FIG. 13B) Dose response curve (day 3 timepoint) used to assess CDN toxicity to MOC2-E6E7 cells, showing percent viable cells per mm3 of hydrogel at tested doses.

(FIGS. 14D-F) MDP hydrogel implant loaded with 910 μM CDN (STINGel) at 4× magnification showing uneven infiltration of cells across the implant. Boxes drawn around relevant areas in panel D again have 40× counterparts shown in FIGS. 14E and 14F, respectively.

FIGS. 15A-F. Masson's trichrome stained MDP peptide hydrogel implant unloaded and loaded with CDN, injected subcutaneously in mice. Time point shown is 7 days post injection, at which time hydrogel implant was removed and processed for histology. 4× scale bars in FIGS. 15A and 15D are 1 mm; 40× scale bars in FIGS. 15B, 15C, 15E, and 15F are 0.1 mm (FIGS. 15A-C) MDP control implant at 4× magnification showing even infiltration of cells, with boxes drawn around relevant areas whose 40× counterparts are shown in FIGS. 15B and 15C, respectively. (FIGS. 15D-F) $K_2(SL)_6K_2$ (SEQ ID NO: 1) hydrogel implant loaded with 910 μM CDN (STINGel) at 4× magnification showing uneven infiltration of cells across the implant even at day 7 post injection. Boxes drawn around relevant areas in FIG. 15D again have 40× counterparts shown in FIGS. 15E and 15F, respectively.

FIGS. 16A-F. H&E stained MDP peptide hydrogel implant unloaded and loaded with CDN, injected subcutaneously in mice. Time point shown is 7 days post injection, at which time hydrogel implant was removed and processed for histology. 4× scale bars in FIGS. 16A and 16D are 1 mm; 40× scale bars in FIGS. 16B, 16C, 16E, and 16F are 0.1 mm (FIGS. 16A-C) MDP control implant at 4× magnification showing even infiltration of cells, with boxes drawn around relevant areas whose 40× counterparts are shown in FIGS. 16B and 16C, respectively. (FIGS. 16D-F) MDP hydrogel implant loaded with 910 μM CDN (STINGel) at 4× magnification showing uneven infiltration of cells across the implant even at day 7 post injection. Boxes drawn around relevant areas in FIG. 16D again have 40× counterparts shown in FIGS. 16E and 16F, respectively.

FIGS. 17A-C. Representative time point midway through in vivo survival experiment, showing all groups at day 37 post inoculation with MOC2-E6E7 tumor cells. All surviving mice from each group (n=10) are shown (whether growing tumors or not). (FIG. 17A) HBSS control group and CDN alone treatment group. (FIG. 17B) Collagen control group and collagen+CDN treatment group. (FIG. 17C) MDP control group and STINGel treatment group.

FIG. 18. Day 105 time point near the end of the in vivo survival experiment (n=10 for each group), showing all mice that survived the initial test and were rechallenged on day 105 with a secondary inoculation of MOC2-E6E7 tumor cells on the opposite cheek (thus mice are pictured facing the opposite direction to show relevant side). All mice pictured here showed acquired immunity, surviving rechallenge with no tumor growth to day 140 when the study was concluded. No mice from controls (HBSS, MDP gel, or collagen gel) survived to this point.

DESCRIPTION OF ILLUSTRATIVE EMBODIMENTS

Figure 4B:
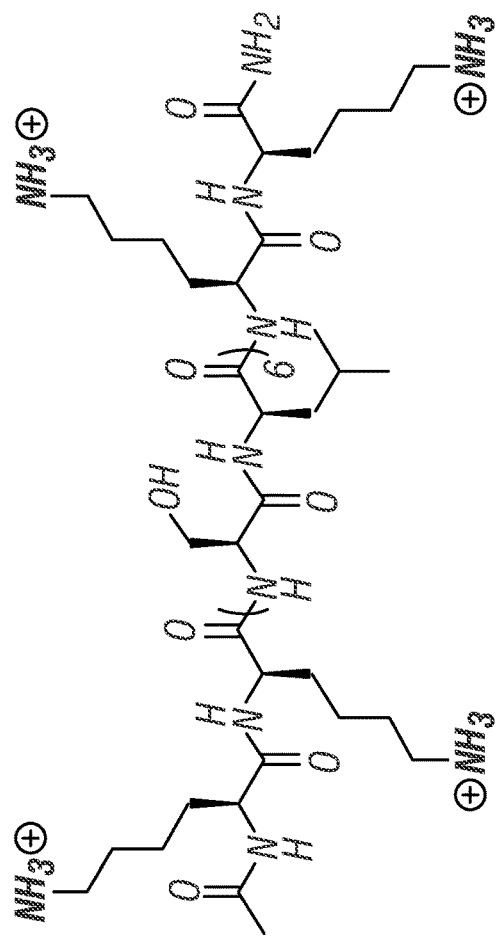
FIGS. 4A-D. Chemical structures of (FIG. 4A) ML RR-S2 CDA synthetic STING agonist (CDN), (FIG. 4B) $K_2(SL)_6K_2$ (SEQ ID NO: 1) multidomain peptide (MDP), showing charge-pair complementarity of positive lysine termini and negative thiophosphate linkages.
Figure 4A:
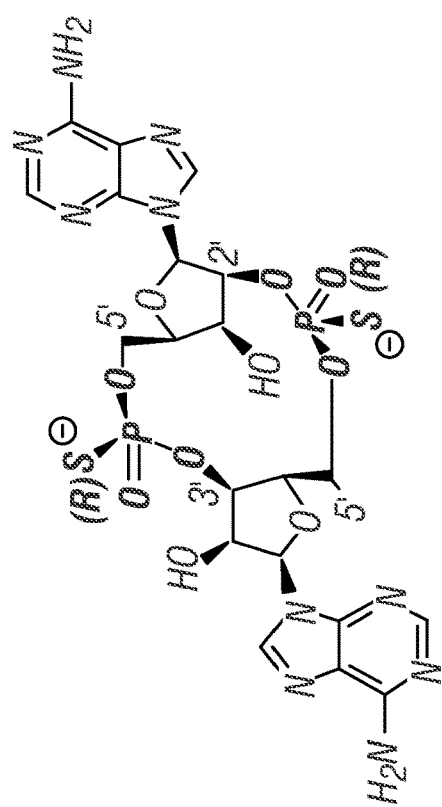
Figure 4D:
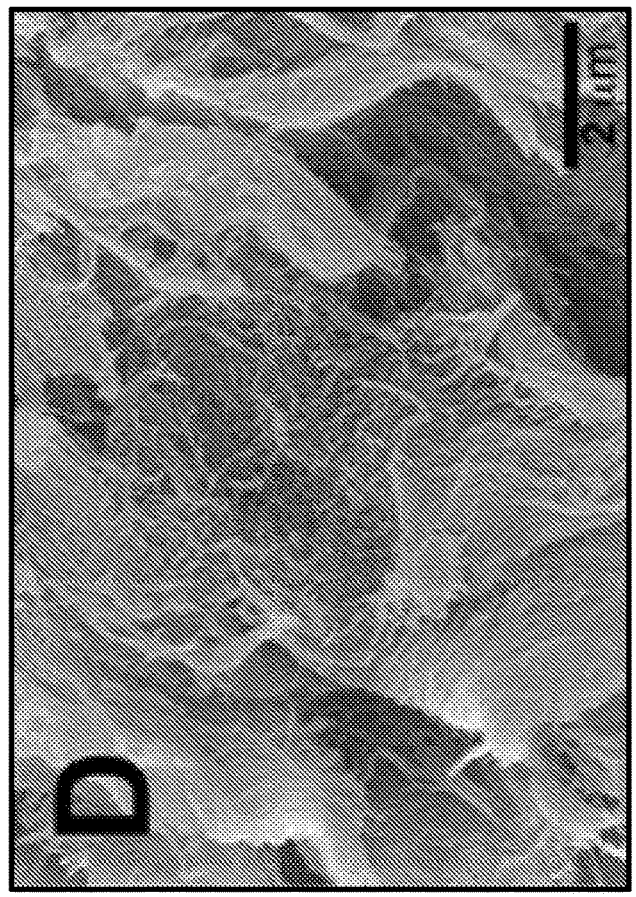
Figure 4C:
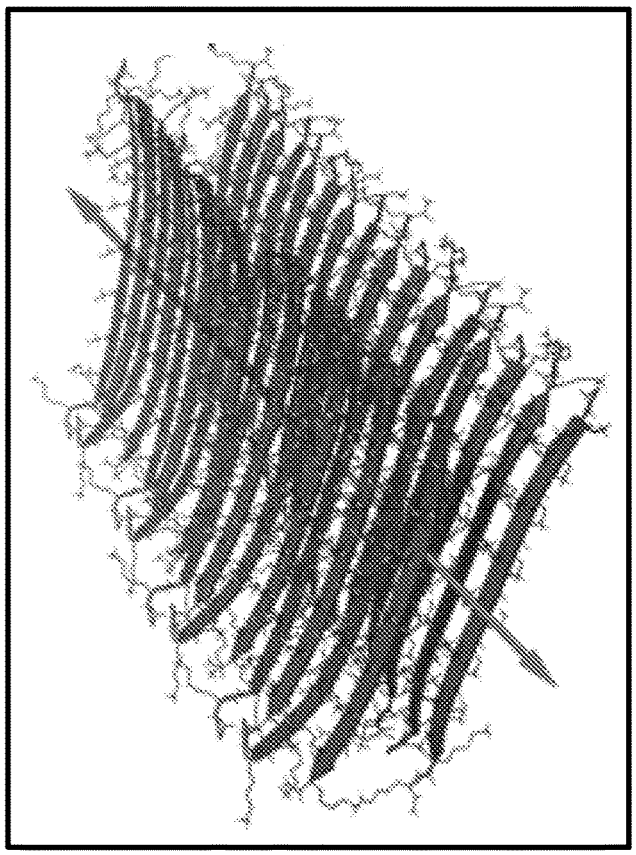

As discussed above, a novel class of immunotherapeutics based on synthetic cyclic dinucleotides (CDNs) has recently been found to induce strong anti-tumor responses in preclinical models through the Stimulator of Interferon Genes (STING) pathway (Corrales et al., 2015; Barber, 2015; Gadkaree et al., 2017). The STING pathway has emerged as a key mechanism linking the detection of cytosolic tumor DNA to downstream activation of innate immune cells (Burdette et al., 2011; Cerboni et al., 2017). The rationally-designed synthetic Cyclic Dinucleotide dithio-$(R_P,R_P)$-[cyclic[A(2',5')pA(3',5')p]] (abbreviated as ML RR-S2 CDA or just CDN, see FIG. 4A) is a promising candidate molecule in clinical trials (see NCT02675439) that has shown efficacy in murine cancer models, promoting the specific rejection of several types of tumors (Corrales et al., 2015). However, to date CDN monotherapy has shown poor efficacy in preclinical models of HNSCC, requiring multiple injections and concomitant administration of immune checkpoint antibodies (AduroBiotech, 2016; Moore et al., 2016). Current clinical trials are evaluating intratumoral injections of CDN as monotherapy, a strategy that may prove to be insufficient (AduraBiotech, 2016). Thus, novel approaches to improve the efficacy of CDN in challenging, treatment-refractory tumor models are warranted.

In response to this challenge, the inventors developed a novel peptide hydrogel-based platform for intratumoral CDN delivery, which they call "STINGel." This localizable drug delivery vehicle, utilizing the power of immunotherapy, is based on prior work in the inventors' laboratory studying the utility of multidomain peptides (MDPs) as unique supramolecular biomaterials. These self-assembling peptides mimic the extracellular matrix of cells through the formation of a nanofibrous network, and can act as biofunctional delivery platforms that allow for an immense diversity of functionality to be introduced (Moore et al., 2017; Aulisa et al., 2009). These and other aspects of the disclosure are set out below.

I. STING AND STING AGONISTS

A. STING

Stimulator of interferon genes (STING), also known as transmembrane protein 173 (TMEM173) and MPYS/MITA/ERIS is a protein that in humans is encoded by the TMEM173 gene. STING plays an important role in innate immunity. STING induces type I interferon production when cells are infected with intracellular pathogens, such as viruses, mycobacteria and intracellular parasites. Type I interferon, mediated by STING, protects infected cells and nearby cells from local infection by binding to the same cell that secretes it (autocrine signaling) and nearby cells (paracrine signaling.)

STING is encoded by the TMEM173 gene. It works as both a direct cytosolic DNA sensor (CDS) and an adaptor protein in Type I interferon signaling through different molecular mechanisms. It has been shown to activate downstream transcription factors STATE and IRF3 through TBK1, which are responsible for antiviral response and innate immune response against intracellular pathogen.

Amino acids 1-379 of human STING include the 4 transmembrane regions (TMs) and a C-terminal domain. The C-terminal domain (CTD amino acids 138-379) contains the dimerization domain (DD) and the carboxy-terminal tail (CTT amino acids 340-379). The STING forms a symmetrical dimer in the cell. STING dimer resembles a butterfly, with a deep cleft between the two protomers. The hydrophobic residues from each STING protomer form hydrophobic interactions between each other at the interface.

STING is expressed in hematopoietic cells in peripheral lymphoid tissues, including T lymphocytes, NK cells, myeloid cells and monocytes. It has also been shown that STING is highly expressed in lung, ovary, heart, smooth muscle, retina, bone marrow and vagina. The subcellular localization of STING has been elucidated as an endoplasmic reticulum protein. Also, it is likely that STING associates in close proximity with mitochondria associated ER membrane (MAM)—the interface between the mitochondrion and the ER. During intracellular infection, STING is able to relocalize from endoplasmic reticulum to perinuclear vesicles potentially involved in exocyst mediated transport. STING has also been shown to colocalize with autophagy proteins, microtubule-associated protein 1 light chain 3 (LC3) and autophagy-related protein 9A, after double-stranded DNA stimulation, suggesting its presence in the autophagosome.

STING mediates the type I interferon production in response to intracellular DNA and a variety of intracellular pathogens, including viruses, intracellular bacteria and intracellular parasites. Upon infection, STING from infected cells can sense the presence of nucleic acids from intracellular pathogens, and then induce interferon β and more than 10 forms of interferon α production. Type I interferon produced by infected cells can find and bind to Interferon-alpha/beta receptor of nearby cells to protect cells from local infection.

STING elicits powerful type I interferon immunity against viral infection. After viral entry, viral nucleic acids will be present in the cytosol of infected cells. Several DNA sensors, such as DAI, RNA polymerase III, IFI16, DDX41 and cGAS, can detect foreign nucleic acids. After recognizing viral DNA, DNA sensors initiate the downstream signaling pathways by activating STING-mediated interferon response. Adenovirus, herpes simplex virus (HSV-1 and HSV-2), as well as negative-stranded RNA virus-vesicular stomatitis virus (VSV) have been shown to be able to activate a STING-dependent innate immune response.

Intracellular bacteria, *Listeria monocytogenes*, have been shown to stimulate host immune response through STING. STING may play an important role in the production of MCP-1 and CCL7 chemokines. STING deficient monocytes are intrinsically defective in migration to the liver during *Listeria monocytogenes* infection. In this way, STING protects host from *Listeria monocytogenes* infection by regulating monocyte migration. The activation of STING is likely to be mediated by cyclic-di-AMP secreted by intracellular bacteria. STING may be an important molecule for protective immunity against infectious organisms. For example, animals that cannot express STING are more susceptible to infection from VSV, HSV-1 and *Listeria monocytogenes*, suggesting its potential correlation to human infectious diseases.

STING mediates type I interferon immune response by functioning as both a direct DNA sensor and a signaling adaptor protein. Upon activation, STING stimulates TBK1 activity to phosphorylate IRF3 or STATE. Phosphorylated IRF3s and STAT6s dimerize, and then enter nucleus to stimulate expression of genes involved in host immune response, such as IFNB, CCL2, CCL20, etc.

Several reports suggested that STING is associated with the activation of selective autophagy. *Mycobacterium tuberculosis* has been shown to produce cytosolic DNA ligands which activate STING, resulting in ubiquitination of bacteria and the subsequent recruitment of autophagy related proteins, all of which are required for 'selective' autophagic targeting and innate defense against *M. tuberculosis*.

In summary, STING coordinates multiple immune responses to infection, including the induction of interferons and STATE-dependent response and selective autophagy response.

Cyclic dinucleotides-second-messenger signaling molecules produced by diverse bacterial species were detected in the cytosol of mammalian cells during intracellular pathogen infection; this leads to activation of TBK1-IRF3 and the downstream production of type I interferon. STING has been shown to bind directly to cyclic di-GMP, and this recognition leads to the production of cytokines, such as type I interferon, that are essential for successful pathogen elimination.

DDX41, a member of the DEXDc family of helicases, in myeloid dendritic cells recognizes intracellular DNA and mediates innate immune response through direct association with STING. Other DNA sensors-DAI, RNA polymerase III, IFI16, have also been shown to activate STING through direct or indirect interactions.

Cyclic GMP-AMP synthase (cGAS), which belongs to the nucleotidyltransferase family, is able to recognize cytosolic DNA contents and induce STING-dependent interferon response by producing secondary messenger cyclic guanosine monophosphate-adenosine monophosphate (cyclic GMP-AMP, or cGAMP). After cyclic GMP-AMP bound STING is activated, it enhances TBK1's activity to phosphorylate IRF3 and STATE for downstream type I interferon response.

It has been proposed that intracellular calcium plays an important role in the response of the STING pathway.

B. STING Agonists

Cyclic dinucleotides (CDNs) have been described as having immunomodulatory properties that could be exploited in an immunotherapy treatment. This immunomodulatory activity is typically the induction of cytokines and/or activation of immune cells in vitro or in vivo. Related U.S. Pat. Nos. 7,569,555 B2 and 7,592,326 B2, incorporated herein by reference, refer to administration of c-diGMP or functionally equivalent analogs thereof as a "method of stimulating and/or modulating the immune and inflammatory response." They suggest that these compounds could be used to prevent or treat allergic reactions, or as vaccine adjuvants. They demonstrate that c-diGMP induces diverse cytokines, including chemokines, in cell lines in vitro, and can be used together with an antigen to activate dendritic cells in vitro. U.S. Patent Publication 2008/0286296 A1 incorporated herein reference, refers to the use of c-diGMP, c-diAMP and 3',3' cyclic dinucleotide analogs thereof as "adjuvants or and/or immunomodulators for prophylactic and/or therapeutic vaccination" for a wide range of indications. The authors reported that c-diGMP stimulates murine DC cells to produce CD40 in vitro. Moreover, in diverse experiments on murine models of immunization (using β-galactosidase as antigen), the authors show that mice treated with c-diGMP or c-diAMP post-immunization produce greater amounts of various cytokines, and/or IgG, and/or anti-P-Gal antibodies than do mice that do not receive any cyclic dinucleotide. U.S. Patent Publication 2014/0205653 A1 incorporated herein by reference, and the related WIPO patent application WO2014/093936 A1, incorporated herein by reference, encompass the synthesis, and immunomodulation activity screening, of stereochemically-defined 3',3' cyclic dinucleotides, including phosphorothioate (also known as "P(S)" or "thiophosphate") analogs. They report that representative compounds of their invention induce IFN-β in vitro in two cell lines: THP-1 human monocytes and DC2.4 cells. Furthermore, they describe the efficacy of some of these compounds in murine models of immunization in which SIV gag protein or OVA were used as antigen. Specifically, they report that SIV-gag-immunized mice treated with (Rp,Rp)dithio-diphosphate c-diGMP exhibit better SIV-gag-specific CD8 T cell memory than do controls treated with saline, and that OVA-immunized mice treated with (Rp,Rp)dithio-diphosphate c-diGMP exhibit better OVA-specific CD8 T cell memory than do those treated with the reference compound c-diGMP.

Romling & Amikam (2006) suggested that the effects of c-diGMP in eukaryotes might be exploited for cancer treatment, while the group of Karaolis reported that c-diGMP inhibited the growth of human colon cancer (H508) cells in vitro, suggesting that cyclic dinucleotides could be used as therapeutic agents for cancer treatment or prevention (Karaolis, 2005; U.S. Pat. No. 7,709,458 B2).

Dubensky and colleagues have published an extensive review of STING agonist cyclic dinucleotides used as adjuvants, outlining work by their group and those of others. Depending on the experiment cited, all the disclosed compounds (c-diGMP, c-diAMP, c-diIMP and related analogs, including 2',3' and 3',3' compounds) induced production of various cytokines (e.g., Type I interferons, TNF-α, IL-2, etc.) either in vitro or in vivo (in healthy animals or in animal models of disease) (Dubensky et al., 2013). The type and extent of immunomodulation by cyclic dinucleotides is partially dictated by the cells on which they act.

Miyabe et al. (2014) demonstrated the efficacy of a combination therapy of c-diGMP plus OVA in mice that received different immunization treatments followed by subcutaneous injection of E.G7-OVA tumors. Mice that received different immunization treatments followed by subcutaneous injection of E.G7-OVA tumors. Mice that had been immunized with a combination of c-diGMP, OVA and liposomal carrier showed drastically and significantly smaller tumor volumes than did mice treated with PBS alone, OVA alone, OVA plus c-diGMP, or OVA plus the liposomal carrier. The authors attributed the efficacy of the combination therapy to induction of IFN-β by c-diGMP through the STING-TBK1-IRF3 pathway. Interestingly, Chandra et al. (2014) have reported that when mice with breast cancer metastases were immunized with a *Listeria monocytogenes* (LM)-based vaccine and subsequently treated with the STING agonist c-diGMP, the metastases almost completely disappeared. Ohkuri and colleagues studied the activity of Type I IFNs in the microenvironment of glioma, finding that STING is partially responsible for local production of these cytokines (Ohkuri et al., 2014). They then tested c-diGMP immunotherapy as primary treatment in a murine model of glioma, reporting that mice that had received c-diGMP by intra-tumoral injection exhibited longer survival, more of certain therapeutically beneficial T cells (CD4+ and CD8+ and CD11c+), and greater expression of certain cytokine genes (including CC15 and CxcllO) than did mice that had received only solvent (Ohkuri et al., 2014). They also showed that c-diGMP inhibited tumor growth in a murine model of de novo glioma. The authors affirmed that under these conditions, c-diGMP enhances recruitment of T cells to the tumor site. Finally, they evaluated c-diGMP as an adjuvant for antigen-specific vaccination of glioma in a murine model of glioma that expresses OVA257-264 as tumor antigen. They reported that although c-diGMP monotherapy provided longer survival than did vaccine alone or negative control (using mock treatment), the longest survival was observed in mice treated with a combination of c-diGMP and anti-OVA257-264 vaccine. In both the primary treatment and the adjuvant studies, the authors observed beneficial effects of c-diGMP-treatment in brain-infiltrating leukocytes (BILs) obtained from each type of treated mouse.

There are very few literature reports of combination therapies that entail use of cyclic dinucleotides. The related patent applications U.S. Patent Publication 2014/0205653 A1 and WO2013/185052 A1, both incorporated herein by reference, report the use of cyclic dinucleotide STING agonists, including prodrugs thereof, in combination with the cancer vaccine GVAX (inactivated tumor cells stimulated to release the cytokine GM-CSF). The authors demonstrate that a combination therapy comprising use of Rp, Rp dithio c-diAMP and GVAX provides greater inhibition of tumor growth in a murine model of TRAMP-C2 subcutaneous tumors than do GVAX monotherapy or the combination of c-diAMP and GVAX.

Examples of cyclic dinucleotides include c-AIMP, (3',2') c-AIMP, (2',2')c-AIMP, (2',3')c-AIMP, c-AIMP(S), c-(dAMP-d1MP), c-(dAMP-2'FdIMP), c-(2'FdAMP-2'FdIMP), (2',3')c-(AMP-2'FdIMP), c-[2'FdAMP(S)-2'FdIMP(S)] and c-[2'FdAMP(S)-2'FdIMP(S)](POM)$_2$ or a pharmaceutically acceptable salt or prodrug thereof. Particularly, the cyclic dinucleotide is selected from the group consisting of: c-AIMP, c-(2'FdAMP-2'FdIMP), c-AIMP(S), c-[2'FdAMP(S)-2'FdIMP(S)] and c-[2'FdAMP(S)-2'FdIMP(S)](POM)$_2$.

Cyclic dinucleotides do not resemble typical small-molecule drug candidates: their molecular weight is ~700 Da, they have two negative charges, and they are built from potentially labile phosphodiester linkages. Nevertheless, they are able to activate the STING pathway, presumably after entering the cell by presently unknown mechanisms. Unlike in many of the previously cited reports on cyclic dinucleotides (see, for example: Ablasser et al., 2013; Downey, Aghaei, Schwendener & Jirik, 2014; Miyabe et al., 2014), there is no need to permeabilize cultured recipient cells (e.g., by using compounds such as digitonine) to favor uptake of CDNs.

Since STING is located in the endoplasmic reticulum and detects cyclic dinucleotides in the cytoplasm, any STING agonist destined for therapeutic use must be able to penetrate into cells. Furthermore, greater cellular uptake of a compound translates to higher bioavailability, which is a desirable property for clinical use.

Cyclic dinucleotides are enzymatically degraded by nucleases and/or phosphodiesterases and therefore, when used as therapeutic agents, these compounds can suffer from diminished half-life. Advantageously, inclusion of phosphorothioate internucleotide linkages enable maximal half-life, and possibly higher activity, in vivo. The use of such linkages is a known strategy to circumvent enzymatic hydrolysis (see, for example: U.S. Patent 2014/0205653 A1; incorporated herein by reference). The phosphorothioate linkage introduces an additional chiral center on the phosphorus atom, which yields a diastereoisomer pair ([Rp] and [Sp]) at each phosphorothioate linkage. CDNs may be administered as a pharmaceutical formulation(s) in a therapeutically effective amount by any of the accepted modes of administration, in particular by intravenous or intratumoral route.

II. MULTI DOMAIN PEPTIDE HYDROGELS

Multidomain peptides (MDPs) are a class of self-assembling peptides that are organized in a β-sheet motif, resulting in a nanofibrous architecture. This structure is stabilized by hydrophobic packing in the fiber core and a hydrogenbonding network down the fiber long axis. Under easily controllable conditions, regulated by electrostatic interactions between the peptides and the pH and salt composition of the solvent, the nanofiber length can be dramatically extended, resulting in fiber entanglement and hydrogel formation.

One of the chief strengths of this supramolecular material is that the design criteria governing its structure and assembly are robust and permit a wide range of modifications without disruption. This allows the MDPs to be tailored to suit a wide range of applications, particularly in biomedical engineering. For example, delivery of small molecules, proteins, and cells is easily achievable. These materials can be trapped within the matrices of the hydrogel or trapped within the hydrophobic core of the nanofiber, depending on the cargo and the design of the MDP. Interactions between the nanofibers and their cargo can be tailored to alter the release profile, and in the most sophisticated cases, different cargos can be released in a cascading time-dependent fashion. The MDP hydrogel and its cargo can be targeted to specific locations, as the thixotropic nature of the hydrogel allows it to be easily aspirated into a syringe and then delivered from a narrow-bore needle. Also, the sequence of amino acids making up the MDP can also be modified to permit cross-linking or enzymatic degradation. Selection of sequences with or without these modifications allows one to control the rate of degradation in vivo from as rapidly as 1 week to well over 6 weeks as the MDP nanofibers are degraded to their amino acid components.

MDP sequences can also be modified to add biomimetic sequences derived from growth factors and other signaling proteins. These chemical signals are displayed at a very high density on the fibers' surface, where they contribute to the modification of cellular behavior.

Figure 1B:
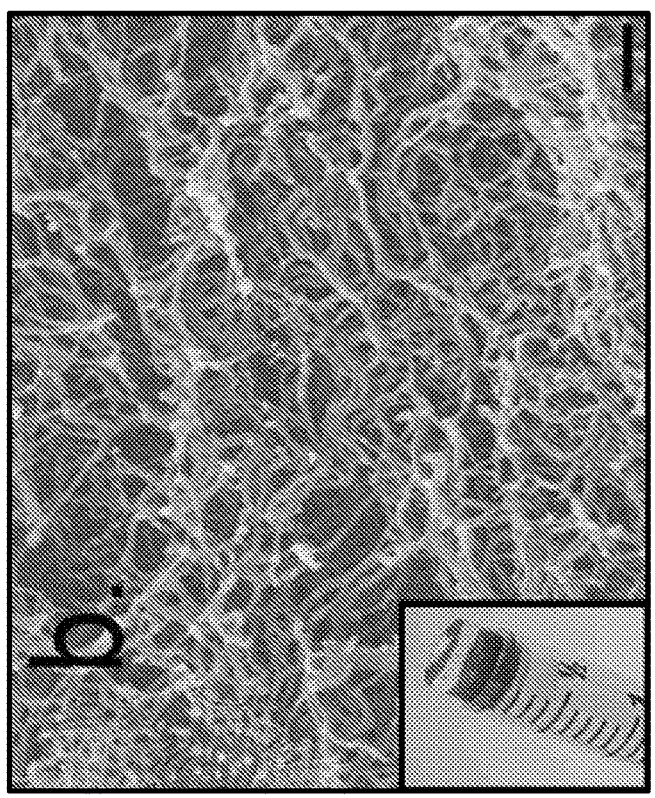
FIGS. 1A-B.
Figure 1A:
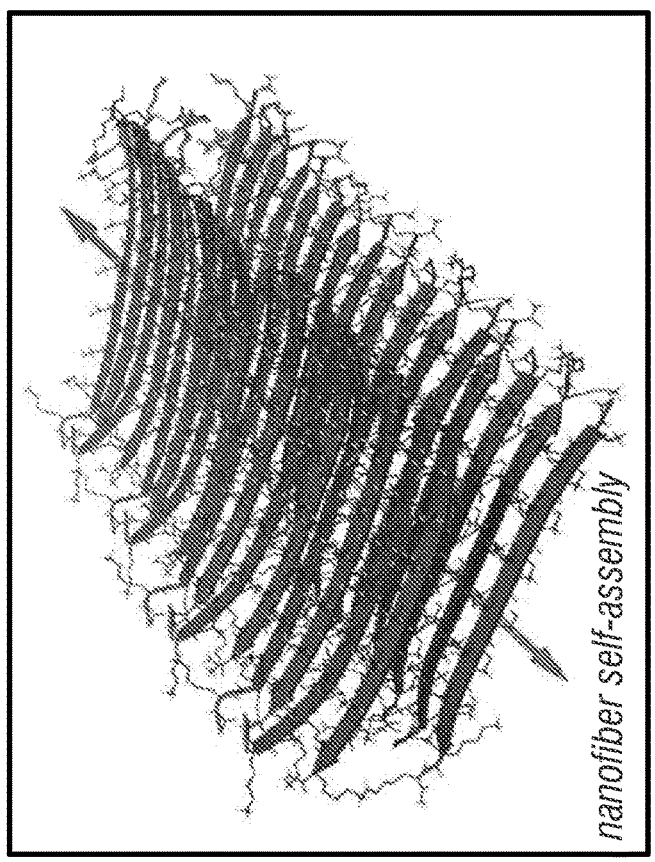

FIGS. 1A-B show the bi-layered β-sheet structure of the nanofiber created upon peptide self-assembly (illustration and SEM image). These materials have a combination of outstanding properties that make them attractive as a clinically-relevant material platform for the delivery of immunotherapeutics. First, the hydrogels are thixotropic allowing them to be easily delivered by syringe and yet remain localized for applications such as intra-tumoral injections. Second, the hydrogels undergo complete cellular infiltration in 3 days and are not fibrously encapsulated maximizing matrix-tissue interaction. Third, the design of the hydrogels can be tailored to deliver a wide range of payloads including small molecules, proteins, and cells in a controlled fashion (Moore et al., 2017; Li et al., 2016; Wickremasinghe et al., 2015; Kumar et al., 2015a; Galler et al., 2012; Bakota et al., 2011). And fourth, the MDP hydrogels are remarkably well-tolerated in vivo and generate a moderate initial inflammatory response. Importantly, immune cells are heavily recruited to sites of MDP hydrogel injection, including APCs such as dendritic cells, which are critical to innate immune sensing of tumors and downstream T cell priming. These advantageous characteristics of MDP hydrogels have led us to explore the effect of loading MDP hydrogels with CDN into a material designated "STINGel". From an immunotherapy perspective, STINGel represents a rational combination of a biomaterial that inherently recruits APCs (MDP hydrogel) loaded with a promising pharmacologic stimulant of the STING pathway (CDN) shown to strongly activate APCs in the tumor microenvironment.

III. HYPERPROLIFERATIVE DISEASES

A. Cancers and Other Hyperproliferative Diseases

While hyperproliferative diseases can be associated with any disease which causes a cell to begin to reproduce uncontrollably, the prototypical example is cancer. In some aspects, it is anticipated that the compositions of the present disclosure may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

B. Head & Neck Cancer

Of particular relevance to the present disclosure is head and neck cancer, a group of cancers that starts within the mouth, nose, throat, larynx, sinuses, or salivary glands. Symptoms may include a lump or sore that does not heal, a sore throat that does not go away, trouble swallowing, or a change in the voice. There may also be unusual bleeding, facial swelling, or trouble breathing.

About 80% of head and neck cancer is due to the use of alcohol or tobacco. Other risk factors include betel quid, certain types of human papillomavirus, radiation exposure, certain workplace exposures, and Epstein-Barr virus. Head and neck cancers are most commonly of the squamous cell carcinoma type. The diagnosis is confirmed by tissue biopsy. The degree of spread may be determined by medical imaging and blood tests.

Prevention is by not using tobacco or alcohol. While screening in the general population does not appear to be useful, screening high risk groups by examination of the throat might be useful. Often head and neck cancer is curable if detected early; however, outcomes are typically poor if detected late. Treatment may include a combination of surgery, radiation therapy, chemotherapy, and targeted therapy. Following treatment of one head and neck cancer people are at higher risk of a second cancer.

In 2015, head and neck cancers globally affected more than 5.5 million people (mouth 2.4 million, throat 1.7 million, larynx 1.4 million) and resulted in more than 379,000 deaths (mouth 146,000, throat 127,400, larynx 105,900). Together they are the seventh most frequent cancer and the ninth most frequent cause of death from cancer. In the United States about one percent of people are affected at some point in their life and males are affected twice as often as females. The usual age at diagnosis is between 55 and 65 years. The average 5-year survival following diagnosis in the developed world is 42 to 64%.

The number of new cases of head and neck cancers in the United States was 40,490 in 2006, accounting for about 3% of adult malignancies. The worldwide incidence exceeds half a million cases annually. In North America and Europe, the tumors usually arise from the oral cavity, oropharynx, or larynx, whereas nasopharyngeal cancer is more common in the Mediterranean countries and in the Far East. In Southeast China and Taiwan, head and neck cancer, specifically nasopharyngeal cancer is the most common cause of death in young men.

In 2008, there were 22,900 cases of oral cavity cancer, 12,250 cases of laryngeal cancer, and 12,410 cases of pharyngeal cancer in the United States. In 2002, 7,400 Americans were projected to die of these cancers. More than 70% of throat cancers are at an advanced stage when discovered. Men are 89% more likely than women to be diagnosed with, and are almost twice as likely to die of, these cancers.

African Americans are disproportionately affected by head and neck cancer, with younger ages of incidence, increased mortality, and more advanced disease at presentation. Laryngeal cancer incidence is higher in African Americans relative to white, Asian and Hispanic populations. There is a lower survival rate for similar tumor states in African Americans with head and neck cancer. Smoking and tobacco use are directly related to oropharyngeal (throat) cancer deaths. Head and neck cancer increases with age, especially after 50 years. Most patients are between 50 and 70 years old.

1. Symptoms

Throat cancer usually begins with symptoms that seem harmless enough, like an enlarged lymph node on the outside of the neck, a sore throat or a hoarse sounding voice. However, in the case of throat cancer, these conditions may persist and become chronic. There may be a lump or a sore in the throat or neck that does not heal or go away. There may be difficult or painful swallowing. Speaking may become difficult. There may be a persistent earache. Other possible but less common symptoms include some numbness or paralysis of the face muscles.

Presenting symptoms include a mass in the neck, neck pain, bleeding from the mouth, sinus congestion, especially with nasopharyngeal carcinoma, bad breath, sore tongue, painless ulcer or sores in the mouth that do not heal, white, red or dark patches in the mouth that will not go away, earache, unusual bleeding or numbness in the mouth, lump in the lip, mouth or gums, enlarged lymph glands in the neck, slurring of speech (if the cancer is affecting the tongue), hoarse voice which persists for more than six weeks, sore throat which persists for more than six weeks, difficulty swallowing food, and change in diet or weight loss.

2. Mouth

Squamous cell cancers are common in the mouth, including the inner lip, tongue, floor of mouth, gingivae, and hard palate. Cancers of the mouth are strongly associated with tobacco use, especially use of chewing tobacco or "dip", as well as heavy alcohol use. Cancers of this region, particularly the tongue, are more frequently treated with surgery than are other head and neck cancers.

Surgeries for oral cancers include maxillectomy (can be done with or without orbital exenteration), mandibulectomy (removal of the mandible or lower jaw or part of it), glossectomy (tongue removal, can be total, hemi or partial), radical neck dissection, mohs procedure, or combinational, e.g., glossectomy and laryngectomy done together. The defect is typically covered/improved by using another part of the body and/or skin grafts and/or wearing a prosthesis.

3. Nasopharynx

Nasopharyngeal cancer arises in the nasopharynx, the region in which the nasal cavities and the Eustachian tubes connect with the upper part of the throat. While some nasopharyngeal cancers are biologically similar to the common HNSCC, "poorly differentiated" nasopharyngeal carcinoma is lymphoepithelioma, which is distinct in its epidemiology, biology, clinical behavior, and treatment, and is treated as a separate disease by many experts.

4. Throat

Oropharyngeal squamous cell carcinomas (OSCC) begins in the oropharynx, the middle part of the throat that includes the soft palate, the base of the tongue, and the tonsils. Squamous cell cancers of the tonsils are more strongly associated with human papillomavirus infection than are cancers of other regions of the head and neck. HPV-positive oropharyngeal cancer generally has a better outcome than HPV-negative disease with a 54% better survival, but this advantage for HPV associated cancer applies only to oropharyngeal cancers. People with oropharyngeal carcinomas are at high risk of developing a second primary head and neck cancer.

5. Hypopharynx

The hypopharynx includes the pyriform sinuses, the posterior pharyngeal wall, and the postcricoid area. Tumors of the hypopharynx frequently have an advanced stage at diagnosis, and have the most adverse prognoses of pharyngeal tumors. They tend to metastasize early due to the extensive lymphatic network around the larynx.

6. Larynx

Laryngeal cancer begins in the larynx or "voice box." Cancer may occur on the vocal folds themselves ("glottic" cancer), or on tissues above and below the true cords ("supraglottic" and "subglottic" cancers respectively). Laryngeal cancer is strongly associated with tobacco smoking.

Surgery can include laser excision of small vocal cord lesions, partial laryngectomy (removal of part of the larynx) or total laryngectomy (removal of the whole larynx). If the whole larynx has been removed the person is left with a permanent tracheostomy. Voice rehabilitation in such patients can be achieved through 3 important ways—esophageal speech, tracheoesophageal puncture or electrolarynx. One would likely require the help of intensive teaching and speech therapy and/or an electronic device.

7. Trachea

Cancer of the trachea is a rare cancer which can be similar to head and neck cancer, and is sometimes classified as such. Most tumors of the salivary glands differ from the common carcinomas of the head and neck in cause, histopathology, clinical presentation, and therapy. Other uncommon tumors arising in the head and neck include teratomas, adenocarcinomas, adenoid cystic carcinomas, and mucoepidermoid carcinomas. Rarer still are melanomas and lymphomas of the upper aerodigestive tract.

8. Causes

When DNA undergoes oxidative damage, two of the most common damages change guanine to 8-hydroxyguanine or to 2,6-diamino-4-hydroxy-5-formamidopyrimidine. Alcohol and tobacco play a significant role. More than 75% of cases are believed to be due to these two factors.

Tobacco smoke is one of the main risk factors for head and neck cancer and one of the most carcinogenic compounds in tobacco smoke is acrylonitrile. Acrylonitrile appears to cause DNA damage indirectly by increasing oxidative stress, leading to increased levels of 8-oxo-2'-deoxyguanosine (8-oxo-dG) and formamidopyrimidine in DNA. Both 8-oxo-dG and formamidopyrimidine are mutagenic. DNA glycosylase NEIL1 prevents mutagenesis by 8-oxo-dG and removes formamidopyrimidines from DNA.

However, cigarette smokers have a lifetime increased risk for head and neck cancers that is 5- to 25-fold increased over the general population. The ex-smoker's risk for squamous cell cancer of the head and neck begins to approach the risk in the general population twenty years after smoking cessation. The high prevalence of tobacco and alcohol use worldwide and the high association of these cancers with these substances makes them ideal targets for enhanced cancer prevention. Alcohol and tobacco are likely synergistic in causing cancer of the head and neck. Smokeless tobacco is another cause of oral and pharyngeal cancers (oropharyngeal cancer). Cigar smoking is an important risk factor for oral cancers as well.

Other potential environmental carcinogens include occupational exposures such as nickel refining, exposure to textile fibers, and woodworking. Use of marijuana, especially while younger, is linked to an increase in squamous-cell carcinoma cases while other studies suggest use is not shown to be associated with oral squamous cell carcinoma, or associated with decreased squamous cell carcinoma incidence.

Excessive consumption of processed meats and red meat were associated with increased rates of cancer of the head and neck in one study, while consumption of raw and cooked vegetables seemed to be protective. Vitamin E was not found to prevent the development of leukoplakia, the white plaques that are the precursor for carcinomas of the mucosal surfaces, in adult smokers. Another study examined a combination of Vitamin E and beta carotene in smokers with early-stage cancer of the oropharynx, and found a worse prognosis in the vitamin users.

Recent evidence is accumulating pointing to a viral origin for some head and neck cancers.

Human papillomavirus (HPV), in particular HPV16, is a causal factor for some head and neck squamous-cell carcinoma (HNSCC). Approximately 15 to 25% of HNSCC contain genomic DNA from HPV, and the association varies based on the site of the tumor, especially HPV-positive oropharyngeal cancer, with highest distribution in the tonsils, where HPV DNA is found in (45 to 67%) of the cases, less often in the hypopharynx (13%-25%), and least often in the oral cavity (12%-18%) and larynx (3%-7%). Some experts estimate that while up to 50% of cancers of the tonsil may be infected with HPV, only 50% of these are likely to be caused by HPV (as opposed to the usual tobacco and alcohol causes). The role of HPV in the remaining 25-30% is not yet clear. Oral sex is not risk free and results in a significant proportion of HPV-related head and neck cancer. Positive HPV16 status is associated with improved prognosis over HPV-negative OSCC.

Induction of cancer can be associated for the expression of viral oncoproteins, the most important human papillomavirus E6 and E7, or other mechanisms many of them run by the integration such as the generation of altered transcripts, disruption of tumor suppressors, high levels of DNA amplifications, interchromosomial rearrangements, or changes in DNA methylation patterns, the latter being able to find even when the virus is identified in episomes. E6 sequesters p53 to promote p53 degradation while pRb inhibits E7. p53 prevents cell growth when DNA is damaged by activating apoptosis and p21, a kinase that blocks the formation of cyclin D/Cdk4 avoiding pRb phosphorylation and thereby prevents release of E2F is a transcription factor required for activation of genes involved in cell proliferation. pRb remains bound to E2F while this action phosphorylated preventing activation of proliferation. Therefore, E6 and E7 act synergistically in triggering cell cycle progression and therefore uncontrolled proliferation by inactivating the p53 and Rb tumor suppressors.

Epstein-Barr virus (EBV) infection is associated with nasopharyngeal cancer. Nasopharyngeal cancer occurs endemically in some countries of the Mediterranean and Asia, where EBV antibody titers can be measured to screen high-risk populations. Nasopharyngeal cancer has also been associated with consumption of salted fish, which may contain high levels of nitrites.

The presence of acid reflux disease (GERD—gastroesphogeal reflux disease) or larynx reflux disease can also be a major factor. Stomach acids that flow up through the esophagus can damage its lining and raise susceptibility to throat cancer.

Patients after hematopoietic stem cell transplantation (HSCT) are at a higher risk for oral squamous cell carcinoma. Post-HSCT oral cancer may have more aggressive behavior with poorer prognosis, when compared to oral cancer in non-HSCT patients. This effect is supposed to be owing to the continuous lifelong immune suppression and chronic oral graft-versus-host disease.

There are a wide variety of factors which can put someone at a heightened risk for throat cancer. Such factors include smoking or chewing tobacco or other things, such as gutkha, or paan, heavy alcohol consumption, poor diet resulting in vitamin deficiencies (worse if this is caused by heavy alcohol intake), weakened immune system, asbestos exposure, prolonged exposure to wood dust or paint fumes, exposure to petroleum industry chemicals, and being over the age of 55 years. Another risk factor includes the appearance of white patches or spots in the mouth, known as leukoplakia; in about ⅓ of the cases this develops into cancer. Other heightened risks: breathing or inhaling silica from cutting concrete, stone or cinder-blocks, especially in enclosed areas such as a warehouse, garage or basement.

9. Diagnosis

A patient usually presents to the physician complaining of one or more of the above symptoms. The patient will typically undergo a needle biopsy of this lesion, and a histopathologic information is available, a multidisciplinary discussion of the optimal treatment strategy will be undertaken between the radiation oncologist, surgical oncologist, and medical oncologist.

Throat cancers are classified according to their histology or cell structure, and are commonly referred to by their location in the oral cavity and neck. This is because where the cancer appears in the throat affects the prognosis—some throat cancers are more aggressive than others depending upon their location. The stage at which the cancer is diagnosed is also a critical factor in the prognosis of throat cancer. Treatment guidelines recommend routine testing for the presence of HPV for all oropharyngeal squamous cell carcinoma tumours.

Squamous-cell carcinoma is a cancer of the squamous cell—a kind of epithelial cell found in both the skin and mucous membranes. It accounts for over 90% of all head and neck cancers, including more than 90% of throat cancer. Squamous cell carcinoma is most likely to appear in males over 40 years of age with a history of heavy alcohol use coupled with smoking. The tumor marker Cyfra 21-1 may be useful in diagnosing squamous cell carcinoma of the head/neck.

Adenocarcinoma is a cancer of epithelial tissue that has glandular characteristics. Several head and neck cancers are adenocarcinomas (either of intestinal or non-intestinal cell-type).

10. Management

Improvements in diagnosis and local management, as well as targeted therapy, have led to improvements in quality of life and survival for people with head and neck cancer. After a histologic diagnosis has been established and tumor extent determined, the selection of appropriate treatment for a specific cancer depends on a complex array of variables, including tumor site, relative morbidity of various treatment options, patient performance and nutritional status, concomitant health problems, social and logistic factors, previous primary tumors, and patient preference. Treatment planning generally requires a multidisciplinary approach involving specialist surgeons and medical and radiation oncologists.

Several generalizations are useful in therapeutic decision making, but variations on these themes are numerous. Surgical resection and radiation therapy are the mainstays of treatment for most head and neck cancers and remain the standard of care in most cases. For small primary cancers without regional metastases (stage I or II), wide surgical excision alone or curative radiation therapy alone is used. For more extensive primary tumors, or those with regional metastases (stage III or IV), planned combinations of pre- or postoperative radiation and complete surgical excision are generally used. More recently, as historical survival and control rates are recognized as less than satisfactory, there has been an emphasis on the use of various induction or concomitant chemotherapy regimens.

Many different treatments and therapies are used in the treatment of throat cancer. The type of treatment and therapies used are largely determined by the location of the cancer in the throat area and also the extent to which the cancer has spread at time of diagnosis. Patients also have the right to decide whether or not they wish to consent to a particular treatment. For example, some may decide to not undergo radiation therapy which has serious side effects if it means they will be extending their lives by only a few months or so. Others may feel that the extra time is worth it and wish to pursue the treatments.

Surgery as a treatment is frequently used in most types of head and neck cancer. Usually the goal is to remove the cancerous cells entirely. This can be particularly tricky if the cancer is near the larynx and can result in the patient being unable to speak. Surgery is also commonly used to resect (remove) some or all of the cervical lymph nodes to prevent further spread of the disease.

$CO_2$ laser surgery is also another form of treatment. Transoral laser microsurgery allows surgeons to remove tumors from the voice box with no external incisions. It also allows access to tumors that are not reachable with robotic surgery. During the surgery, surgeon and pathologist work together to assess the adequacy of excision ("margin status"), minimizing the amount of normal tissue removed or damaged. This technique helps give the patient as much speech and swallowing function as possible after surgery.

Radiation therapy is the most common form of treatment. There are different forms of radiation therapy, including 3D conformal radiation therapy, intensity-modulated radiation therapy, particle beam therapy and brachytherapy, which are commonly used in the treatments of cancers of the head and neck. Most patients with head and neck cancer who are treated in the United States and Europe are treated with intensity-modulated radiation therapy using high energy photons. At higher doses, head and neck radiation is associated with thyroid dysfunction and pituitary axis dysfunction.

Chemotherapy in throat cancer is not generally used to cure the cancer as such. Instead, it is used to provide an inhospitable environment for metastases so that they will not establish in other parts of the body. Typical chemotherapy agents are a combination of paclitaxel and carboplatin. Cetuximab is also used in the treatment of throat cancer.

Docetaxel-based chemotherapy has shown a very good response in locally advanced head and neck cancer. Docetaxel is the only taxane approved by US FDA for Head and neck cancer, in combination with cisplatin and fluorouracil for the induction treatment of patients with inoperable, locally advanced squamous cell carcinoma of the head and neck.

While not specifically a chemotherapy, amifostine is often administered intravenously by a chemotherapy clinic prior to a patient's IMRT radiotherapy sessions. Amifostine protects the patient's gums and salivary glands from the effects of radiation.

Photodynamic therapy may have promise in treating mucosal dysplasia and small head and neck tumors Amphinex is giving good results in early clinical trials for treatment of advanced head and neck cancer.

Targeted therapy, according to the National Cancer Institute, is "a type of treatment that uses drugs or other substances, such as monoclonal antibodies, to identify and attack specific cancer cells without harming normal cells." Some targeted therapy used in squamous cell cancers of the head and neck include cetuximab, bevacizumab and erlotinib.

The best quality data are available for cetuximab since the 2006 publication of a randomized clinical trial comparing radiation treatment plus cetuximab versus radiation treatment alone. This study found that concurrent cetuximab and radiotherapy improves survival and locoregional disease control compared to radiotherapy alone, without a substantial increase in side effects, as would be expected with the concurrent chemoradiotherapy, which is the current gold standard treatment for advanced head and neck cancer. Whilst this study is of pivotal significance, interpretation is difficult since cetuximab-radiotherapy was not directly compared to chemoradiotherapy. The results of ongoing studies to clarify the role of cetuximab in this disease are awaited with interest.

Another study evaluated the impact of adding cetuximab to conventional chemotherapy (cisplatin) versus cisplatin alone. This study found no improvement in survival or disease-free survival with the addition of cetuximab to the conventional chemotherapy. However, another study which completed in March 2007 found that there was an improvement in survival. A 2010 review concluded that the combination of cetuximab and platin/5-fluorouracil should be considered the current standard first-line regimen.

Gendicine is a gene therapy that employs an adenovirus to deliver the tumor suppressor gene p53 to cells. It was approved in China in 2003 for the treatment of head and neck squamous cell carcinoma.

Head and neck cancer clinical trials employing bevacizumab, an inhibitor of the angiogenesis receptor VEGF, were recruiting patients as of March 2007.

Erlotinib is an oral EGFR inhibitor, and was found in one Phase II clinical trial to retard disease progression. Scientific evidence for the effectiveness of erlotinib is otherwise lacking to this point. A clinical trial evaluating the use of erlotinib in metastatic head and neck cancer is recruiting patients as of March, 2007.

11. Prognosis

Although early-stage head and neck cancers (especially laryngeal and oral cavity) have high cure rates, up to 50% of head and neck cancer patients present with advanced disease. Cure rates decrease in locally advanced cases, whose probability of cure is inversely related to tumor size and even more so to the extent of regional node involvement.

Consensus panels in America (AJCC) and Europe (UICC) have established staging systems for head and neck squamous-cell cancers. These staging systems attempt to standardize clinical trial criteria for research studies, and attempt to define prognostic categories of disease. Squamous cell cancers of the head and neck are staged according to the TNM classification system, where T is the size and configuration of the tumor, N is the presence or absence of lymph node metastases, and M is the presence or absence of distant metastases. The T, N, and M characteristics are combined to produce a "stage" of the cancer, from I to IVB.

Survival advantages provided by new treatment modalities have been undermined by the significant percentage of patients cured of head and neck squamous cell carcinoma (HNSCC) who subsequently develop second primary tumors. The incidence of second primary tumors ranges in studies from 9% to 23% at 20 years. Second primary tumors are the major threat to long-term survival after successful therapy of early-stage HNSCC. Their high incidence results from the same carcinogenic exposure responsible for the initial primary process, called field cancerization.

Like any cancer, metastasization affects many areas of the body, as the cancer spreads from tissue to tissue and organ to organ. For example, if it spreads to the bone marrow, it will prevent the body from producing enough red blood cells and affects the proper functioning of the white blood cells and the body's immune system; spreading to the circulatory system will prevent oxygen from being transported to all the cells of the body; and throat cancer can throw the nervous system into chaos, making it unable to properly regulate and control the body.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render agents stable and allow for uptake by target cells. Aqueous compositions of the present disclosure comprise an effective amount of the agents to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the agents of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, or intraperitoneal injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the biaryl compounds of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary, and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing induction of an immune response, and/or eventually inducing killing of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the cancer and other drugs being administered concurrently. A composition as described herein is typically administered at a dosage that directly or indirectly inhibits the growth or proliferation of a cancer cell, or induces death of cancerous cells. In some embodiments, amounts of the agents used to inhibit or kill cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the biaryl compounds may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for cancer, or having a symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the biaryl compounds may be used in combination therapies with an additional antimicrobial agent such as an antibiotic or a compound which mitigates one or more of the side effects experienced by the patient.

Furthermore, it is very common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the biaryl compounds may precede or follow the other treatment by intervals ranging from minutes to weeks. One would generally ensure that a significant period of time did not expire between each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Some agents or therapies suitable for use in a combined therapy with agents according to the present disclosure against cancer are discussed below, although other combinations are contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate;

hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PS K polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotec an (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8, and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311).

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

It also should be pointed out that any of the foregoing therapies may prove useful by themselves in treating cancer.

V. SYNTHETIC METHODS

The inventors have performed experiments to determine how the design of the peptide sequence in the MDP can allow for the variation of the supramolecular assembly in the forming fibers. All MDPs exhibit the same general chemical design, with the core of the peptide consisting of alternating hydrophilic and hydrophobic amino acids and the termini of the peptide consisting of charged amino acids. Incorporation of bioactive sequences in either the central block or flanking regions of MDPs can further enhance activity.

By using glutamate or lysine as the charged terminal residues, the inventors can generate peptides with net negative or positive charge, respectively. Hydrophilic residues include glutamine, serine, threonine, and cysteine, while hydrophobic residues include both aliphatic and aromatic side chains, such as leucine. Regardless of the specific amino acids selected to compose the peptide, the chemical design of the MDP causes these peptides to adopt a β-sheet secondary structure with hydrophobic residues on one face of the peptide and hydrophilic residues on the other. Arising from the alternating hydrophilic and hydrophobic residues in the core of the MDP, this facial amphiphile is key for the supramolecular assembly of peptides to form nanofibers.

Because of the amphiphilic nature of MDPs, they self-assemble to form nanofibers in aqueous solution. Each fiber consists of a bilayer of peptides with the hydrophilic peptide faces exposed to the surrounding aqueous solution and the hydrophobic peptide faces sequestered into the core of the MDP. The inventors have divided the fibers into repeating units to understand why MDPs undergo supramolecular assembly, and call the repeating unit of the MDP nanofiber a "hydrophobic sandwich." This sandwich comprises four peptides, and the hydrophobic faces of the MDPs pack against one another to minimize contact with surrounding water molecules. When aligned, hydrogen bonding between adjacent peptide backbones can occur, further stabilizing the assembled peptides. Typical diameter of the fiber is 6 nm.

The inventors have also discovered methods of defining the peptide orientation within the nanofibers, specifically the formation of parallel or antiparallel hydrogen-bonding networks. For instance, most MDPs contain leucine residues as their hydrophobic core, and all of these sequences exhibit antiparallel packing of the β-sheet peptides. However, by the use of tryptophan or tyrosine in place of leucine, it is possible to change this orientation to parallel packing of the peptides. Modeling suggests that this is the case because the side chains of these two amino acids form stronger interactions in the hydrophobic sandwich when fibers self-assemble in a parallel rather than antiparallel fashion, thus defining the hydrogen-bonding orientation. While not mechanistic in nature, the idea of the hydrophobic sandwich illustrates the concepts driving self-assembly of MDPs. Regardless, the resulting nanofiber exhibits a width of the peptide sequence, a height of the MDP dimer, and an "infinite" length after charge screening. To characterize MDPs, the inventors confirm successful synthesis using mass spectrometry. Secondary structure is assessed using circular dichroism spectroscopy and infrared spectroscopy. Self-assembly is measured using atomic force microscopy, scanning electron microscopy, and/or transmission electron microscopy. Hydrogel formation is determined using oscillatory rheology.

With the goal of creating self-assembled nanofibrous structures while maintaining solubility, the proper balance of charged residues to hydrophilic-hydrophobic residue repeats was determined experimentally. Through circular dichroism (CD) spectroscopy and transmission electron microscopy (TEM), it was found that multidomain peptides typically require at least 3 times more hydrophilic-hydrophobic repeats than charged residues to form nanofibers. When too few charged residues are included in the design, the peptides have very poor solubility and are difficult to handle and purify.

However, if the peptide contains too many charged residues, fibers fail to form as a result of like-charge repulsion at the peptide termini In terms of hydrophilic-hydrophobic amino acid repeats, a peptide without a sufficient number will either fail to form fibers or form fibers contaminated with amorphous aggregates of assembled peptides. By properly balancing the number of charged residues with the number of hydrophilic-hydrophobic residue repeats, it is possible to consistently obtain self-assembled nanofibers of relatively uniform length and diameter.

MDPs are further engineered at the primary sequence level to allow for simple and biologically compatible hydrogelation through cross-linking of peptide nanofibers. The inclusion of charged residues at the peptide termini serves two purposes—first, to increase the solubility, and second, to enable non-covalent cross-linking between peptide fibers. In aqueous solution, the charged residues at the peptide termini oppose fiber self-assembly; however, the addition of multivalent oppositely charged salts triggers hydrogelation by using these charged residues as locations to cross-link fibers. For positively-charged peptides, the inventors typically use a phosphate buffer for crosslinking, while a magnesium or calcium salt is appropriate for cross-linking of negatively charged peptides. Monovalent salts such as NaCl also work but require much higher concentrations.

If desired, it is also possible to cross-link peptides using drug molecules of the appropriate charge to employ non-covalent forces. Significantly, these non-covalent interactions are capable of reformation after disruption, allowing the MDP hydrogel to be a thixotropic material that liquefies under a shearing force and regels when the shearing force ceases. When a shearing force is applied, the storage and loss moduli invert, signifying liquification. Following removal of the shearing force, the storage and loss moduli recover to approximately 75% of their initial values nearly immediately and to 100% over 15 min In practical terms, the ability to shear thin and shear recover is an extremely valuable property of the MDP hydrogel, as it enables the material to be easily delivered via injection.

While the inventors most commonly use non-covalent crosslinking with salt solutions to trigger hydrogelation, they have also studied covalent cross-linking of peptide nanofibers. Because covalent cross-linking forms stronger interactions between peptide fibers, a dramatic increase in storage modulus is observed for covalently crosslinked MDP hydrogels. One method of covalent crosslinking uses cysteine residues as hydrophilic amino acids in the core of the MDP. For this strategy, general oxidation results in intrafiber and interfiber covalent disulfide bonds. The disulfide bonds formed between two cysteine residues result in a dramatic increase in gel storage modulus. It is also possible to utilize enzymes to covalently cross-link peptide fibers, such as lysyl oxidase, an enzyme found in nature that functions to cross-link ECM components. In this system, lysyl oxidase acts on the lysine side chains of the MDP and covalently cross-links peptide nanofibers. This increases the storage modulus by over an order of magnitude in comparison to the non-covalently cross-linked system of the same MDP.

While MDPs are relatively short in length, typically between 18 and 30 amino acids, careful selection of these amino acids results in the desired chemical and mechanical properties. Alternation of hydrophilic and hydrophobic residues drives β-sheet formation in either a parallel or antiparallel orientation. Charged residues at the peptide termini determine the overall scaffold charge and therefore which molecules can be used to non-covalently cross-link the peptide nanofibers. To influence the mechanical properties, non-covalent or covalent crosslinking can be used. Through the design of the peptide primary RAHYNIVTF (SEQ ID NO: 2), the inventors have created a self-assembling nanofibrous scaffold capable of delivery via syringe injection.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods and Materials

Synthesis of MDP hydrogels. Peptides cam be synthesized by automated solid phase peptide synthesis using a standard Fmoc protection strategy as previously described (31,32). Peptides are purified by reverse phase HPLC and dialyzed against deionized water to desalt. Peptides are characterized by ESI and MALDI-TOF mass spectrometry to ensure proper sequence.

STINGel formulation. All STINGels are prepared to a final concentration of 1% by weight with or without the CDN. Final CDN concentration is 0.67 µg/µL. All MDP hydrogel formulation are tested by oscillatory rheology to ensure consistent mechanical properties and examined by Transmission Electron Microscopy to ensure expected nanostructure as previously described (Aulisa et al., 2009; Galler et al., 2010; Dong et al., 2007). Collagen hydrogel controls are prepared according to the protocol provided by the manufacturer with the addition of CDN to 0.67 µg/µL.

CDN release kinetics. 30 µL CDN-loaded gel aliquots are deposited into 96 well plates with 200 µL of buffer added to the top of the gels at time point t=0. For all kinetics experiments, a Thermo Scientific Nanodrop 2000C Spectrophotometer is used to measure UV absorbance at 259 nm, the characteristic wavelength of maximum absorbance for the adenine nucleobases present in the CDN. See FIG. 1A for an example of preliminary release kinetics data.

In vivo subcutaneous implants. 200 µL subcutaneous injections are made in two separate 1-inch spaced sites on the dorsal flank. At tested time points mice are euthanized and the dorsal skin around the entire implant is removed, washed with PBS, and fixed in formalin for 24 hours prior to tissue processing (Wellings & Atherton, 1997; Guy & Fields, 1997). Details are provided in the Vertebrate Animal section. Tissue is processed to paraffin blocks, sectioned at 7 µm, deparaffinized and stained for cellular infiltrate using hematoxylin and eosin (H&E) and Masson's Trichrome. Here, and elsewhere, male and female populations will be assessed combined as well as separately to determine if sexual dichotomy exists in the biomaterial interaction and regenerative response.

Flow cytometric analysis of implant infiltration. Implanted gels are harvested from mice, digested and processed into single cell suspension. Cells are incubated with blocking antibody, followed by addition of antibodies to create three panels: myeloid cells (CD45, Gr-1, Ly-6C, CD11b, F4/80), lymphoid cells (CD45, NK-1.1, CD11b, CD3e, CD8a, CD4, CD19) and dendritic cells (CD45, CD8a, CD11b, CD11c, PDCA-1 and CD103). For each time point five mice with two hydrogel boluses are assessed for an n of 10.

MOC-2-E6E7 Orthotopic murine model of HNSCC. 6 week-old male and female C57BL/6 mice will be inoculated in the left maxillary vestibule with MOC-2-E6E7 cells (30,000 cells in 30 µl volume). Animals will be monitored using a body condition scoring system to ensure they maintain a healthy weight and show no obvious signs of distress. At Day 14 post-tumor inoculation, STINGel (20 jug CDN in 30 µl of MDP hydrogel) or controls (as above) are injected into the oral tumor site. Animal studies will be done in triplicate, independent experiments for significance. Between-group differences in flow cytometric data will be statistically evaluated with one-way ANOVA and post-hoc analysis using Tukey's method. Differences between groups will be considered significant if p<0.05. In efficacy studies, Kaplan-Meier survival curves will be compared using the log-rank/Mantel-Cox test and tumor growth curves will be analyzed using the Koziol method (Koziol et al., 1981; 1982).

Flow cytometric analysis of tumor microenvironment. At the time of euthanasia, tumors are harvested from mice, digested and processed into single cell suspension. Cells are incubated with blocking antibody, live/dead stain, followed by addition of antibody staining panels. The inventors will assess for the presence of dendritic cells including conventional, plasmacytoid, and CD8+ subtypes (CD45, CD11b, CD11c, PDCA-1, CD8). Further, they will first assess tumor cells and dendritic cells for FAM-CDN uptake using an antibody panel containing CD45, CD3, CD19, CD11b, CD11c, PDCA-1, cytokeratin8/18, and CD8 with an additional channel for the fluorescent CDN label. Follow-up studies will use a separate antibody panel to determine markers of activation: (CD45, CD3, CD19, CD11b, CD11c, PDCA-1, CD8, MHC I (H-2Kb and H-2Db), MHC II (I-A/I-E), and CD40). Finally, the inventors will examine venous blood for E7-specific cytotoxic lymphocytes using the antibody panel: CD45, CD3, CD19, CD4, CD8, followed by tetramer H2D(b)/E7 epitope RAHYNIVTF (SEQ ID NO: 2).

Gene expression analysis of Type 1 IFN activation in the TME. To analyze gene expression markers of activation in tumor cells vs. dendritic cells, tumors will be harvested 3 days after intratumoral injection of STINGel and processed into single-cell suspension, magnetically sorted (autoMACS by Miltenyi Biotec), then both the sorted tumor cells and immune cells will undergo downstream PCR analysis for expression of Type 1 IFN pathway genes (IFN-β, STING, ERAP, proteasome, and TAP proteins-TAP1, TAP2, TAPbp).

Example 2—Results

Figure 3A:
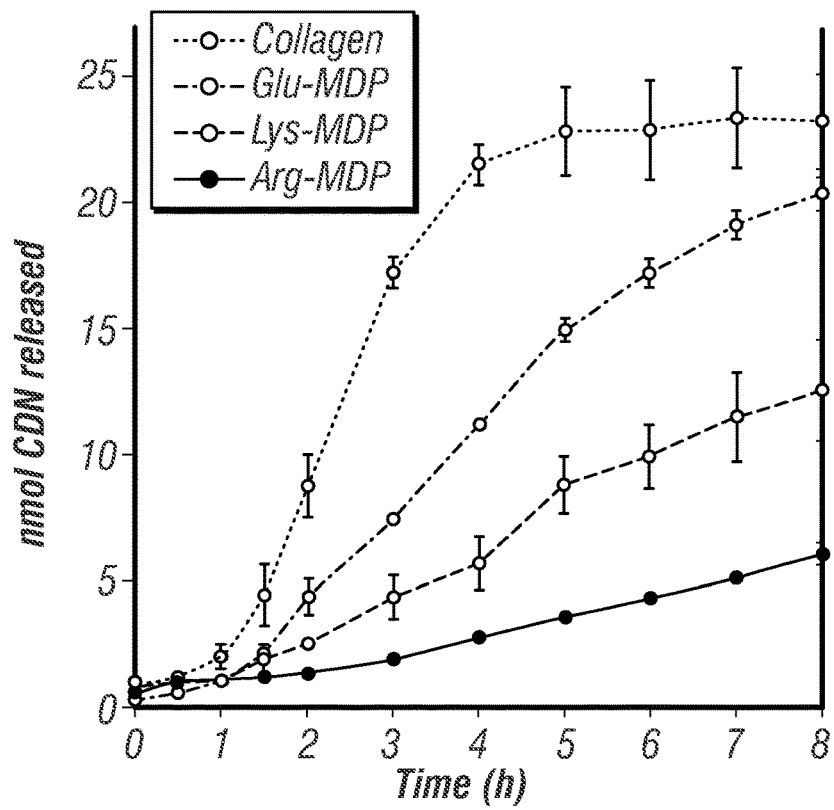
FIGS. 3A-E.
Figure 3B:
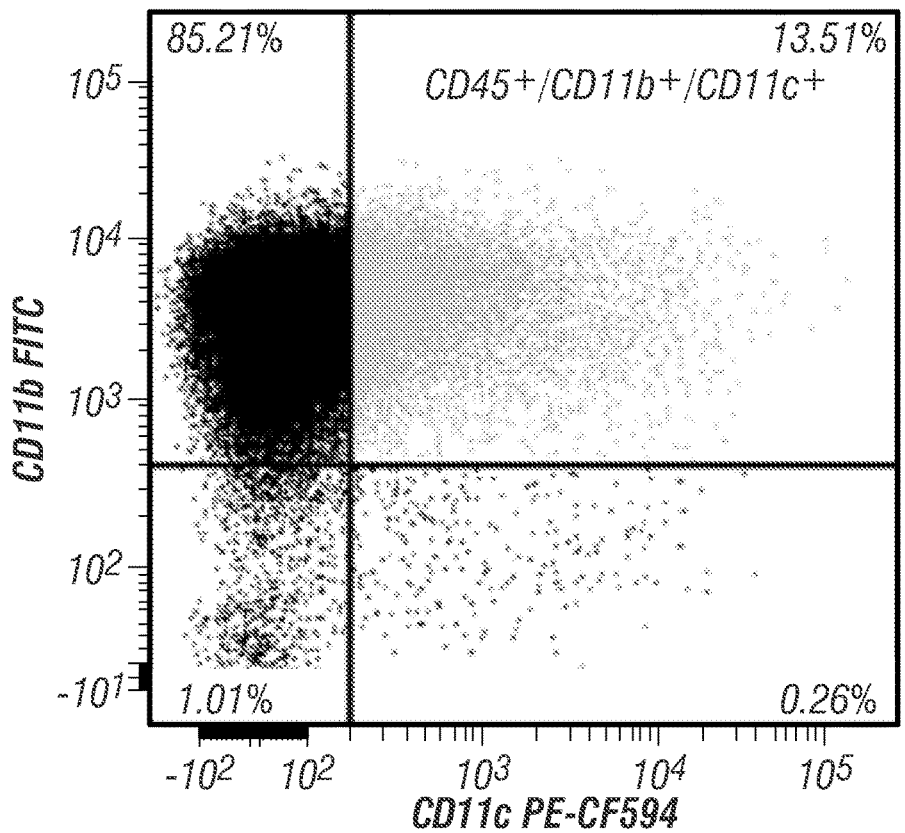
Figure 3E:
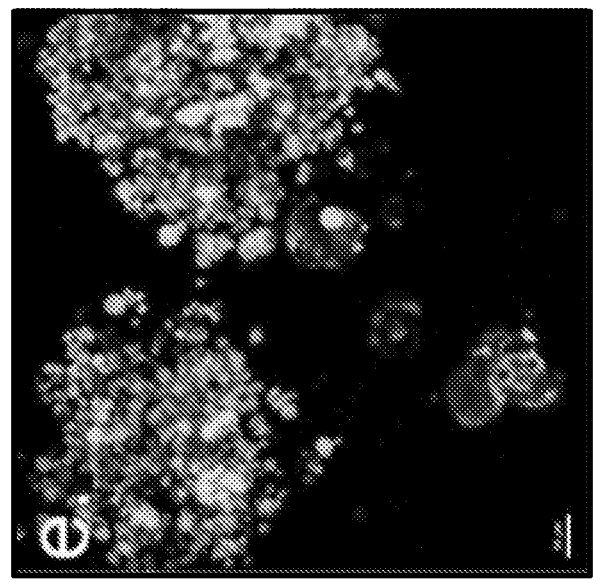
Figure 3D:
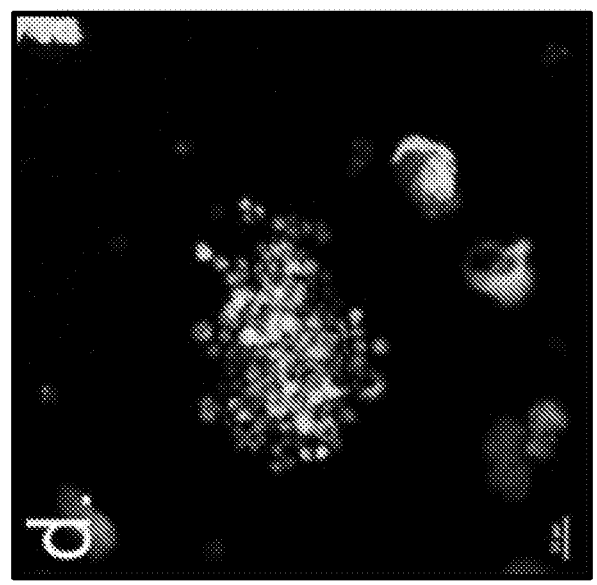
Figure 3C:
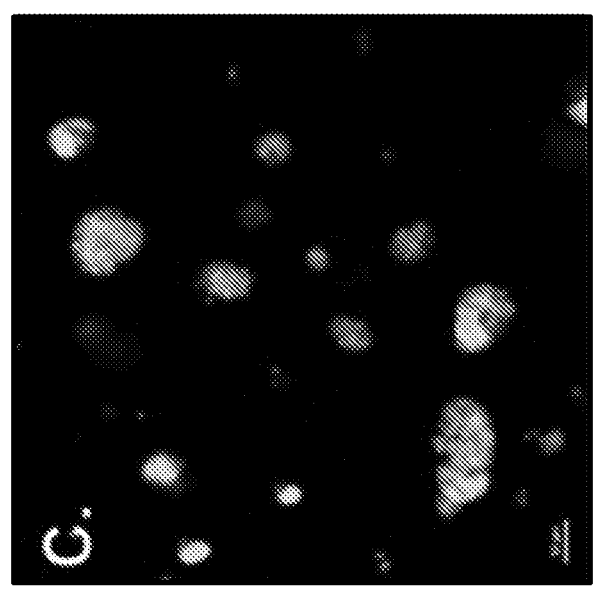

In vitro studies in the inventors' lab indicate that MDP hydrogels loaded with CDN can delay release by a factor of approximately 10, versus control collagen gels and that the hydrogel is not intrinsically toxic to murine HNSCC tumor cells, allowing for cell proliferation over time (FIGS. 3C-E). Similarly, in vivo studies injected MDP hydrogel into the subcutaneous flank of mice resulting in robust recruitment of immunocytes including "professional" APCs such as dendritic cells within 3 days (FIG. 3B).

MOC-2-E6E7 is a challenging new preclinical model of HPV-associated HNSCC. Both human- and murine-derived HNSCC cell lines have been developed and used in multiple applications including the in vitro testing of new anticancer agents and in vivo testing of chemotherapeutic and antineoplastic treatments in xenogeneic models using immunocompromised mice (Méry et al., 2017). With the recent surge in interest surrounding immunotherapy for HNSCC, more relevant syngeneic, immunocompetent models are necessary to study the complex interactions taking place between tumor cells and the host immune system. In 2012, Judd et al. described new syngeneic mouse models of oral cancer, comparing the tumor-infiltrating lymphocytes present in relatively indolent (MOC1) versus aggressive, metastatic (MOC2) tumors (Judd et al., 2012a). The immunophenotype (Judd et al., 2012a,b) and genomic landscape (Onken et al., 2014) of these preclinical HNSCC models is well characterized and subsequent studies have used MOC1 and MOC2 to test checkpoint inhibitors and STING agonists (Moore et al., 2016a,b).

Figure 2A:
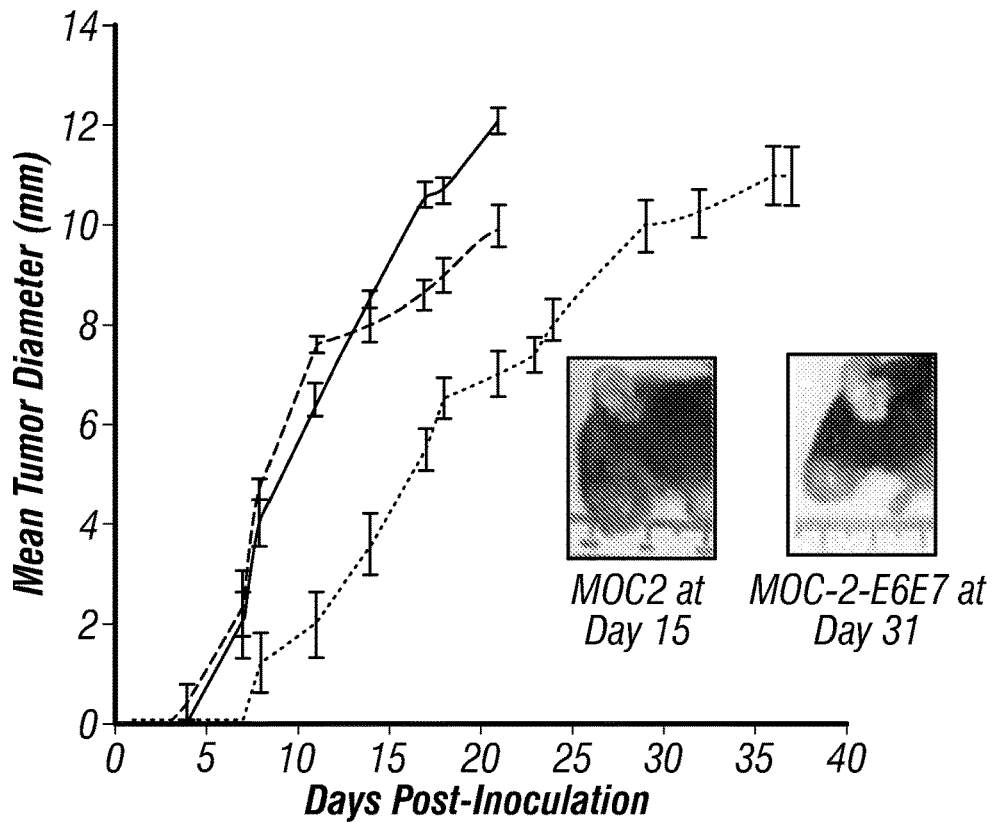
FIGS. 2A-E.
Figure 2B:
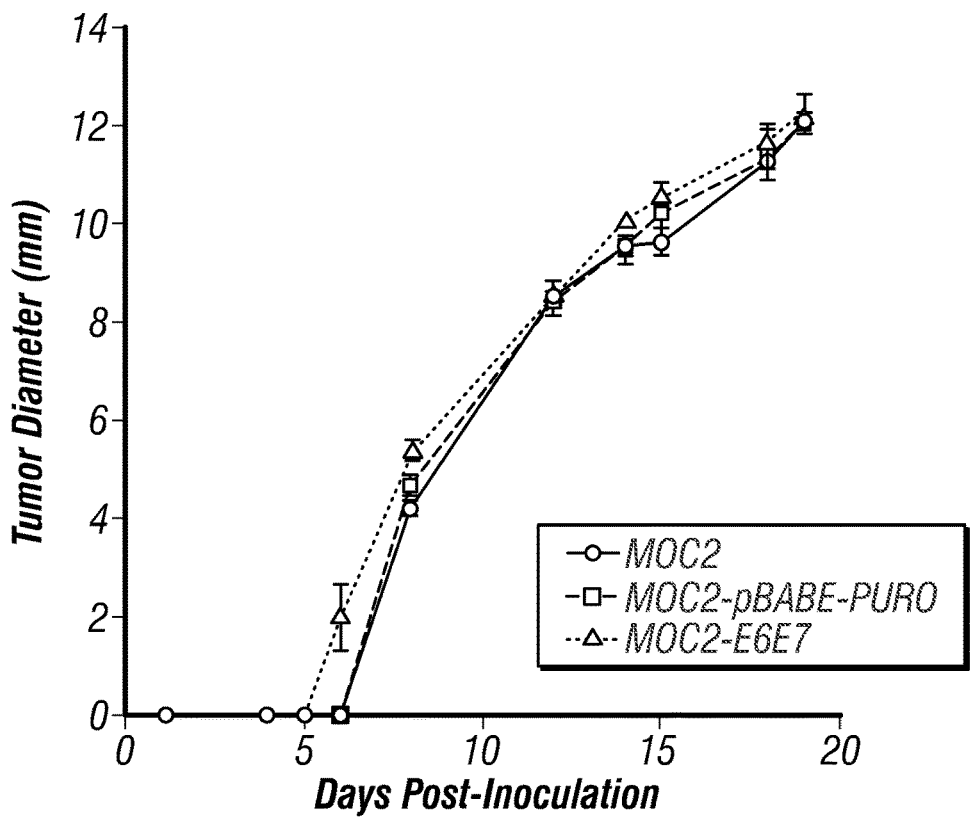
Figure 2C:
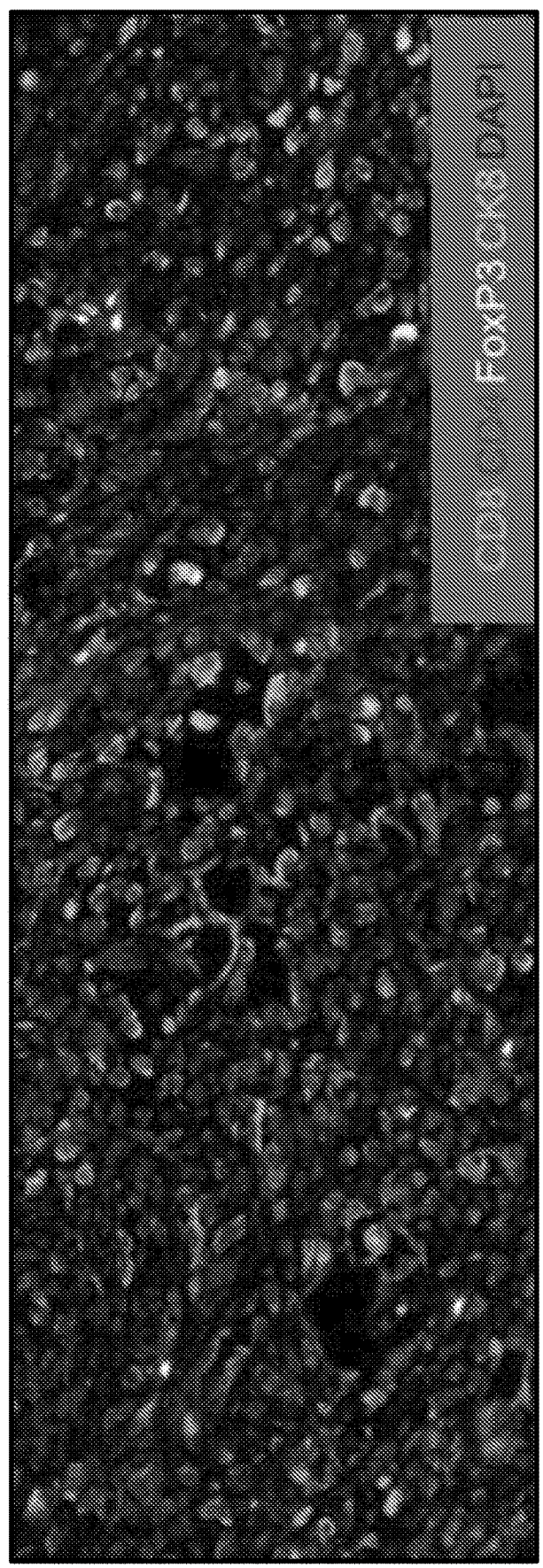
Figure 2D:
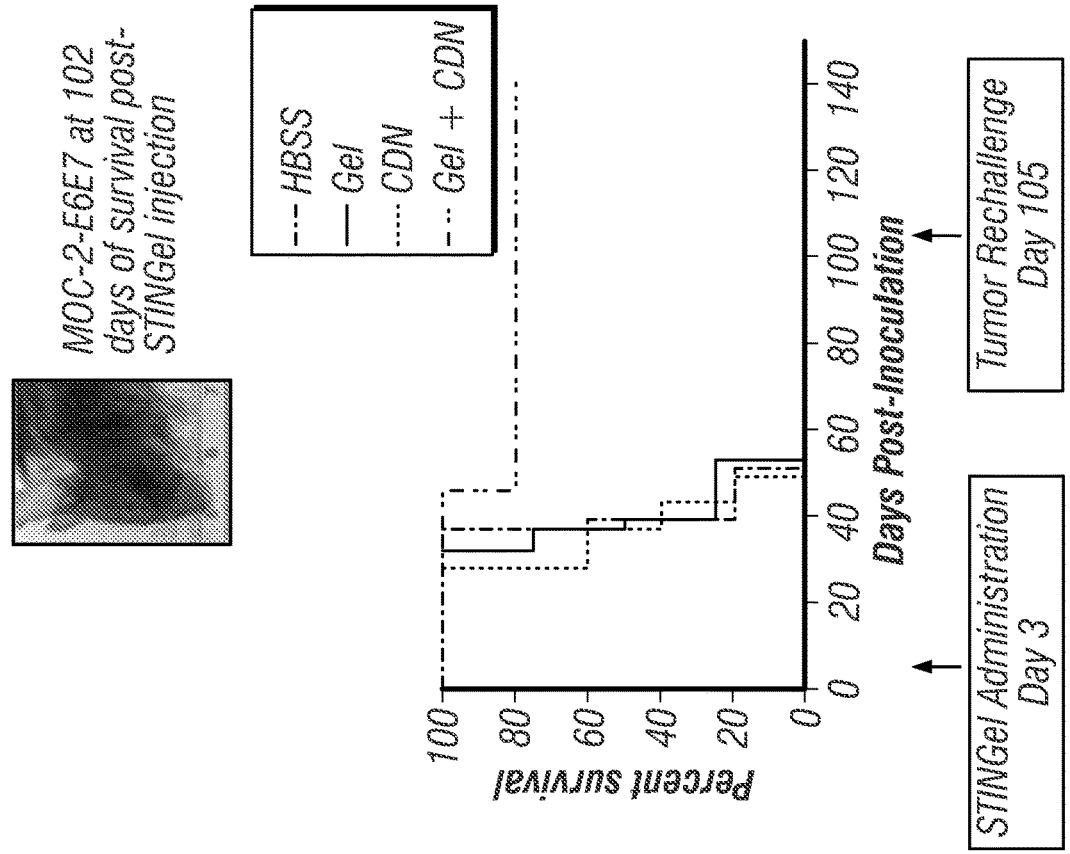
Figure 2E:
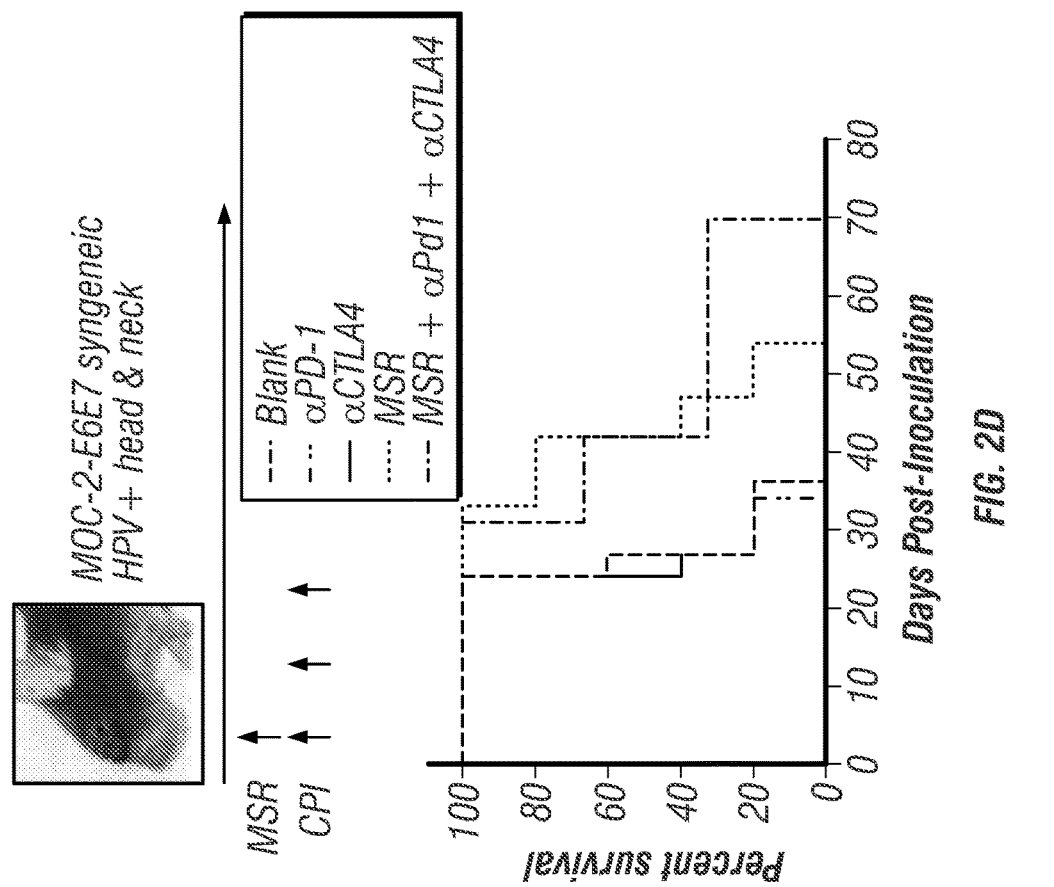

In recognition of the rising incidence of human papilloma virus (HPV) related-HNSCC (28,29) and the potential for immunotherapies to target tumor-specific HPV antigens associated with these tumors, the inventors transduced the MOC2 cell line with two key viral antigens from high-risk HPV 16, namely E6 and E7, and named the new cell line MOC-2-E6E7. Data show that C57BL/6 mice inoculated with MOC-2-E6E7 tumors in the oral cavity display slower tumor growth versus those inoculated with MOC2, a difference which is eliminated in Rag1-knockout mice lacking mature B- and T-cells, suggesting a role for host immunity in tumor control (FIGS. 2A-B). Multiplex immunohistochemical staining of MOC-2-E6E7 tumors shows a robust cytotoxic lymphocyte (CTL) infiltrate (FIG. 2C). Implantation of a therapeutic cancer vaccine targeting HPV E7 conferred a statistically-significant increase in median survival time (FIG. 2D). Nonetheless, even rationally-designed immunotherapies combining multiple injections of two separate checkpoint inhibitor antibodies and a mesoporous silica rod-based cancer vaccine administered 3 days after tumor inoculation, have been unable to induce a significant anti-tumor immune response which results in long-term survival (FIG. 2E).

Thus, it was incredibly unexpected when a single injection of STINGel into the MOC-2-E6E7 tumor site showed a significant survival advantage for STINGel-treated mice versus CDN-injected controls over 100 days. As FIG. 2E shows, 80% of STINGel treated mice not only survived for 100 days after MOC-2-E6E7 injection, but 100% of surviving mice displayed immunological memory and were not affected by a second injection of MOC-2-E6E7 cells. In contrast, mice treated with CDN alone, MDP gel alone or buffer control all faired equally poorly with 100% mortality before day 60. To the inventors' knowledge, multiple intratumoral injections of CDN alone have shown only minimal efficacy in MOC1 models of head and neck cancer (Moore et al., 2016a; Gadkaree et al., 2017), requiring combination with a separate non-redundant immunotherapeutic agent such as antibodies targeted against the PD-1/PD-L1 signaling axis to improve their performance against the indolent, slow-growing MOC1 tumors. Together these extraordinary results suggest that STINGel represents an innovative and novel injectable immunotherapy that has the potential to significantly alter the immunophenotype of a challenging HNSCC tumor microenvironment, leading to robust and durable anti-tumor immunity.

The inventors hypothesize that by loading MDP hydrogels with the synthetic STING agonist CDN, this unique STINGel formulation will render immunologically refractory tumors sensitive to immune-mediated killing through multiple mechanisms including: 1) prolonged release of CDN, 2) MDP-driven recruitment of critical APCs to the site of injection, and 3) enhanced Type 1 IFN response in both tumor cells and APCs within the TME. The data presented here show that a single intra-tumoral injection of STINGel dramatically improves efficacy over CDN alone in a challenging preclinical model of head and neck cancer and provides durable protection even against tumor re-challenge.

Moreover, the inventors anticipate that three designed MDPs will have different release rates based on their charge and binding chemistry (as shown in FIG. 3A). They expect cell viability of MOC1, MOC2 and MOC-2-E6E7 to be relatively high suggesting that inherent cell toxicity of the STINGels is not a significant contributing factor to efficacy. Results from un-loaded Lys-MDP confirms this (FIG. 3C-E). In vivo cell recruitment is expected to show strong recruitment of leukocytes with a significant population of antigen presenting cells and dendritic cells in particular. FIG. 3B shows that, in the case of un-loaded Lys-MDP, the inventors observe 13.5% $CD45^+/CD11b^+/CD11c^+$ dendritic cells three days after subcutaneous injection. The completion of this data for the other MDPs and collagen control will give a solid foundation in understanding CDN release profile, innate cytotoxicity and cell recruitment of STINGel.

Example 3—Materials and Methods

Figure 10A:
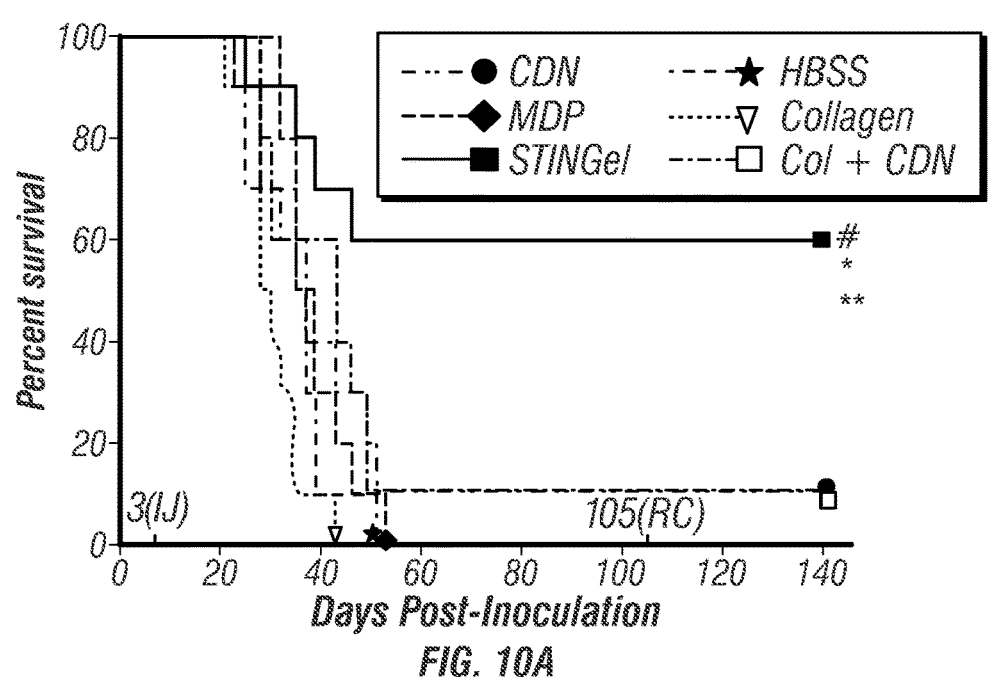
FIGS. 10A-C.
Figures 10B, 10C, 11:
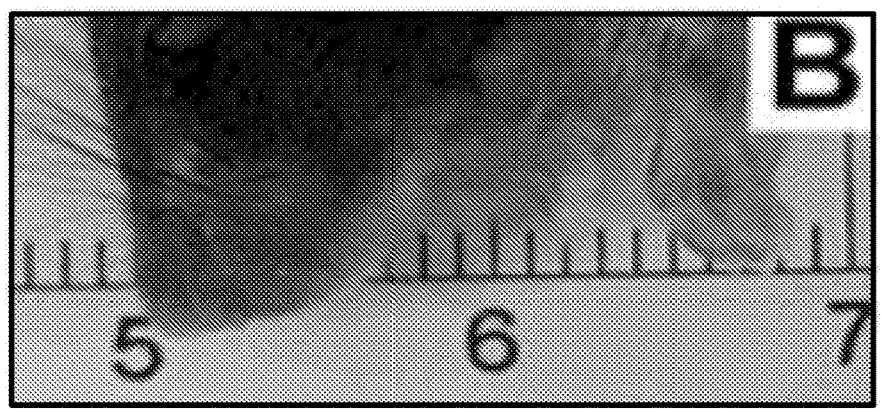
FIG. 11. MALDI-TOF MS of MDP $K_2(SL)_6K_2$ (SEQ ID NO: 1) purified peptide (amidated C-terminus, acetylated M-terminus). Expected mass is 1772.103 g/mol. The peak around 1660 g/mol is a small leucine deletion.

Peptide synthesis. Peptide synthesis reagents were purchased from EMD Chemicals (Philadelphia, PA). An Apex Focus XC (Aapptec) synthesizer was used to synthesize the multidomain peptide $K_2(SL)_6K_2$ (SEQ ID NO: 1) (MW=1773.171 g/mol) according to a standard synthetic method previously published to yield pure peptide with acetylated N-terminus and C-terminal amide (Aulisa et al., 2009; Li et al., 2016; Dong et al., 2007). All peptides were analyzed by Autoflex MALDI-TOF MS (Bruker Instruments, Billerica, MA) for purity and confirmation of successful synthesis (FIG. 11).

Hydrogel preparation and loading. All chemicals not otherwise specified were purchased from Sigma-Aldrich (St. Louis, MO). For preparation of sterile MDP stock solutions, 2 wt % (11 mM) peptide solutions were dissolved in 298 mM sucrose to support cytocompatibility. Stock ML RR-S2 CDA (CDN) (InvivoGen, San Diego, CA and MedChem Express, Monmouth Junction, NJ) was prepared at 2.67 µg/µL in endotoxin-free $H_2O$ (3.64 mM, 4× the final dose of 0.67 µg/µL, or 20 µg in 30 µL of gel), with concentration confirmed by UV-Vis. For preparation of control collagen gel formulations, a stock was prepared at 6.67 µg/µL CDN (10×). Collagen gel formulations were prepared according to the provided kit protocol (ECM675, EMD Millipore, Temecula, CA) with the substitution of CDN stock in DPBS (Thermo Scientific, Rockford, IL). The collagen stock solutions were provided at a concentration of 3.5-5.0 mg/mL varying by batch. Final collagen formulations were 1×DPBS, 80% v/v collagen stock solution (approximately 3-4 mg/mL), and 1×CDN (20 µg/30 µL). Collagen formulations were kept on ice prior to injections to maintain liquid state (gelation occurring at in vivo temperatures). STINGel formulations were prepared by diluting 4×CDN stock in an equal volume of 2×HBSS (Fisher Scientific, Hampton, NH), which was mixed with sterile 2 wt. % MDP in 298 mM sucrose to induce gelation. After mixing, final STINGel concentrations were 0.5×HBSS, 149 mM sucrose, 1 wt. % peptide (5.6 mM), and 1×CDN (20 µg/30 µL). All other controls were prepared with the same concentrations of HBSS and sucrose. For in vivo studies, prepared controls and gel formulations were loaded into Monoject 300 µL Insulin syringes (Covidien, Mansfield, MA) and allowed to equilibrate for ~1 hour before injection.

CDN drug release kinetics. To study the kinetics of CDN release from STINGel vs. collagen gel, 30 µL CDN-loaded gel aliquots were deposited into Falcon® 96 well flat bottom polystyrene plates (Becton Dickinson Labware, Franklin Lakes, NJ). For each experiment, cylindrical pucks of the 30 µL gel aliquots were created in each well, allowing the pipetted gels to shear recover for at least 5 mM before adding 200 µL of buffer (1×HBSS for STINGel, 1x DPBS for collagen, according to gelation requirements) to the top of the gels at what was defined as t=0 for the start of kinetics experiments. The buffer height was approximately 2.5 mm, the gel thickness approximately 0.5 mm, and the gel's solvent exposed surface area approximately 12.6 $mm^2$.

A Thermo Scientific Nanodrop 2000C Spectrophotometer was used to measure UV absorbance at 259 nm, the characteristic wavelength of maximum absorbance for the CDN's adenine nucleobases. An extinction coefficient of 24,000 $M^{-1}$ $cm^{-1}$ at 259 nm was used. Absorbance measurements were taken by removal of 1 µL aliquots from the surface of the buffers, measuring the increase in absorbance over time. Release of CDN was measured over the course of the first 24 hours and converted to total percent released, with additional measurements also made at 48 and 72 hours to confirm that the samples had reached equilibrium.

Cell culture. MOC2-E6E7, the murine oral cancer cell line used in this study, was generated by retroviral transduction of HPV16 E6E7 in MOC2 cells (Young et al., 2017a; 2017b). MOC2 cells were provided by Dr. Ravindra Uppaluri, Dana-Farber Cancer Institute, Harvard University, Boston. MOC2-E6E7 cells were maintained in presence of 4 mg/mL puromycin dihydrochloride in medium routinely used for maintaining MOC2 (Judd et al., 2012). Cells were used at 80-95% confluency for all experiments.

Preparation of cell—laden hydrogel for in vitro viability. MDP gel formulations with MOC2-E6E7 cells were prepared by diluting a cell suspension of 2,000,000 cells/mL in 2×HBSS with an equal volume of 4×CDN. The resulting suspension was then added to an equal volume of sterile 2 wt. % peptide in 298 mM sucrose and mixed to produce final samples of approximately 35,000 cells per 70 µL of 1 wt. %, 149 mM sucrose gel. Gels were then transferred into 0.4 cm 2 wells of Lab-Tek 16 well glass chamber slides (Thermo Fischer, Rochester, NY), pipetted to produce 70 µL pucks with flat profiles. Samples were allowed to shear recover for 5-10 mM before adding 200 µL cell media on top of each gel. The cell media was changed every 2 days, taking care to not dislodge the hydrogel material.

Cell viability was determined at each desired time point by performing live/dead assays as described below. Live/dead staining solution was prepared in DPBS with 2 µM Calcein AM for live cells (Life Technologies), 4 µM Ethidium homodimer for dead cells (Life Technologies), and 5 µg/mL Hoechst 33342 for nuclei (MP Biomedicals, Solon, OH). In many cases significant background staining of the hydrogels resulted in reduced resolution of the blue Hoechst channel in confocal images. Cell media was removed and the gels were washed with PBS. Samples were then stained with 100 µL of prepared solution by incubating at RT for 15-30 mM. Following staining, gels were placed in PBS for immediate analysis by confocal microscopy. Gels were analyzed by z-stack imaging (100 µm) using a Nikon A1 Confocal Microscope with 20× air and 40× water objectives (405 nm blue channel laser, 488 nm green channel laser, 561 nm red channel laser). Image processing was done using NIS Elements, and live/dead cell counting was performed using the cell identification tool in Imaris 3D/4D Image Processing software, manually verified with nuclear counts when resolution allowed.

Subcutaneous experiments and histology. Male/female mice (C57BL/6 strain) of age 8-12 weeks were obtained for subcutaneous experiments, which were conducted with Rice IACUC approval and according to NIH guidelines. Mice were injected with 40 µL CDN-loaded hydrogel (910 µM CDN) or 100 µL unloaded hydrogel in each of four separate sites in the subcutaneous space of the dorsal flank. At days 3 and 7 the mice were euthanized and the dorsal skin around the entire implant was removed, fixed overnight in 10% neutral buffered formalin, processed and paraffin embedded by the Baylor College of Medicine Pathology Core, and finally sectioned at 5 µm thickness for Masson's trichrome staining and hematoxylin and eosin (H&E) staining (FIGS. 14A-F and 16A-F).

Tumor growth and survival study. For tumor experiments, 6-8 week old wild-type C57BL/6 female mice were maintained in a pathogen-free environment for the study. All protocols were in accordance with the guidelines for humane treatment of laboratory animals by the National Institutes of Health, the Animal Welfare Committee and the Center for Laboratory Animal Medicine and Care (CLAMC) at the University of Texas Health Science Center at Houston. Mice were injected with MOC2-E6E7 tumor cells on day 0 into the maxillary oral vestibule (30,000 cells in 30 µL volume), followed by controls or gel injections loaded with or without CDN on day 3 in the same oral cavity location (20 lag CDN per 30 µL injection). Tumor growth was measured using calipers and body weight was taken in all subjects two to three times per week. Photographs were also obtained. Kaplan-Meier survival and tumor growth curve analyses were performed from data obtained. Mice that maintained tumor clearance for 100 days were re-challenged with MOC2-E6E7 tumor cells again at day 105 and monitored similarly. All endpoints in tumor growth curve and survival data are a result of euthanasia due to excessive tumor burden, defined as tumor reaching 12 mm, tumor ulceration, or a weight loss of greater than 20%. The inventors observed no signs of unexpected disease or discomfort in the mice over the course of the experiments.

Statistical methods. Statistical analyses for Kaplan-Meier survival curves were performed using the log-rank/Mantel-Cox test with GraphPad Prism (GraphPad, San Diego, CA). For tumor growth curves, the Wilcoxon rank sum test was used to compare tumor size between STINGel and other groups. No adjustment for multiple testing was made because the study is novel and exploratory. All p values are two-sided and p values less than 0.05 were considered as significant. All statistical analyses were performed using the SAS software (version 9.4, the SAS Institute, Cary, NC).

Example 4—Results

Hydrogel properties and drug release kinetics. In this study, the inventors sought to use a MDP hydrogel with sequence $K_2(SL)_6K_2$ (SEQ ID NO: 1) to deliver a promising STING agonist CDN, by taking advantage of favorable electrostatic interactions between the CDN's negative thiophosphate linkages and the positive lysine residues at the peptide termini (FIGS. 4A-D). They hypothesized that a combination of controlled release and favorable local environment would result in improved tumor treatment efficacy in vivo.

Figure 5A:
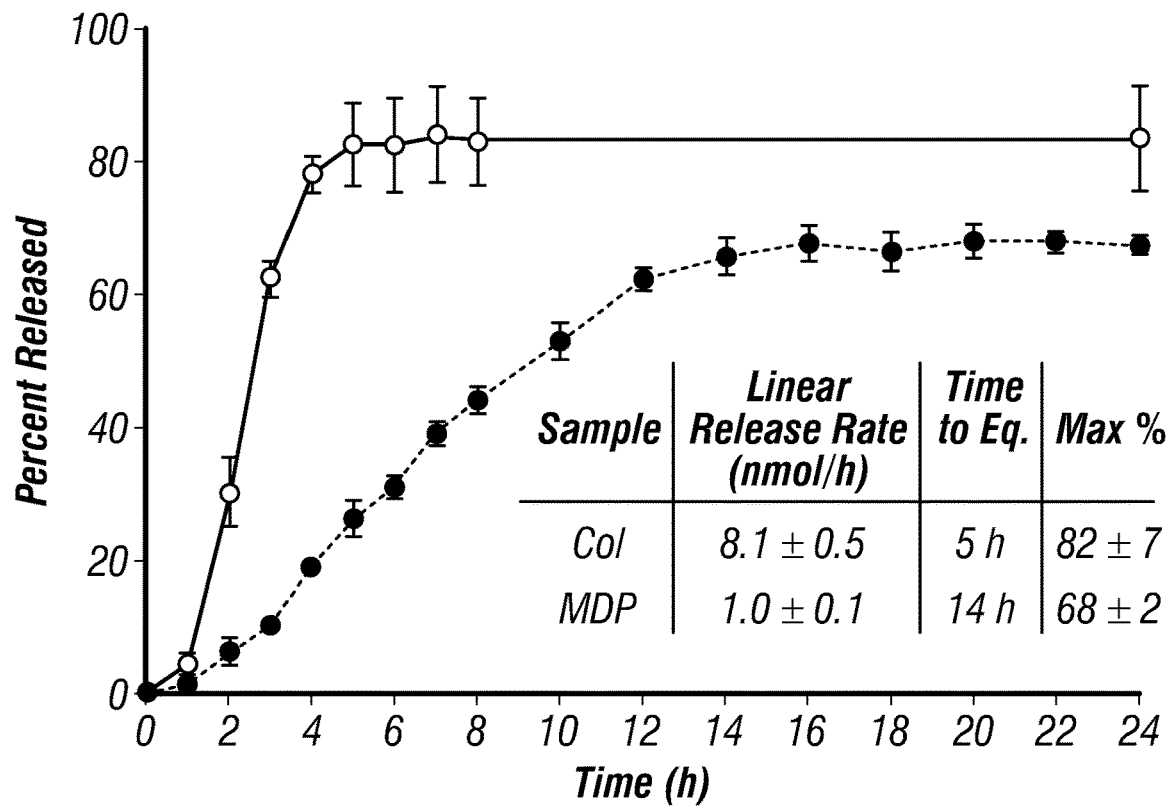
FIGS. 5A-B.
Figure 5B:
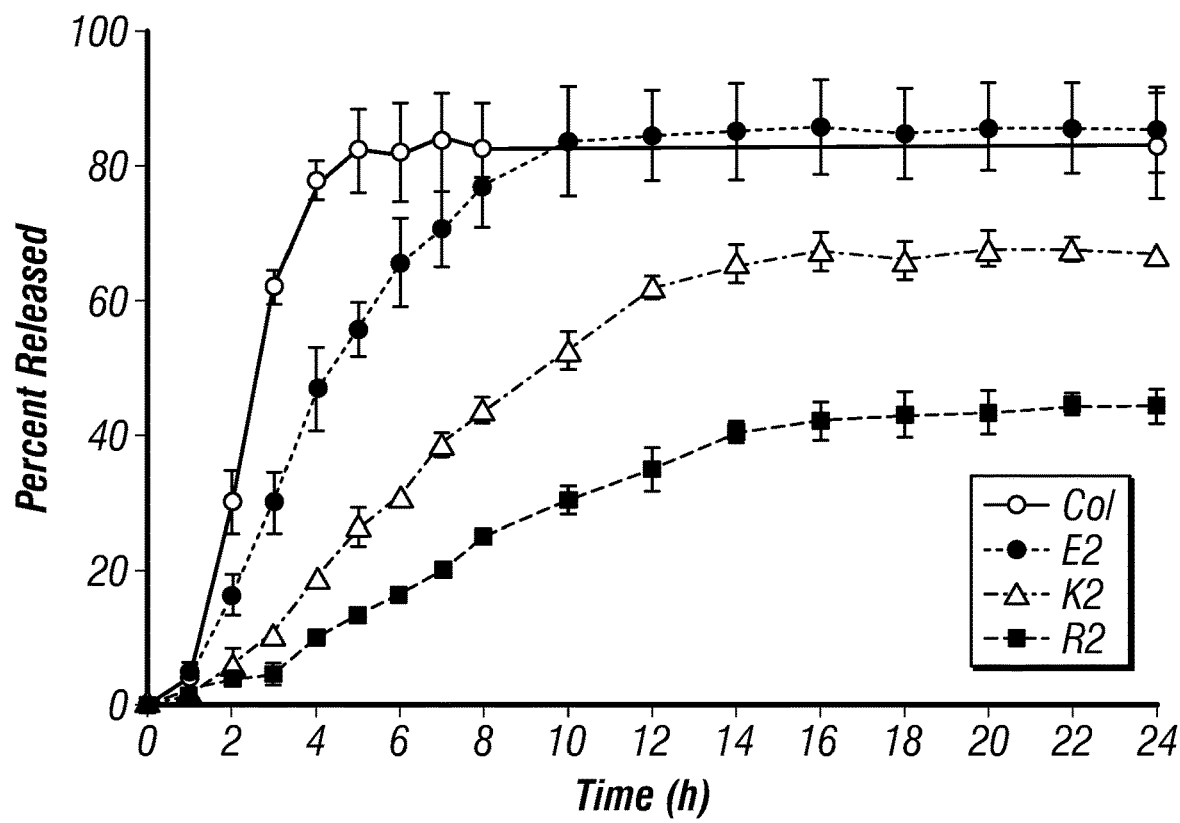

The MDP hydrogel $K_2(SL)_6K_2$ (SEQ ID NO: 1), extensively characterized in past studies in terms of peptide secondary structure, nanostructure, rheological properties, and biocompatibility, was examined in the context of this experiment for its ability to encapsulate and deliver the small molecule CDN (Moore et al., 2017; Aulisa et al., 2009; Kumar et al., 2015a) crosslinking of MDP fibers to achieve drug loading was previously accomplished with the negatively charged anti-parasitic compound suramin, and thus the inventors' work with CDN was a natural extension (Kumar et al. 2015a). As shown in FIG. 5, release profiles of CDN from MDP hydrogel and a collagen control hydrogel were obtained by detecting the released drug concentration via UV-Vis. Over time the solvent-exposed surface area of the hydrogels allowed for free exchange of CDN with the surroundings until an equilibrium had been achieved. This equilibrium was observable when a maximum and unchanging concentration of CDN was recorded over multiple time points.

FIG. 5 shows that controlled release of CDN was achieved, with a factor of 8 decrease in release rate for the highly positively charged MDP hydrogel compared to collagen control gels. Collagen gels showed a release rate of approximately 8.1 nmol CDN/hour in the initial linear release phase, compared to only 1.0 nmol CDN/hour from MDP gels. Indeed, the release profiles show that in this system, within 4-5 hours collagen gels have fully released CDN and reached the maximum theoretical equilibrium with the surrounding buffer (approximately 85%). In contrast, not only do the kinetics profiles of MDP hydrogel show 14-15 hour continuous release in this system, but they also plateau at a significantly lower maximum release of loaded CDN at approximately 68%. This suggests that the material, presumably as a result of ion-ion charge-pair interactions between negative drug molecules and positive peptide nanofibers, reaches a different chemical equilibrium with the surrounding buffer system, thereby withholding more CDN until the equilibrium is disturbed. This equilibrium can be disturbed by exchanging the buffer in long release studies, or by fluid flow in vivo. As this is the basis of the designed controlled release mechanism, a lower equilibrium is an expected result, and supports the inventors' conclusion that extended release was successfully achieved in STINGel (MDP+CDN).

Figure 6A:
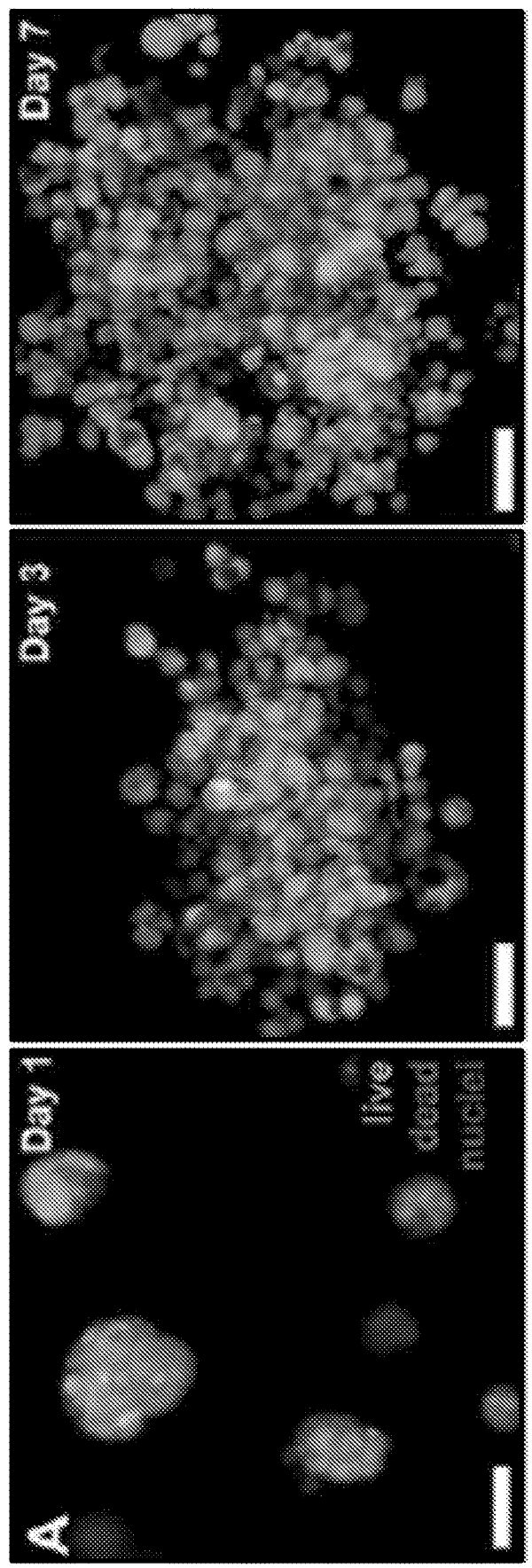
FIGS. 6A-B. Cell viability in unloaded and loaded MDP hydrogel. MOC2-E6E7 cells were seeded at a density of approximately 35,000 cells within 70 μL of gel under 200 μL of media (changed every two days) and processed under Live/Dead viability assays (green-live cells; red-dead cells; blue-nuclei).
Figure 7:
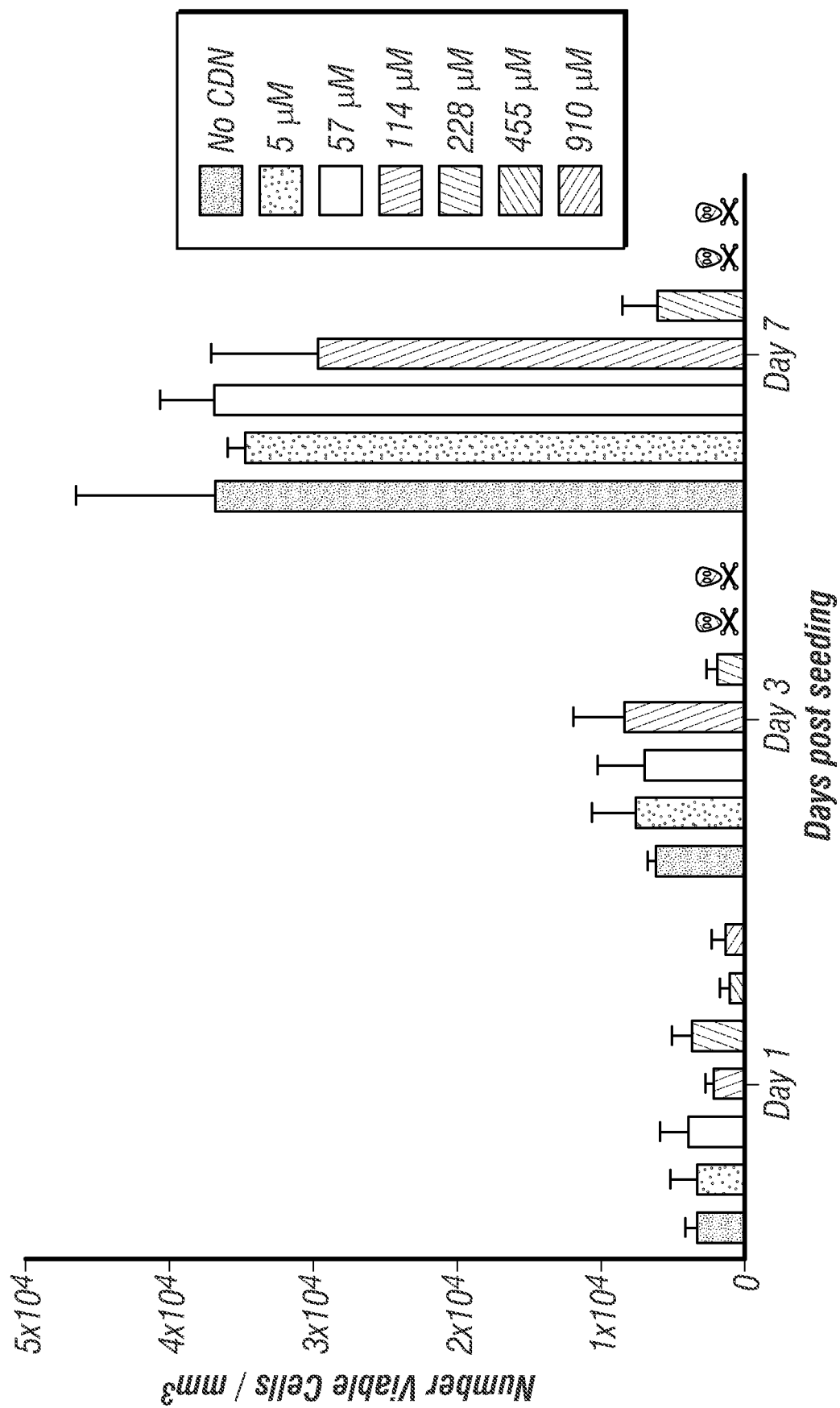
FIG. 7. Live/dead viability assay quantification used to assess CDN toxicity to MOC2-E6E7 cells. The graph shows the number of viable cells per $mm^3$ of hydrogel over days 1-7 post seeding with cells, testing increasing concentrations of CDN loaded into the MDP hydrogel. The ⚰ symbols refers to >99% cell death. Values represent the mean and standard deviation in all plots (n=3). Key showing top to bottom correlates to left to right in figure.
Figure 12A:
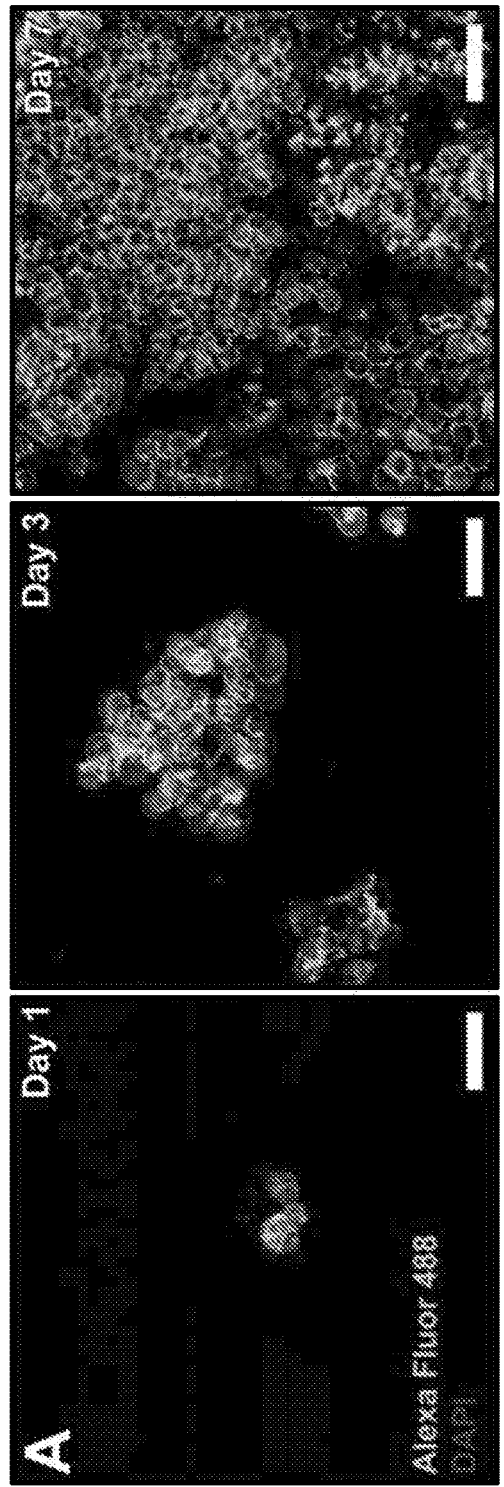
FIGS. 12A-B. Cell proliferation study of MOC2-E6E7 cells seeded (FIG. 12A) in 2D on the surface of MDP unloaded hydrogel, (FIG. 12B) in 3D within MDP hydrogel (all in the absence of CDN). For 2-D, cells were seeded at a density of approximately 500 cells on the surface of a 70 μL gel puck, and started as small clumps that grew over time into wide-spread colonies over the whole surface of the gel. For 3-D, cells were seeded at a density of approximately 35,000 cells in 70 μL of gel, and started as small clumps that grew over time into large tumor-like colonies within the gel. Stains are Alexa Fluor 488 phalloidin for cytoskeleton, and DAPI for cell nuclei. Scale bars are 50 μm.
Figure 12B:
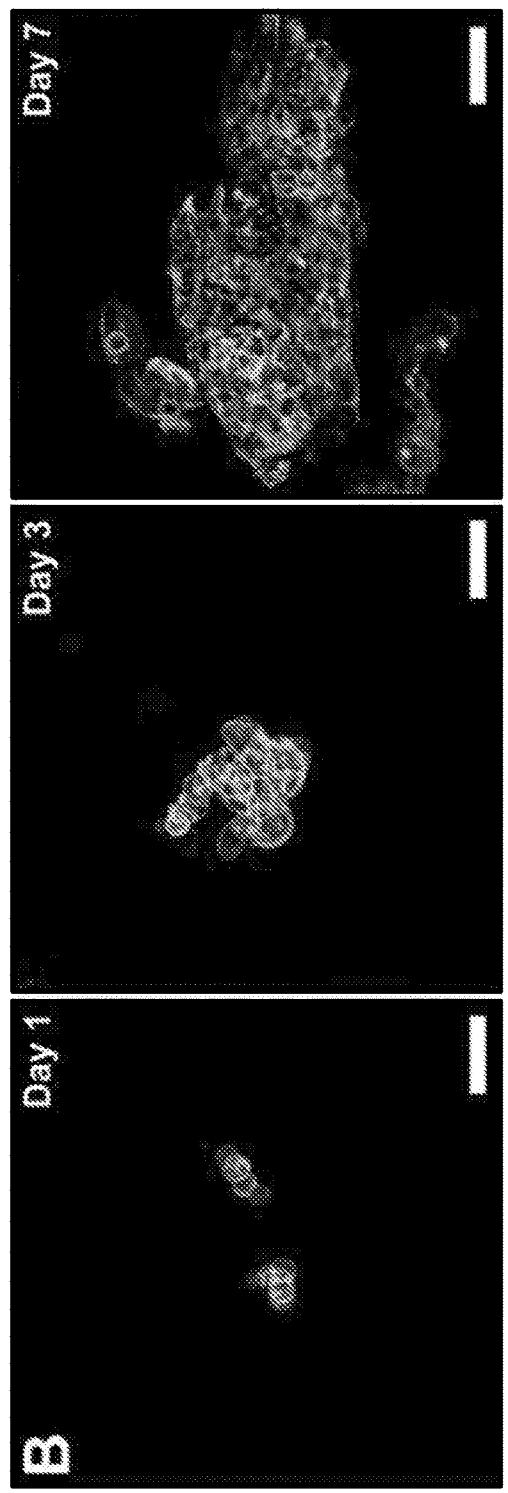

In vitro cell viability. In order to determine the cytocompatibility of the STINGel material with the murine oral cancer cell line MOC2-E6E7, the inventors assessed in vitro cell viability by live/dead staining to visualize and quantify cell survival in their gels. MOC2-E6E7 cells suspended in 3-D gels of unloaded MDP hydrogel controls showed results consistent with all the inventors' previous work: cells are able to survive and proliferate within the 3-D hydrogel matrix, exchanging waste and nutrients with the surrounding buffer and remodeling the peptide hydrogel to allow for larger colonies (Moore et al., 2017). Control experiments are shown in FIG. 6A surveyed at 20× magnification by confocal microscopy, where the cancer cells are seeded as small clumps within hydrogel pucks and placed under media for 7 days. The inventors observed the cells grow from discrete groups of around 3-10 cells distributed throughout the hydrogel matrix, to larger clumps of hundreds of cells by day 7 in the absence of CDN (similar proliferation results shown for MDP controls in FIGS. 12A-B). FIG. 7 shows the mean cell counts and quantification of cell density within the gels.

Figure 6B:
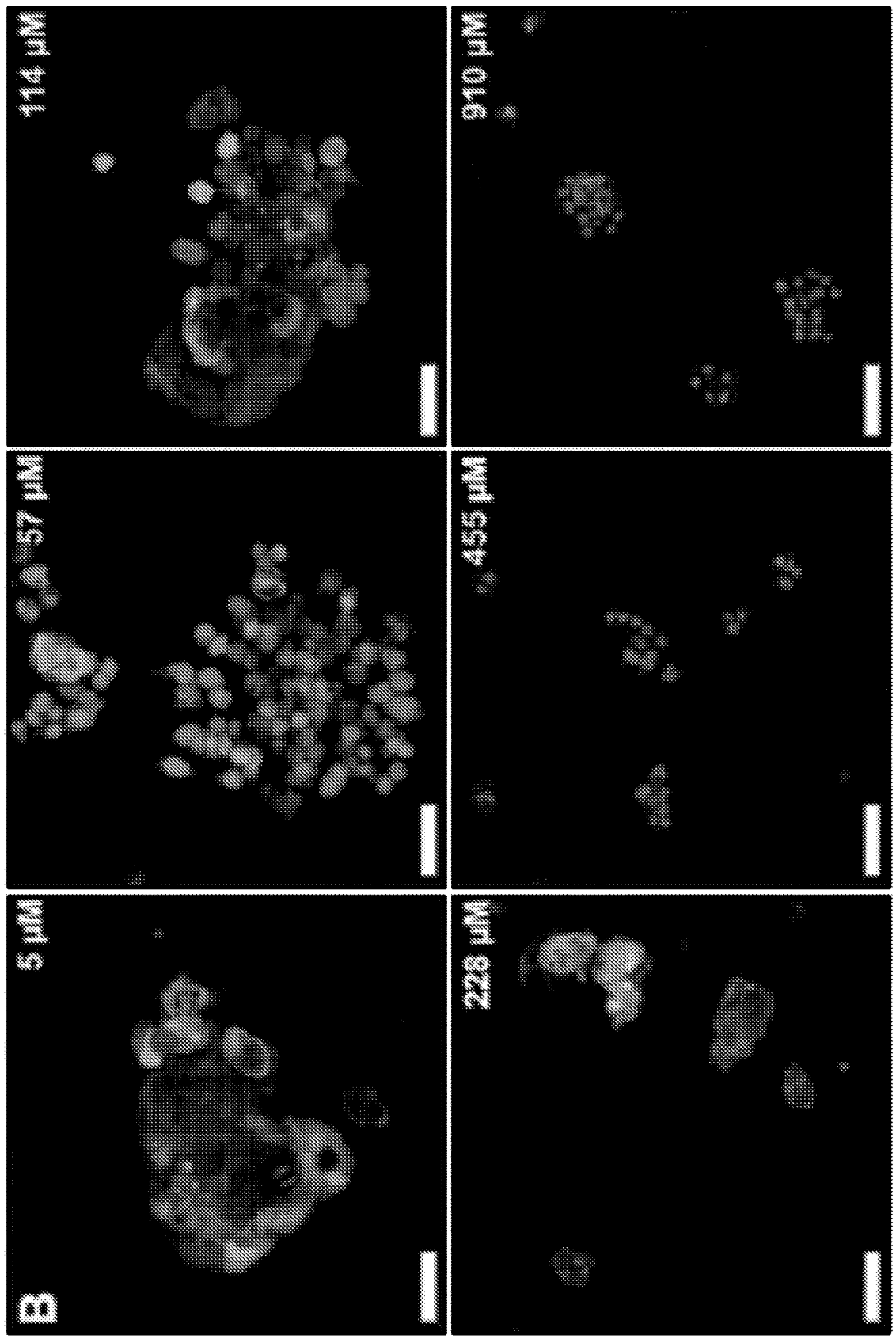
Figure 13A:
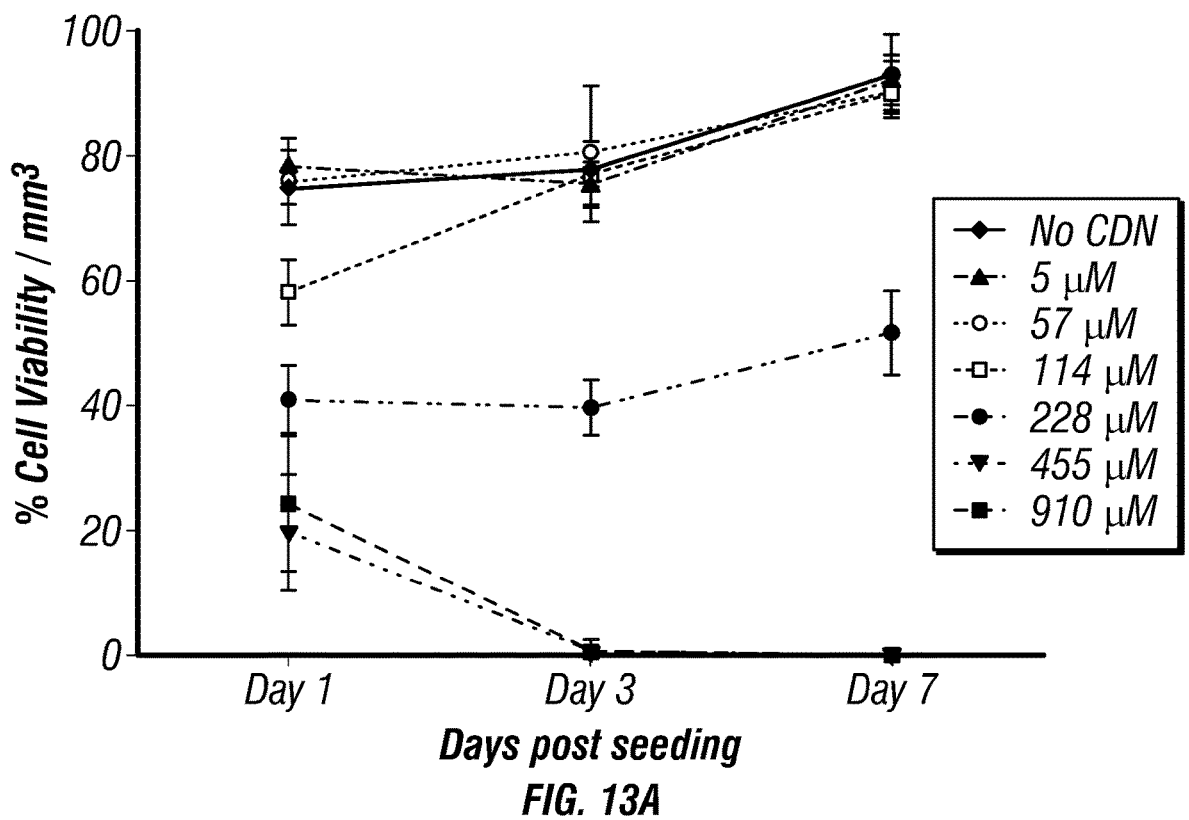
FIGS. 13A-B. Live/dead viability assay quantification.
Figure 13B:
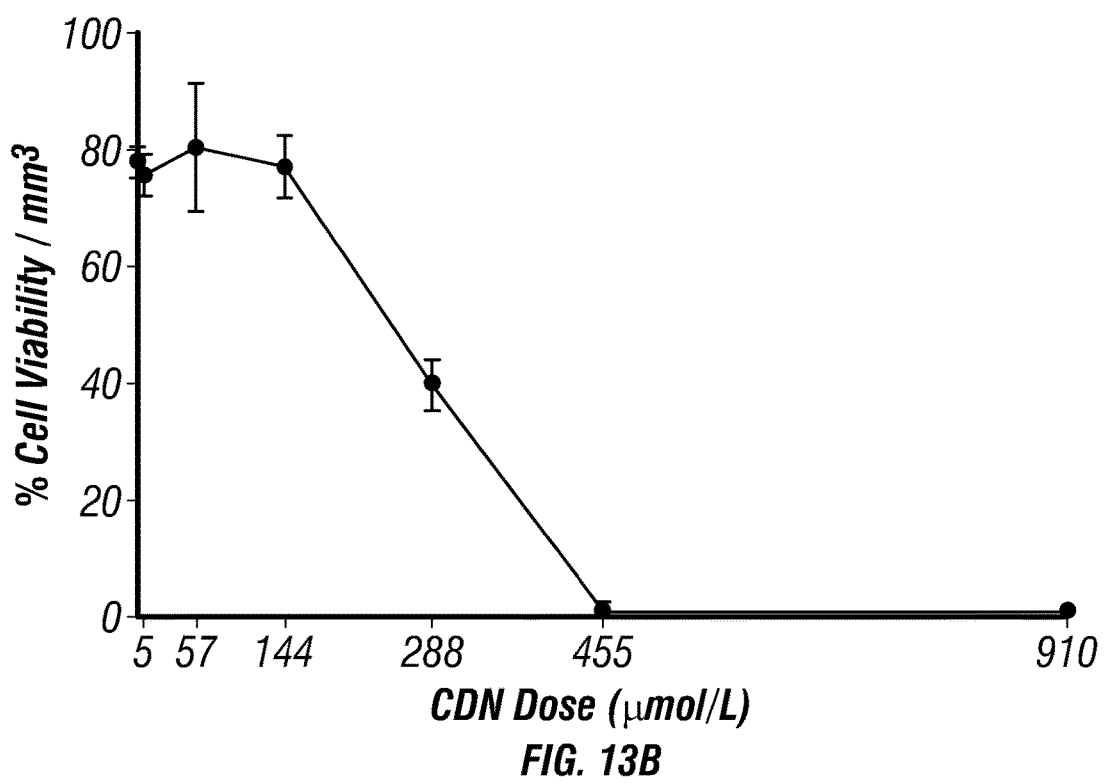
Figure 14C:
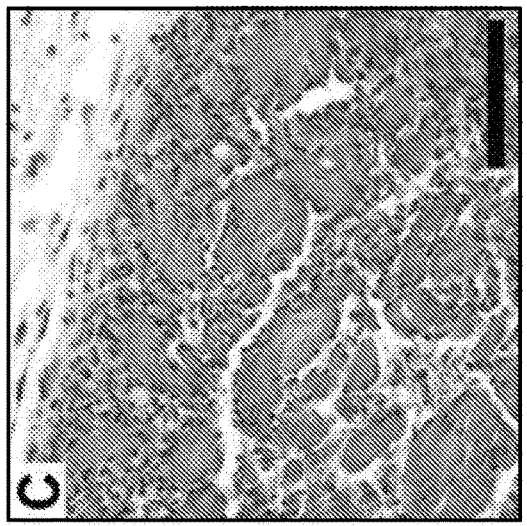
FIGS. 14A-F. H&E stained MDP peptide hydrogel implant unloaded and loaded with CDN, injected subcutaneously in mice. Time point shown is 3 days post injection, at which time hydrogel implant was removed and processed for histology. 4× scale bars in FIGS. 14A and 14D are 1 mm; 40× scale bars in FIGS. 14B, 14C, 14E, and 14F are 0.1 mm (FIGS. 14A-C) MDP control implant at 4× magnification showing even infiltration of cells, with boxes drawn around relevant areas whose 40× counterparts are shown in FIGS. 14B and 14C, respectively.
Figure 14B:
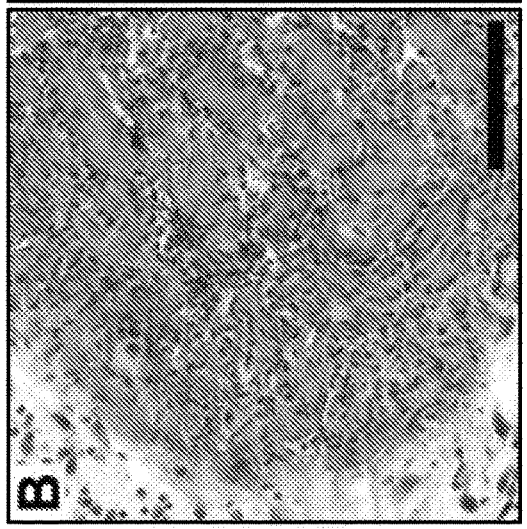
Figure 14A:
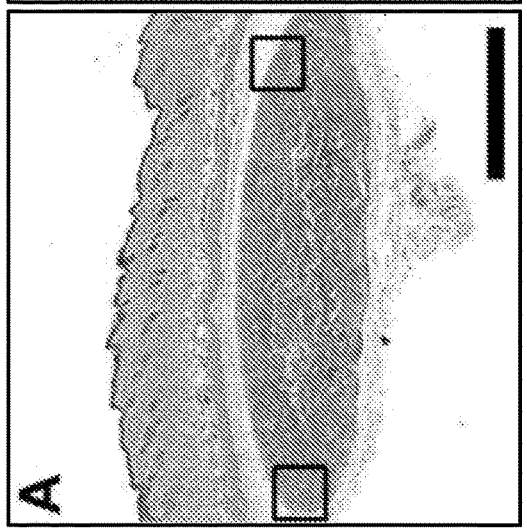
Figure 14F:
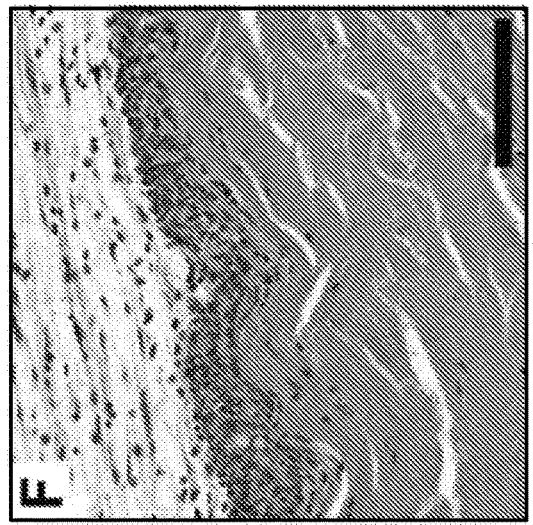
Figure 14E:
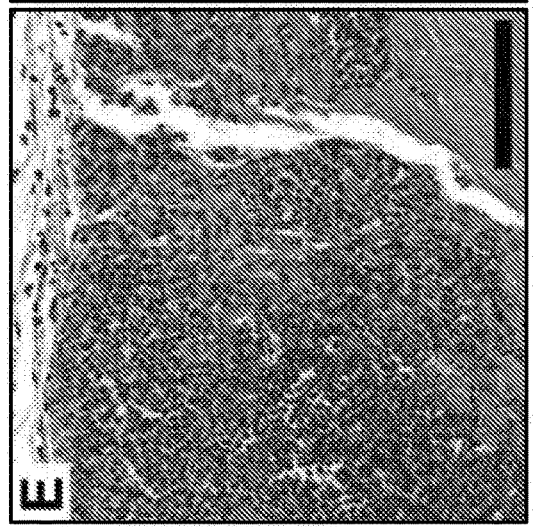
Figure 14D:
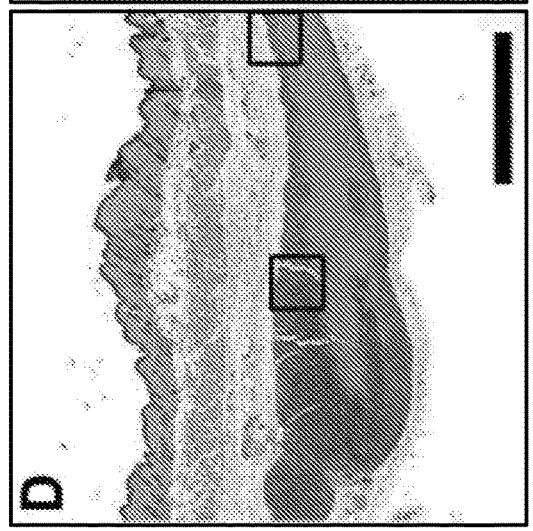
Figure 17C:
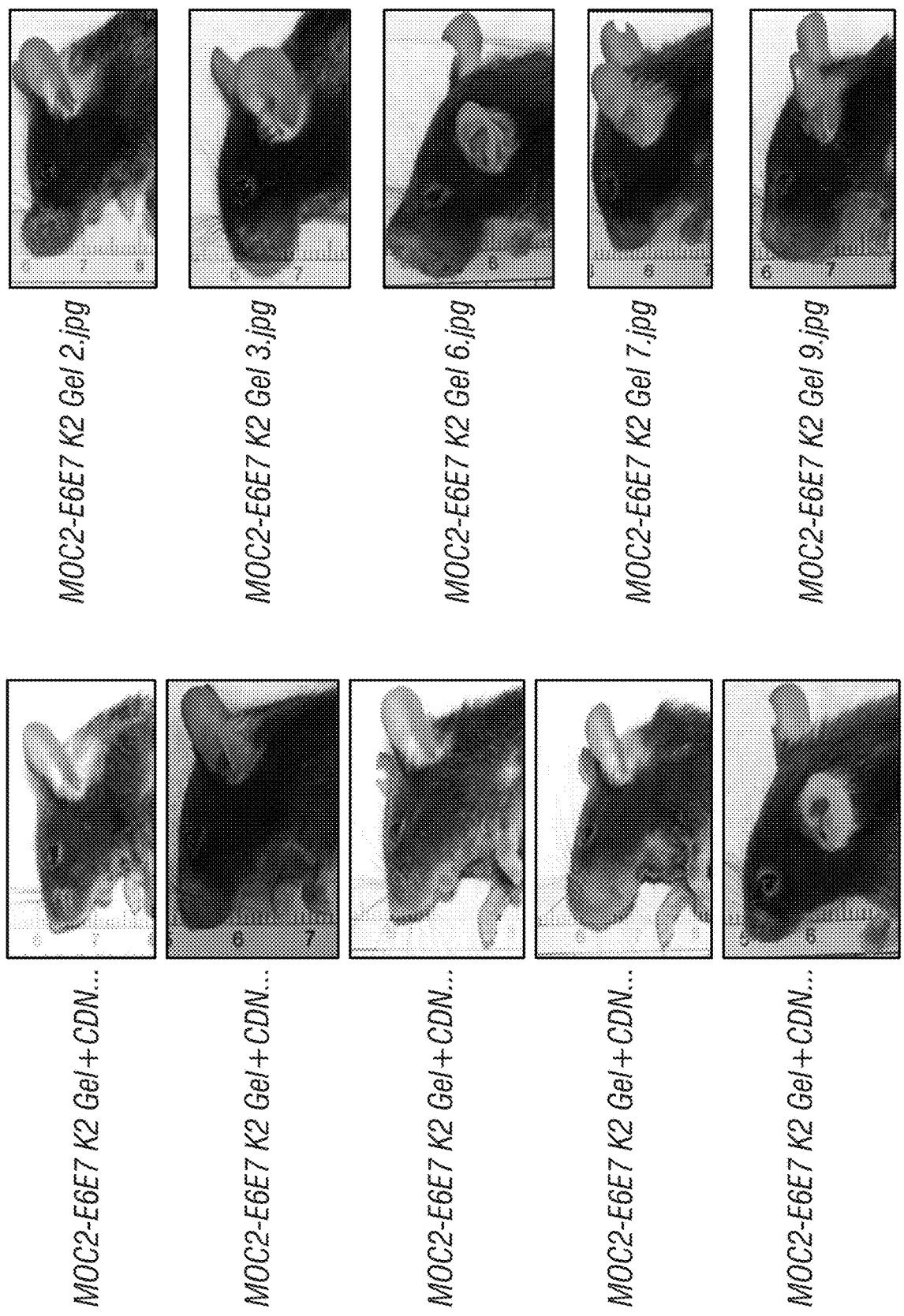

In contrast, increasing STINGel formulations (MDP loaded with 228, 455 and 910 µM CDN), resulted in significant cell death (FIG. 6B). While no difference in cell growth (FIG. 7) or percent viability (FIGS. 13A-B) was observed in samples loaded with 5 µM and 57 µM CDN (typical in vitro concentrations for induction of STING pathway and Type 1 INF expression; Moore et al., 2016), observable cell stress, seen as a difference in percent cell viability shown in FIGS. 13A-B, was observed even at 114 µM CDN at the day 1 timepoint. However, cells seeded in 114 µM CDN gels recover to normal levels of viability and growth by days 3 and 7 (FIG. 7; FIGS. 13A-B). Significant cell death and inhibition of cell growth was observed at 228 µM, with cell counts largely reduced from controls even as late as day 7 in FIG. 7. Massive cell death was observed at 455 and 910 µM (the concentration of in vivo injections) such that cell viability approached 0% by day 3 post seeding. In summary, while unloaded MDP gel is fully biocompatible, CDN loaded MDP gel exhibited inherent cytotoxicity at high drug concentrations in vitro.

In vivo subcutaneous characterization. In order to assess the properties of the STINGel material in vivo, the host response was studied using subcutaneous injections in mice. At specific timepoints the mice were euthanized and the implants removed for histological analysis (FIGS. 8A-F, FIGS. 14A-F, 15A-F and 16A-F). Injection volumes were chosen to be 40 µL for CDN-loaded hydrogels and 100 µL for unloaded hydrogels. In past work, 100 µL or greater was an ideal injection volume as it aided in the location and removal of the hydrogel implants (Kumar et al., 2016; Kumar et al., 2015b). However, in the case of drug-loaded injections, the inventors had to make a compromise between the implant being large enough to be visible by 3-7 days post injection, but also small enough for the total CDN dose to be well below potentially toxic levels. Therefore 40 µL was chosen and found to be sufficient for the inventors' purposes, with no signs of systemic toxicity observed in any experiments.

Masson's trichrome staining shows the hydrogel implants as purple-red oblong ovals in the mouse hypodermis, contrasting to the blue natural collagen and dark red muscle (FIGS. 8A-F and FIGS. 15A-F), while H&E staining shows the hydrogel as well-defined eosinophilic (pink) material in the subcutaneous space (FIGS. 14A-F and 16A-F). Uniform cellular infiltration of the control unloaded MDP implant without fibrous encapsulation was observed, a result consistent with all prior subcutaneous experiments performed with MDP hydrogels (FIGS. 8A-C) (Moore et al., 2016; Kumar et al., 2015b). At day 3 almost the entirety of the unloaded implant is observed to be infiltrated by inflammatory cells that rim the hydrogel material, resembling histologic features commonly seen in a foreign body reaction. By visual evaluation, many of these cells are likely monocytes trying to engulf the foreign hydrogel material. However, in contrast are CDN drug-loaded implants, which show substantially increased inflammatory condensation along the periphery of the hydrogel (FIGS. 8D-F). Unlike the unloaded hydrogel, the infiltrating immune cells in CDN-loaded implants are much denser and encompass a high proportion of what appear to be lymphocytes (FIGS. 8E-F). By day 7, cell infiltration of CDN-loaded hydrogels increases, presumably as CDN concentration in the implants fell below the toxic thresholds observed in cell culture (FIGS. 15A-F and 16A-F). However, CDN-loaded implants still did not reach the uniform cellular infiltration observed in unloaded controls, providing evidence of continuous immune-cell chemotaxis that is sustained by the inventors' slow release system.

Figure 9A:
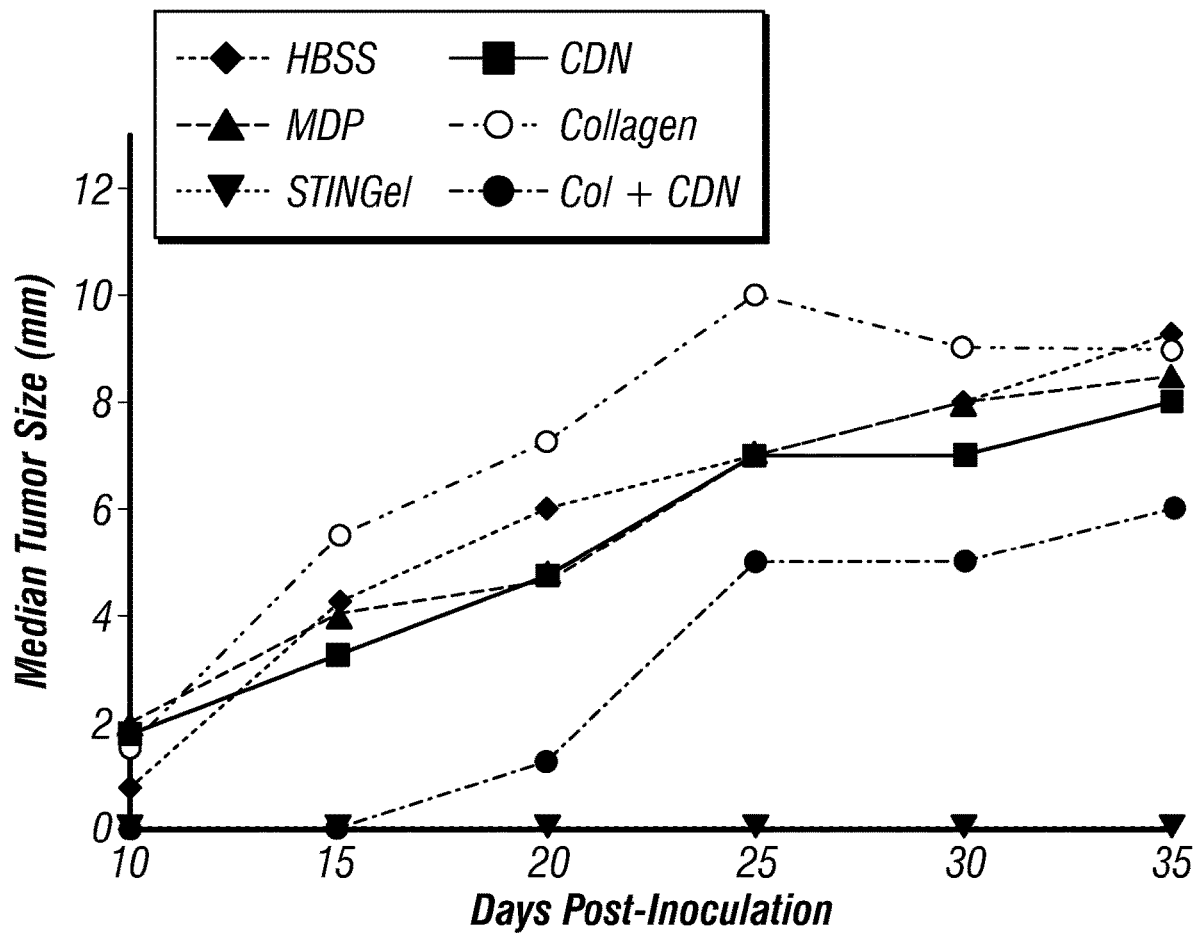
FIGS. 9A-G. Tumor growth curves in controls and STINGel treated animals (n=10 per treatment group).
Figure 9B:
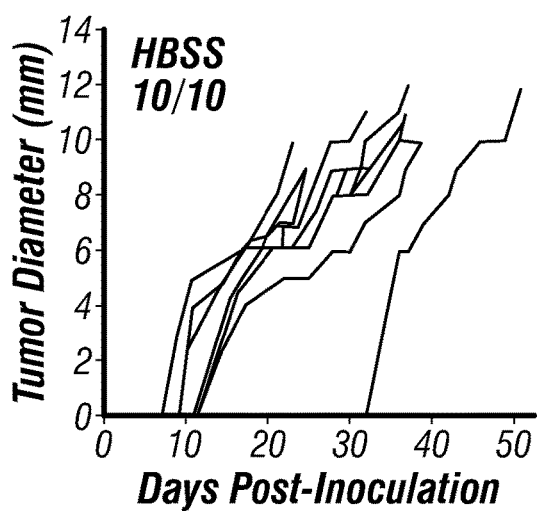
Figure 9C:
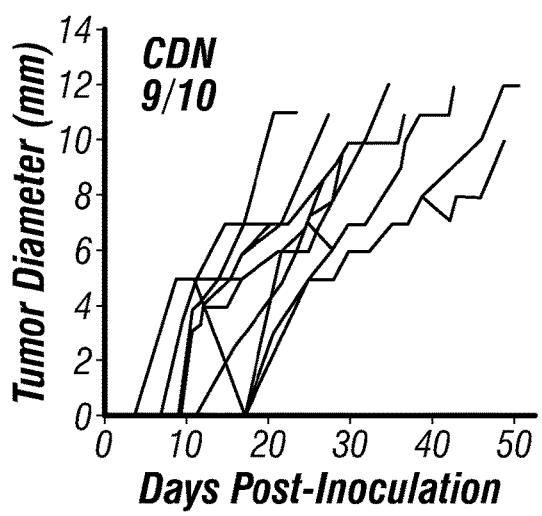
Figure 9D:
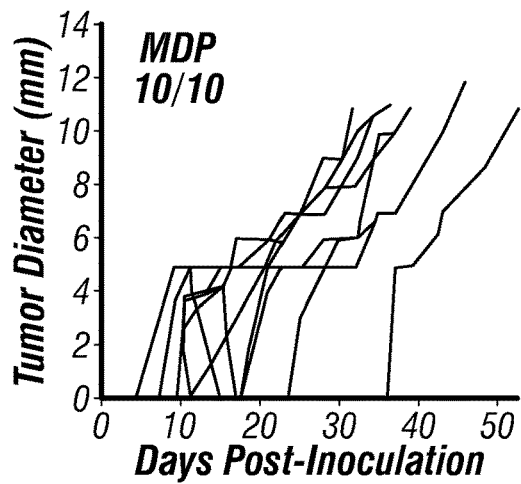
Figure 9E:
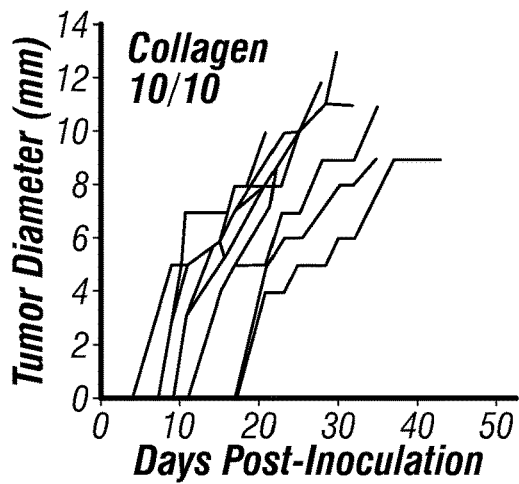
Figure 9F:
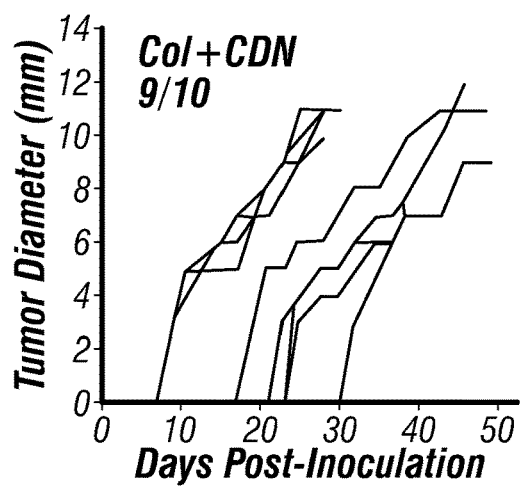
Figure 9G:
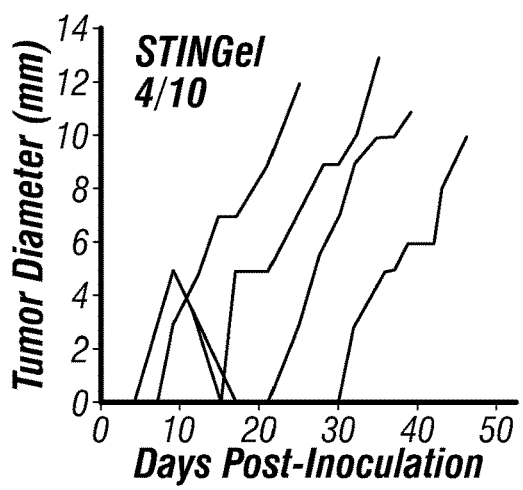

In vivo murine experiments: STINGel induced rejection of MOC2-E6E7 tumors. The inventors examined the growth of MOC2-E6E7 tumors in mice treated with HBSS, CDN alone, MDP gel, STINGel (MDP+CDN), collagen or collagen+CDN to determine antitumor efficacy. They observed no signs of systemic toxicity after treatment administration, nor signs of unexpected disease or discomfort in the mice over the course of the experiments. Treatments with STINGel show a significant decrease in tumor growth, or a complete tumor clearance compared to other groups (FIG. 9A). Median (FIG. 9A) and individual (FIGS. 9B-E) tumor growth curves for treatment groups compared to HBSS control show that treatments with STINGel extend the period of progression-free disease (FIG. 9D). Although tumor growth in mice treated with collagen+CDN (FIG. 9F) show similar initial periods of progression-free disease as STINGel, 90% of mice develop tumors. The data represented in FIGS. 9A-G has been determined from tumor dimensions collected from day 10-day 35 as median tumor size. Mice that maintained tumor clearance were rechallenged with a second tumor cell inoculation of MOC2-E6E7 cells at day 105 after initial inoculation. 6 out of 10 STINGel mice were able to reach this reinoculation point. On the contrary, only 1 in 10 CDN and collagen+CDN mice reached this point. All animals surviving to day 105 survived a second tumor inoculation to day 140 without showing any signs of tumor growth The Kaplan-Meier survival curve (FIGS. 10A-C) shows survival of mice from all six treatment groups, HBSS, CDN, MDP gel, STINGel, collagen or collagen+CDN based upon the time of euthanasia defined as tumors reaching 12 mm and a weight loss of 20%. In some instances, tumors reached up to 14 mm and did not have a weight loss of 20%. Treatments with STINGel resulted in a prolonged-disease free survival state and had the most number of survivors, 6/10 mice. Thus, the inventors conclude that treatment with STINGel shows considerable antitumor efficacy.

Example 5—Discussion

The ability of biomaterials to allow for spatiotemporal control over payload delivery means diverse factors can be released in a controlled manner within a specific volume, reducing off-target toxicity while also enabling localized improvements in efficacy. Materials able to exploit such capabilities to release factors that can intelligently direct and modulate immune cells in situ are highly attractive, and thus the inventors sought to develop STINGel as such a platform to improve current immunotherapies.

Through the use of favorable electrostatic interactions between the positive lysine termini and negative thiophosphate linkages, controlled and extended release of CDN was achieved in MDP compared to a collagen control gel (FIG. 5). The data show that the MDP releases its payload significantly slower than a collagen hydrogel, thereby increasing the length of time spent at higher concentrations of CDN.

Cell viability obtained in vitro suggests that the initial concentration injected in vivo (910 µM) is strongly cytotoxic. This concentration was directly taken from the literature and previous studies that use CDN in vivo (Moore et al, 2016). The results suggest that one fourth of the initial concentration (228 µM) may be the max tolerable dose cells can experience in their local environment without the massive cell death observed at 455 µM and above (FIG. 6B). Even at 114 µM cells experience some initial stress and loss of viability, though at this concentration it is recoverable (FIG. 7). Thus, the in vitro data suggest that investigators may be injecting the STINGel material at a concentration that is initially toxic, and must decrease by almost a factor of 10 before it is no longer a direct threat to cell viability. CDN injected without gel or other delivery agent presumably diffuses away very rapidly and does not promote a lasting cytotoxic effect.

This aids in the interpretation of the subcutaneous histology, which shows a dramatic difference in cellular response to biomaterial loaded with CDN. At day 3, unloaded MDP shows an even dispersion of immune cells both rimming the hydrogel and thoroughly scattered in the inter-gel space (FIG. 8A). However, as described previously, CDN-loaded hydrogels show uneven cellular infiltration, and what appear to be dense pools of lymphocytes. Thus CDN-loading appears to substantially increase the chemotactic recruitment of a mixed population of inflammatory cells. Indeed, while large areas of the implant are non-infiltrated, with cells lining the edges, other areas of the hydrogel structure seem to be heavily disrupted by dense inflammatory infiltrate with substantial necrosis and nuclear debris (FIG. 8E). This observation is consistent with what was observed in vitro, that high CDN concentration resulted in significant cell death. Very high levels of Type I IFN activation is known to launch a transcriptional program that promotes cell death, which probably underpins CDN-induced cytotoxicity (Tamura et al., 2008; Lei et al., 2008). Cell death may well be a beneficial aspect of this system, for nuclear debris will release danger-associated molecular patterns (DAMPs) that can further exacerbate inflammation by recruiting more immune cells to the area (Klune et al., 2008; Bianchi, 2007). Although some cytotoxicity of immune cells is well-tolerated, which is also evidenced by the significant survival improvement upon STINGel treatment, further optimization of dosing and slow-release kinetics may further enhance the therapeutic potency.

The STINGel material appears to create and prolong a period of high, localized CDN concentration, discouraging cellular infiltration into a cytotoxic implant while also directly causing cell necrosis. This data indicates the material is injected at a high concentration and maintains this concentration for a significantly longer period of time than a collagen gel, due to the extended release of CDN and the lower equilibrium reached with the surrounding environment until diffusion carries CDN away. This promotion of cell death and lack of infiltration may be maintained until the concentration of CDN falls below a certain threshold (possibly around 114-228 µM). It is possible that at this point massive immune cell infiltration occurs (FIG. 8E). One possible explanation for this phenomenon is stimulation by CDN STING signaling (Barber, 2015; Burdette and Vance, 2013) and further exacerbation by DAMP release (Bianchi, 2007). These results shed light on the anti-tumor efficacy of STINGel seen in this murine oral cancer model (FIGS. 9A-10C).

The inventors have hypothesized that the mechanism of this system's efficacy is primarily spatiotemporal control over CDN delivery, in combination with exacerbation of the inflammation response by the inherent local cytotoxicity of STINGel treatment. However, other explanations for the success of this system are possible. For example, a recent study with a similar CDN molecule showed that treatment efficacy was improved by combination with positively charged poly-arginine cell penetrating peptides, increasing cellular uptake and CDN drug internalization (Yildiz et al., 2015). CDNs are known to suffer from poor membrane permeability due to their negative phosphate linkages, often requiring high dosages or even viral transfection to aid internalization (McWhirter et al., 2009). Thus a reasonable hypothesis is that the complexation of the negative drug molecules with the highly positive MDP hydrogel in this study achieves not only controlled release, but also enhances cellular uptake (Yildiz et al., 2015). Further studies will investigate the mechanism of STINGel in detail.

A significant advantage of the delivery system used in this study is that anti-tumor efficacy is seen after only single injection of MDP biomaterial given at day 3 post tumor cell inoculation. In previous studies, sufficient activation of STING pathway required multiple CDN injections, and led only to a subset of MOC1 tumor rejection and unsuccessful MOC2 tumor rejection (Moore et al., 2016). Thus, as expected a single injection of CDN alone remained ineffective in preventing tumor growth. However a single injection of MDP biomaterial loaded with the same concentration of CDN (STINGel) is highly effective in maintain tumor clearance and rejecting tumor growth.

The inventors demonstrated successful rejection of challenging MOC2-E6E7 tumors in wild-type C57BL/6 mice with single injection of STINGel, establishing that 60% of STINGel treated mice exhibit complete anti-tumor response and acquired immunity. All mice that were rechallenged with a secondary inoculation exhibited no tumor growth, demonstrating that the inventors' MDP biomaterial enables a persistent immunological memory and promising durability of response. The inventors believe that their injectable material creates and prolongs a period of high, localized CDN concentration, and thus can overcome the limitations associated with CDN monotherapy that have required higher and repeated doses to be administered for effective treatment to be observed (Moore et al., 2016).

In principle, one might expect that CDN loaded into any hydrogel may have the same effect as observed here. In order to understand the differences in delivery material, the inventors also evaluated an off-the-shelf material commonly used, a collagen hydrogel. Notably, these data show that CDN loaded collagen had no effect on improving survival over CDN alone. This suggests that the specific design criteria of the MDP is important for the drug delivery kinetics, supported by the fact that the release data from collagen hydrogels is significantly inferior to the MDP. Therefore, the inventors believe that they have developed a uniquely effective biomaterial, a delivery platform capable of revitalizing CDN immunotherapy's future in the lab and the clinic.

In conclusion, the inventors have developed a cyclic dinucleotide-loaded multidomain peptide hydrogel they call STINGel, which dramatically improves overall survival in a challenging murine oral cancer model compared to CDN monotherapy injection. In addition to a six-fold improvement in survival, 100% of surviving mice demonstrate immunological memory and reject a secondary challenge of cancer cells. STINGel shows extended-release kinetics compared to a CDN loaded collagen gel. This translates into superior survival demonstrating that the chemistry and structure of the MDP hydrogel plays a critical role which is not duplicated by collagen. The controlled release of CDN provided by STINGel creates a high local CDN concentration which is observed to affect the immediate vicinity of the hydrogel in vivo for at least seven days, including high immune cell recruitment and cytotoxicity. This suggests a mechanism for the improvement in survival observed over CDN alone or CDN poorly delivered by a collagen hydrogel, in which the local CDN concentration is rapidly depleted. Future studies will address these and other mechanistic issues in greater detail as the inventors explore the scope of STINGel immunotherapy.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference:

Abalsser et al., *Nature*, 498:380-384, 2013.
AduroBiotech, NCT02675439: Feb. 5, 2016 ed.; National Institute of Health: ClinicalTrails.gov, 2017.
Atkins et al., *J Natl Cancer Inst.* 2016 June; 108(6):djv414.
Aulisa et al., *Biomacromolecules* 2009 Sep. 14; 10(9):2694-8.
Austin-Ward and Villaseca, *Rev. Med. Chil.*, 126(7):838-45, 1998.
Bakota et al., *Biomacromolecules*, 2011 May 9; 12(5):1651-7.
Barber, G. N., *Nat Rev Immunol* 2015, 15 (12), 760-770.
Bianchi, M. E., *J Leukocyte Biol* 2007, 81 (1), 1-5.
Bukowski et al., *Clin. Cancer Res.*, 4(10):2337-47, 1998.
Burdette and Vance, Nature *Immunol* 2013, 14 (1), 19-26.
Burdette et al., *Nature* 2011, 478 (7370), 515-518.
Cancer of the Oral Cavity and Pharynx—SEER Fast Fact Sheets, 2012.
Carolina & Chervin, *F1000Research*, 2016; 5:803.
Cerboni et al., *J Exp Med* 2017, 214 (6), 1769.
Chandra et al., *Cancer Immunol. Res.*, 2:901-910, 2014.
Chaturvedi et al., *J Clin Oncol.* 2008 Feb. 1; 26(4):612-9.
Christodoulides et al., *Microbiology*, 144(Pt 11):3027-37, 1998.
Corrales et al., *Cell Rep.* 2015 May 19; 11(7):1018-30.
Davidson et al., *J. Immunother.*, 21(5):389-98, 1998.
Diamond et al., *J Exp Med* 2011 Sep. 26; 208(10):1989-2003.
Diner et al., *Cell Rep.* 2013 May 30; 3(5):1355-61.
Dong et al., *J. Am. Chem. Soc.* 2007 Oct. 17; 129(41):12468-72.
Downey et al., *PloS One*, 9:e99988, 2014
Dubensky et al., *Ther. Adv. Vaccines*, 1:131-143, 2013.
Economopoulou et al., *Curr Treat Options Oncol.* 2016 August; 17(8):40.
Fast Facts. National Cancer Institute, Surveillance Epidemiology and End Results (SEER), 2012.
Ferris et al., *N Engl J Med.* 2016 Nov. 10; 375(19):1856-67.
Fuertes et al., *J Exp Med.* 2011 Sep. 26; 208(10):2005-16.
Gadkaree et al., *Head Neck* 2017 Mar. 21; 16(Suppl 1):3-n/a.
Galler et al., *J. Am. Chem. Soc.* 2010 Mar. 10; 132(9):3217-23.
Galler et al., TISSUE ENGINEERING PART A". Mary Ann Liebert, Inc. 140 Huguenot Street, 3rd Floor New Rochelle, NY 10801 USA; 2012 January; 18(1-2):176-84.
Galon et al., *J Transl Med. BioMed Central;* 2012 Oct. 3; 10(1):205.
Guy & Fields *Meth. Enzymol.* 1997; 289:67-83.
Hanibuchi et al., *Int. J. Cancer,* 78(4):480-485, 1998.
Hanson et al., *J. Clin. Invest.*, 125:2532-2546, 2017.
Harlin et al., *Cancer Res.* 2009 Apr. 1; 69(7):3077-85.
Hellstrand et al., *Acta Oncol.*, 37(4):347-353, 1998.
Hui and Hashimoto, *Infect. Immun.*, 66(11):5329-36, 1998.
Ju et al., *Gene Ther.*, 7(19):1672-1679, 2000.
Judd et al., *Otolaryngol Head Neck Surg.* 2012 September; 147(3):493-500.
Judd et al., *Cancer Res.* 2012 Jan. 1; 72(1):365-74.
Karaolis et al., *Nature*, 461:788-792, 2005.
Klune et al., *Mol Med* 2008, 14 (7-8), 476-484.
Koziol et al., *Biometrics* 1981 June; 37(2):383-90.
Koziol et al., *Statistics in Medicine*, 1(1):83-89, 1982.
Kumar et al. *J. Am. Chem. Soc.* 2015 Apr. 15; 137(14):4823-30.
Kumar et al., *Biomaterials* 2016, 98, 113-119.
Kumar et al., *ACS Nano* 2015, 9 (1), 860-868.
Lei et al., *PLoS ONE* 2009, 4 (5), e5466.
Lewis et al., *Oncology* 2015 September; 29(9):616-26.
Li et al., *Biomacromolecules* 2016 Jun. 13; 17(6):2087-95.
Margolin K. *Curr Treat Options Oncol.*, 2016 September; 17(9):48.
McWhirter et al., *J Exp Med* 2009, 206 (9), 1899-1911.
Méry et al., *Oral Oncology* 2017 February; 65:51-6.
Mitchell et al., *Ann. NY Acad. Sci.*, 690:153-166, 1993.
Mitchell et al., *J. Clin. Oncol.*, 8(5):856-869, 1990.
Miyabe et al., *J. Controlled Release*, 184:20-27, 2014.
Modena et al., *Oncol Rev.* 2016 Apr. 15; 10(1):293.
Moore et al., *Cancer Immunol Res.* 2016 Apr. 13; 4(7):611-20.
Moore et al., *Accounts of Chem Res* 2017, 50 (4), 714-722.
Morton et al., *Arch. Surg.*, 127:392-399, 1992.
Ohkuri et al., *Cancer Immunol. Res.*, 2:1199-1208, 2014.
Onken et al., *Clin. Cancer Res.* 2014 Mar. 25; 20(11):2873-84.
Pietras et al., *Oncogene*, 17(17):2235-49, 1998.
Qin et al., *Proc. Natl. Acad. Sci. USA,* 95(24):14411-14416, 1998.
Ravindranath and Morton, *Intern. Rev. Immunol.*, 7: 303-329, 1991.
Remington's Pharmaceutical Sciences, 15$^{th}$ Ed., 1035-1038 and 1570-1580, 1990.
Remington's Pharmaceutical Sciences, 15$^{th}$ Ed., 3:624-652, 1990.
Romling & Amikan, *Curr. Opin. Microbiol.*, 9:218-228, 2006.
Rosenberg et al., *Ann. Surg.* 210(4):474-548, 1989.
Rosenberg et al., *N. Engl. J. Med.*, 319:1676, 1988.
Tamura et al., *Annu Rev Immunol* 2008, 26 (1), 535-584.
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 7,569,555
U.S. Pat. No. 7,592,326
U.S. Pat. No. 7,709,458
U.S. Patent Publication 2014/0205653
U.S. Patent Publication 2008/0286296

Wellings & Atherton, *Meth. Enzymol.* 289:44-67, 1997.
Wickremasinghe et al., *ACS Biomater. Sci. Eng.* 2015 Sep. 14; 1(9):845-54.
WO2013/185052
WO2014/093936
WO2016/096577
Yildiz et al., *Eur. J. Immunol.* 2015 April; 45(4):1170-9.
Young et al., *J Oral Maxil Surg* 75 (10), 2017, e331-e332.
Young et al., *J Dent Res* 96 (A), 2017.

3'3'-cGAMP, c-di-AMP, 2'3'-c-di-AMP, 2'3'-c-di-AM(PS)$_2$, c-di-GMP, c-di-UMP, c-di-IMP.

5. The composition of claim 1, wherein peptides of MDP hydrogel are 18-30 residues in length.

6. The composition of claim 1, wherein peptides of the MDP hydrogel have about a 3:1 ratio of hydrophilic to hydrophobic charged residues.

7. The composition of claim 1, wherein the peptides of the MDP hydrogel contain a bio-mimetic sequence.

What is claimed is:

1. A composition comprising (a) a multi-domain peptide (MDP) hydrogel K$_2$(SL)$_6$K$_2$ (SEQ ID NO: 3) or R$_2$(SL)$_6$R$_2$ (SEQ ID NO: 4) and (b) a cyclic dinucleotide (CDN).

2. The composition of claim 1, wherein the CDN is a natural endogenous CDN.

3. The composition of claim 1, wherein the CDN is a CDN analog comprising a modified base or non-natural internucleoside linkage.

4. The composition of claim 1, the CDN is dithio-(R$_P$, R$_P$)-[cyclic[A(2',5')pA(3',5')p]], 2'2'-cGAMP, 2'3'-cGAMP, 8. The composition of claim 1, wherein the MDP hydrogel comprises a degradable sequence containing a tumor specific peptide.

9. The composition of claim 1, wherein the MDP hydrogel and the CDN are covalently or non-covalently bound to each other.

10. The composition of claim 1, wherein the endogenous CDN is produced by cGAS.

11. The composition of claim 1, wherein the CDN is a synthetic CDN.

* * * * *

UNITED STATES PATENT AND TRADEMARK OFFICE
CERTIFICATE OF CORRECTION

| | | |
|---|---|---|
| PATENT NO. | : 11,969,499 B2 | |
| APPLICATION NO. | : 16/618043 | |
| DATED | : April 30, 2024 | |
| INVENTOR(S) | : Young et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this
Twelfth Day of November, 2024

*Katherine Kelly Vidal*

Katherine Kelly Vidal
*Director of the United States Patent and Trademark Office*